United States Patent
Thompson

(10) Patent No.: US 12,421,528 B2
(45) Date of Patent: Sep. 23, 2025

(54) PLASMID ENCODING A DNAse-I AND Fc FUSION PROTEIN

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/964,137

(22) Filed: Nov. 29, 2024

(65) Prior Publication Data

US 2025/0263743 A1    Aug. 21, 2025

Related U.S. Application Data

(62) Division of application No. 18/582,222, filed on Feb. 20, 2024.

(51) Int. Cl.
| | |
|---|---|
| C12N 15/00 | (2006.01) |
| C07K 14/48 | (2006.01) |
| C07K 14/62 | (2006.01) |
| C07K 14/705 | (2006.01) |
| C12N 9/22 | (2006.01) |
| C12N 15/86 | (2006.01) |

(52) U.S. Cl.
CPC .............. *C12N 15/86* (2013.01); *C07K 14/48* (2013.01); *C07K 14/62* (2013.01); *C07K 14/705* (2013.01); *C07K 14/70596* (2013.01); *C12N 9/22* (2013.01); *C07K 2319/30* (2013.01); *C12N 2750/14143* (2013.01); *C12N 2800/00* (2013.01)

(58) Field of Classification Search
None
See application file for complete search history.

(56) References Cited

U.S. PATENT DOCUMENTS

| | | |
|---|---|---|
| 8,841,416 B2 | 9/2014 | Ledbetter |
| 11,085,055 B2 | 8/2021 | Mallol et al. |
| 11,162,102 B2 | 11/2021 | Minshull et al. |
| 11,359,001 B2 | 6/2022 | Lancaster |
| 11,530,423 B1 | 12/2022 | Thompson |
| 11,873,505 B2 | 1/2024 | Thompson |
| 11,976,104 B2 | 5/2024 | Wei |
| 12,018,274 B2 | 6/2024 | Thompson |
| 12,134,770 B1 | 11/2024 | Thompson |
| 12,180,521 B2 | 12/2024 | Ledbetter |
| 2003/0104523 A1 | 6/2003 | Bauer |
| 2021/0253664 A1 | 8/2021 | Wei |
| 2024/0026377 A1 | 1/2024 | Thompson |
| 2025/0002884 A1 | 1/2025 | Posada |
| 2025/0011445 A1* | 1/2025 | Bergmann ........... A61K 31/616 |

FOREIGN PATENT DOCUMENTS

| | | | |
|---|---|---|---|
| CA | 2721333 A1 | 10/2009 | |
| CN | 114829384 | 7/2022 | |
| IN | P202305938 | 7/2023 | |
| KR | 100808908 | * 3/2008 | |
| WO | 2004096156 A2 | 11/2004 | |
| WO | 2020041590 A1 | 2/2020 | |
| WO | 2021168413 A1 | 8/2021 | |
| WO | WO-2022074236 A2 * | 4/2022 | ......... A61K 38/1761 |
| WO | 2022178078 A1 | 8/2022 | |
| WO | 2023051412 A1 | 4/2023 | |
| WO | 2023088351 A1 | 5/2023 | |
| WO | 2024107701 A2 | 5/2024 | |
| WO | 2024191937 A2 | 9/2024 | |

OTHER PUBLICATIONS

Dwyer et al. (J. Biol. Chem. 274:9738-43, 1999) (Year: 1999).
Chapter 7 Monomeric Fc-Fusion Proteins Baisong Mei, Susan C. Low, Snejana Krassova, Robert T. Peters, Glenn F. Pierce.Jennifer A. Dumont Book Editor(s):Stefan R. Schmidt First published: Feb. 12, 2013 https://doi.org/10.1002/9781118354599.ch7 (Year: 2013).
A rationally engineered DNase1-Fc fusion protein ameliorates autoimmune glomerulonephritis. By: Mouchess, Maria [Reprint Author] Journal of Immunology, (May 1, 2019) vol. 202, No. 1, Suppl. S, pp. 132.4. (Year: 2019).
A Rationally Engineered Hyperactive Actin-Resistant DNase1-Fc Fusion Protein Ameliorates Autoimmune Glomerulonephritis. By: Austin, Cary D. FASEB Journal, (Apr. 2019) vol. 33, No. Suppl. 1, pp. 802.10. (Year. 2019).
Bottoni et al. "Targeting BTK through microRNA in chronic lymphocytic leukemia." Blood, The Journal of the American Society of Hematology 128.26 (2016): 3101-3112.

(Continued)

*Primary Examiner* — Michael C Wilson

(74) *Attorney, Agent, or Firm* — Gowling WLG (Canada) LLP

(57) ABSTRACT

Some embodiments of the present disclosure relate to one or more compositions that upregulate the production of one or more sequences of mRNA. The sequences of mRNA may encode for translation of a target biomolecule, thereby causing an increase in bioavailability of the target biomolecule within a subject that is administered the one or more compositions. In some embodiments of the present disclosure, the target biomolecule is a fusion protein with an Fc fragment, such as a toll-like receptor 3-Fc (TLR3-Fc). In some embodiments of the present disclosure, the target biomolecule is toll-like receptor 9-Fc (TLR9-Fc). In some embodiments of the present disclosure, the target biomolecule is deoxyribonuclease I-Fc (DNAse I-Fc). In some embodiments of the present disclosure, the target biomolecule is neural growth factor-Fc (NGF-Fc). In some embodiments of the present disclosure, the target biomolecule is insulin-Fc.

3 Claims, No Drawings

Specification includes a Sequence Listing.

(56) References Cited

OTHER PUBLICATIONS

O'Brien et al. "Overview of microRNA biogenesis, mechanisms of actions, and circulation." Frontiers in endocrinology 9 (2018): 402.
Gorski et al. "RNA-based recognition and targeting: sowing the seeds of specificity." Nature Reviews Molecular Cell Biology 18.4 (2017): 215-228.
Brutons Tyrosine Kinase Genbank Sequence (2023).
Christensen et al. "Recombinant adeno-associated virus-mediated microRNA delivery into the postnatal mouse brain reveals a role for miR-134 in dendritogenesis in vivo." Frontiers in neural circuits 3 (2010): 848.
Bofill-De Ros et al. "Guidelines for the optimal design of miRNA-based shRNAs." Methods 103 (2016): 157-166.
Denzler et al. "Impact of microRNA levels, target-site complementarity, and cooperativity on competing endogenous RNA-regulated gene expression." Molecular cell 64.3 (2016): 565-579.
Van Den Berg et al. "Design of effective primary microRNA mimics with different basal stem conformations." Molecular Therapy Nucleic Acids 5 (2016).
Nature (2010. Gene Expression. Scitable. Available online at Nature.com) <https://www.nature.com/scitable/topicpage/gene-expression-14121669> (2010).
GenBank EGF Sequence (2023).
Ahmadzadeh et al. "BRAF mutation in hairy cell leukemia." Oncology reviews 8.2 (2014): 253.
Patton et al. "Biogenesis, delivery, and function of extracellular RNA." Journal of extracellular vesicles 4.1 (2015): 27494.
Clark et al. "Detection of BRAF splicing variants in plasma-derived cell-free nucleic acids and extracellular vesicles of melanoma patients failing targeted therapy therapies." Oncotarget 11.44 (2020): 4016.
NCBI search results for SEQ ID No. 5 (2024).
NCBI Nucleotide Sequence ALK Lingand, search performed Dec. 26, 2024 (2023).
NCBI Nucleotide Sequence ALK Receptor, search performed Dec. 26, 2024 (2023).
GenBank EGFR Sequence (2023).
GenBank FLT3 Sequence (2024).
NCBI Nucleotide Sequence for PARP, search performed Dec. 26, 2024 (2024).
Tritschler et al. "Concepts and limitations for learning developmental trajectories from single cell genomics." Development 146.12 (2019): dev170506.
Kondratov et al. "Direct head-to-head evaluation of recombinant adeno-associated viral vectors manufactured in human versus insect cells." Molecular Therapy 25.12 (2017): 2661-2675.
Wang et al. "Adeno-associated virus vector as a platform for gene therapy delivery." Nature reviews Drug discovery 18.5 (2019): 358-378.

\* cited by examiner

PLASMID ENCODING A DNAse-I AND Fc FUSION PROTEIN

This application contains a Sequence Listing electronically submitted via Patent Center to the United States Patent and Trademark Office as an XML Document file entitled "A8149440US-Sequence Listing.xml" created on 2024 Feb. 8 and having a size of 68,245 bytes. The information contained in the Sequence Listing is incorporated by reference herein.

TECHNICAL FIELD

The present disclosure generally relates to compositions for regulating the production of fusion proteins. In particular, the present disclosure relates to compositions for regulating gene expression and, consequently, the production of fusion proteins.

BACKGROUND

Bioactive molecules, including toll-like receptors, enzymes, and hormones, are necessary for the homeostatic control of biological systems.

When bioactive molecules are over-expressed, under-expressed or mis-expressed, homeostasis is lost, and disease is often the result.

As such, it may be desirable to establish therapies, treatments and/or interventions that address when homeostasis and the regulation of bioactive molecules are lost in order to prevent or treat the resulting disease.

SUMMARY

Some embodiments of the present disclosure relate to one or more compositions that upregulate the production of one or more sequences of mRNA. The sequences of mRNA may encode for translation of a target biomolecule, thereby causing an increase in bioavailability of the target biomolecule within a subject that is administered the one or more compositions. In some embodiments of the present disclosure, the target biomolecule is a fusion protein with an Fc fragment, such as a toll-like receptor 3-Fc (TLR3-Fc). In some embodiments of the present disclosure, the target biomolecule is toll-like receptor 9-Fc (TLR9-Fc). In some embodiments of the present disclosure, the target biomolecule is deoxyribonuclease I-Fc (DNAse I-Fc). In some embodiments of the present disclosure, the target biomolecule is neural growth factor-Fc (NGF-Fc). In some embodiments of the present disclosure, the target biomolecule is insulin-Fc.

In some embodiments of the present disclosure the compositions comprise a plasmid of deoxyribonucleic acid (DNA) that includes one or more insert sequences of nucleic acids that encode for the production of mRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the mRNA and, consequently, increased translation of the target biomolecule by one or more of the subject's cells.

Some embodiments of the present disclosure relate to a recombinant plasmid (RP). In some embodiments of the present disclosure, the RP comprises a nucleotide sequence of SEQ ID NO.1 and SEQ ID NO.2. The RP comprises a nucleotide sequence encoding one or more nucleotide sequences encoding an mRNA sequence that encodes for the fusion protein DNAse I-Fc.

Some embodiments of the present disclosure relate to a recombinant plasmid. In some embodiments of the present disclosure, the RP comprises a nucleotide sequence of SEQ ID NO.1 and SEQ ID NO.3. The RP comprises a nucleotide sequence encoding one or more nucleotide sequences encoding an mRNA sequence that encodes for the fusion protein TLR3-FC.

Some embodiments of the present disclosure relate to a recombinant plasmid. In some embodiments of the present disclosure, the RP comprises a nucleotide sequence of SEQ ID NO.1 and SEQ ID NO.4. The RP comprises a nucleotide sequence encoding one or more nucleotide sequences encoding an mRNA sequence that encodes for the fusion protein TLR9-Fc.

Some embodiments of the present disclosure relate to a recombinant plasmid. In some embodiments of the present disclosure, the RP comprises a nucleotide sequence of SEQ ID NO.1 and SEQ ID NO.5. The RP comprises a nucleotide sequence encoding one or more nucleotide sequences encoding an mRNA sequence that encodes for the fusion protein NGF-Fc.

Some embodiments of the present disclosure relate to a recombinant plasmid. In some embodiments of the present disclosure, the RP comprises a nucleotide sequence of SEQ ID NO.1 and SEQ ID NO.6. The RP comprises a nucleotide sequence encoding one or more nucleotide sequences encoding an mRNA sequence that encodes for the fusion protein insulin-Fc.

Some embodiments of the present disclosure relate to a method of making a composition/target cell complex. The method comprising a step of administering a RP comprising SEQ ID NO.1 and one of SEQ ID NO.2, SEQ ID NO.3, SEQ ID NO.4, SEQ ID NO.5 or SEQ ID NO.6 to a target cell for forming the composition/target cell complex, wherein the composition/target cell complex causes the target cell to increase production of one or more sequences of mRNA that increases production of a target biomolecule.

Embodiments of the present disclosure relate to at least one approach for inducing endogenous production of one or more sequences of mRNA that encodes for a target biomolecule, for example TLR3-Fc. A first approach utilizes gene vectors containing nucleotide sequences for increasing the endogenous production of one or more sequences of mRNA, which are complete or partial sequences and/or combinations thereof of TLR3-Fc, which can be administered to a subject to increase the subject's production of one or more sequences of the mRNA.

Embodiments of the present disclosure relate to at least one approach for inducing endogenous production of one or more sequences of mRNA that encodes for a target biomolecule, for example TLR9-Fc. A first approach utilizes gene vectors containing nucleotide sequences for increasing the endogenous production of one or more sequences of mRNA, which are complete or partial sequences and/or combinations thereof of TLR9-Fc, which can be administered to a subject to increase the subject's production of one or more sequences of the mRNA.

Embodiments of the present disclosure relate to at least one approach for inducing endogenous production of one or more sequences of mRNA that encodes for a target biomolecule, for example DNAse I-Fc. A first approach utilizes gene vectors containing nucleotide sequences for increasing the endogenous production of one or more sequences of mRNA, which are complete or partial sequences and/or combinations thereof of DNAse I-Fc, which can be administered to a subject to increase the subject's production of one or more sequences of the mRNA.

Embodiments of the present disclosure relate to at least one approach for inducing endogenous production of one or more sequences of mRNA that encodes for a target biomolecule, for example NGF-Fc. A first approach utilizes gene vectors containing nucleotide sequences for increasing the endogenous production of one or more sequences of mRNA, which are complete or partial sequences and/or combinations thereof of NGF-Fc, which can be administered to a subject to increase the subject's production of one or more sequences of the mRNA.

Embodiments of the present disclosure relate to at least one approach for inducing endogenous production of one or more sequences of mRNA that encodes for a target biomolecule, for example insulin-Fc. A first approach utilizes gene vectors containing nucleotide sequences for increasing the endogenous production of one or more sequences of mRNA, which are complete or partial sequences and/or combinations thereof of insulin-Fc, which can be administered to a subject to increase the subject's production of one or more sequences of the mRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred compositions, methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a protein-Fc fusion molecule that is found within a subject. A biomolecule may be endogenous or exogenous to a subject.

As used therein, the term "target cell" refers to one or more cells and/or cell types that are affected, either directly or indirectly, by a biomolecule.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of mRNA that increases the production of target biomolecules, such as a fusion protein with an Fc fragment. An Fc fragment is the distal portion of the heavy chain of an antibody.

In some embodiments of the present disclosure, the target biomolecule is TLR3-Fc. In some embodiments of the present disclosure, the target biomolecule is TLR9-Fc.

In some embodiments of the present disclosure, the target biomolecule is DNAse I-Fc.

In some embodiments of the present disclosure, the target biomolecule is NGF-Fc.

In some embodiments of the present disclosure, the target biomolecule is insulin-Fc.

Some embodiments of the present disclosure relate to a composition that can be administered to a subject with a condition that results, directly or indirectly, from the dysregulated production of a biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of mRNA that each encode for one or more biomolecules.

In some embodiments of the present disclosure, the composition is an RP that may be used for gene therapy. The gene therapy is useful for increasing the subject's endogenous production of one or more sequences of mRNA that encode for a target biomolecule. For example, the RP can contain one or more nucleotide sequences that cause increased production of one or more nucleotide sequences that cause an increased production of one or more mRNA sequences that encode for one biomolecule, such as TLR3-Fc, TLR9-Fc, DNAse I-Fc, NGF-Fc or insulin-Fc.

In some embodiments of the present disclosure, the delivery vehicle of the RP used for gene therapy may be a vector that comprises a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus *Dependoparvovirus*. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1\times10^{16}$ TCID$_{50}$/kg (50% tissue culture infective dose per kilogram of the patient's body mass). In some embodiments of the present disclosure, the therapeutically effective amount of the composition that is administered to the patient is about $1\times10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments of the present disclosure, the therapeutically effective amount of the composition is between about 10 and about $1\times10^{16}$ TCP/kg.

Some embodiments of the present disclosure relate to an adeno-associated virus (AAV) genome consisting of a RP that when operable inside a target cell will cause the target cell to produce a mRNA sequence that upregulates production of a biomolecule, with examples being TLR3-Fc, TLR9-Fc, DNAse I-Fc, NGF-Fc, or insulin-Fc. The RP is comprised of AAV2 inverted terminal repeats (ITRs), a composite CASI promoter, and a human growth hormone (HGH) signal peptide followed by a mRNA expression cassette encoding for TLR3-Fc, TLR9-Fc, DNAse I-Fc, NGF-Fc, or insulin-Fc, followed by a Woodchuck Hepatitis Virus post-transcriptional regulatory element (WPRE) and a Simian virus 40 (SV40) polyadenylation (polyA) signal.

SEQ ID NO. 1 (backbone sequence No. 1):
5'TTCTAGAATAATCAACCTCTGGATTACAAAATTTGTGAAAGATTGACTGGTATTCTTAACT

ATGTTGCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAGGAGT

TGTGGCCCGTTGTCAGGCAACGTGGCGTGGTGTGCACTGTGTTTGCTGACGCAACCCCCACTG

GTTGGGGCATTGCCACCACCTGTCAGCTCCTTTCCGGGACTTTCGCTTTCCCCCTCCCTATTG

CCACGGCGGAACTCATCGCCGCCTGCCTTGCCCGCTGCTGGACAGGGGCTCGGCTGTTGGGCA

CTGACAATTCCGTGGTGTTGTCGGGGAAATCATCGTCCTTTCCTTGGCTGCTCGCCTGTGTTG

CCACCTGGATTCTGCGCGGGACGTCCTTCTGCTACGTCCCTTCGGCCCTCAATCCAGCGGACC

TTCCTTCCCGCGGCCTGCTGCCGGCTCTGCGGCCTCTTCCGCGTCTTCGCCTTCGCCCTCAGA

CGAGTCGGATCTCCCTTTGGGCCGCCTCCCCGCCTAAGCTTATCGATACCGTCGAGATCTAAC

TTGTTTATTGCAGCTTATAATGGTTACAAATAAAGCAATAGCATCACAAATTTCACAAATAAA

GCATTTTTTCACTGCATTCTAGTTGTGGTTTGTCCAAACTCATCAATGTATCTTATCATGTC

TGGATCTCGACCTCGACTAGAGCATGGCTACGTAGATAAGTAGCATGGCGGGTTAATCATTAA

CTACAAGGAACCCCTAGTGATGGAGTTGGCCACTCCCTCTCTGCGCGCTCGCTCGCTCACTGA

GGCCGGGCGACCAAAGGTCGCCCGACGCCCGGGCTTTGCCCGGGCGGCCTCAGTGAGCGAGCG

AGCGCGCCAGCTGGCGTAATAGCGAAGAGGCCCGCACCGATCGCCCTTCCCAACAGTTGCGCA

GCCTGAATGGCGAATGGAATTCCAGACGATTGAGCGTCAAAATGTAGGTATTTCCATGAGCGT

TTTTCCTGTTGCAATGGCTGGCGGTAATATTGTTCTGGATATTACCAGCAAGGCCGATAGTTT

GAGTTCTTCTACTCAGGCAAGTGATGTTATTACTAATCAAAGAAGTATTGCGACAACGGTTAA

TTTGCGTGATGGACAGACTCTTTTACTCGGTGGCCTCACTGATTATAAAAACACTTCTCAGGA

TTCTGGCGTACCGTTCCTGTCTAAAATCCCTTTAATCGGCCTCCTGTTTAGCTCCCGCTCTGA

TTCTAACGAGGAAAGCACGTTATACGTGCTCGTCAAAGCAACCATAGTACGCGCCCTGTAGCG

GCGCATTAAGCGCGGCGGGTGTGGTGGTTACGCGCAGCGTGACCGCTACACTTGCCAGCGCCC

TAGCGCCCGCTCCTTTCGCTTTCTTCCCTTCCTTTCTCGCCACGTTCGCCGGCTTTCCCCGTC

AAGCTCTAAATCGGGGGCTCCCTTTAGGGTTCCGATTTAGTGCTTTACGGCACCTCGACCCCA

AAAAACTTGATTAGGGTGATGGTTCACGTAGTGGGCCATCGCCCTGATAGACGGTTTTTCGCC

CTTTGACGTTGGAGTCCACGTTCTTTAATAGTGGACTCTTGTTCCAAACTGGAACAACACTCA

ACCCTATCTCGGTCTATTCTTTTGATTTATAAGGGATTTTGCCGATTTCGGCCTATTGGTTAA

AAAATGAGCTGATTTAACAAAAATTTAACGCGAATTTTAACAAAATATTAACGTTTACAATTT

AAATATTTGCTTATACAATCTTCCTGTTTTTGGGGCTTTTCTGATTATCAACCGGGGTACATA

TGATTGACATGCTAGTTTTACGATTACCGTTCATCGATTCTCTTGTTTGCTCCAGACTCTCAG

GCAATGACCTGATAGCCTTTGTAGAGACCTCTCAAAAATAGCTACCCTCTCCGGCATGAATTT

ATCAGCTAGAACGGTTGAATATCATATTGATGGTGATTTGACTGTCTCCGGCCTTTCTCACCC

GTTTGAATCTTTACCTACACATTACTCAGGCATTGCATTTAAAATATATGAGGGTTCTAAAAA

TTTTTATCCTTGCGTTGAAATAAAGGCTTCTCCCGCAAAAGTATTACAGGGTCATAATGTTTT

TGGTACAACCGATTTAGCTTTATGCTCTGAGGCTTTATTGCTTAATTTTGCTAATTCTTTGCC

TTGCCTGTATGATTTATTGGATGTTGGAATTCCTGATGCGGTATTTTCTCCTTACGCATCTGT

GCGGTATTTCACACCGCATATGGTGCACTCTCAGTACAATCTGCTCTGATGCCGCATAGTTAA

GCCAGCCCCGACACCCGCCAACACCCGCTGACGCGCCCTGACGGGCTTGTCTGCTCCCGGCAT

CCGCTTACAGACAAGCTGTGACCGTCTCCGGGAGCTGCATGTGTCAGAGGTTTTCACCGTCAT

-continued
CACCGAAACGCGCGAGACGAAAGGGCCTCGTGATACGCCTATTTTTATAGGTTAATGTCATGA
TAATAATGGTTTCTTAGACGTCAGGTGGCACTTTTCGGGGAAATGTGCGCGGAACCCCTATTT
GTTTATTTTTCTAAATACATTCAAATATGTATCCGCTCATGAGACAATAACCCTGATAAATGC
TTCAATAATATTGAAAAAGGAAGAGTATGAGTATTCAACATTTCCGTGTCGCCCTTATTCCCT
TTTTTGCGGCATTTTGCCTTCCTGTTTTTGCTCACCCAGAAACGCTGGTGAAAGTAAAAGATG
CTGAAGATCAGTTGGGTGCACGAGTGGGTTACATCGAACTGGATCTCAACAGCGGTAAGATCC
TTGAGAGTTTTCGCCCCGAAGAACGTTTTCCAATGATGAGCACTTTTAAAGTTCTGCTATGTG
GCGCGGTATTATCCCGTATTGACGCCGGGCAAGAGCAACTCGGTCGCCGCATACACTATTCTC
AGAATGACTTGGTTGAGTACTCACCAGTCACAGAAAAGCATCTTACGGATGGCATGACAGTAA
GAGAATTATGCAGTGCTGCCATAACCATGAGTGATAACACTGCGGCCAACTTACTTCTGACAA
CGATCGGAGGACCGAAGGAGCTAACCGCTTTTTTGCACAACATGGGGGATCATGTAACTCGCC
TTGATCGTTGGGAACCGGAGCTGAATGAAGCCATACCAAACGACGAGCGTGACACCACGATGC
CTGTAGCAATGGCAACAACGTTGCGCAAACTATTAACTGGCGAACTACTTACTCTAGCTTCCC
GGCAACAATTAATAGACTGGATGGAGGCGGATAAAGTTGCAGGACCACTTCTGCGCTCGGCCC
TTCCGGCTGGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGACGGGGAGTC
AGGCAACTATGGATGAACGAAATAGACAGATCGCTGAGATAGGTGCCTCACTGATTAAGCATT
GGTAACTGTCAGACCAAGTTTACTCATATATACTTTAGATTGATTTAAAACTTCATTTTTAAT
TTAAAAGGATCTAGGTGAAGATCCTTTTTGATAATCTCATGACCAAAATCCCTTAACGTGAGT
TTTCGTTCCACTGAGCGTCAGACCCCGTAGAAAAGATCAAAGGATCTTCTTGAGATCCTTTTT
TTCTGCGCGTAATCTGCTGCTTGCAAACAAAAAAACCACCGCTACCAGCGGTGGTTTGTTTGC
CGGATCAAGAGCTACCAACTCTTTTTCCGAAGGTAACTGGCTTCAGCAGAGCGCAGATACCAA
ATACTGTCCTTCTAGTGTAGCCGTAGTTAGGCCACCACTTCAAGAACTCTGTAGCACCGCCTA
CATACCTCGCTCTGCTAATCCTGTTACCAGTGGCTGCTGCCAGTGGCGATAAGTCGTGTCTTA
CCGGGTTGGACTCAAGACGATAGTTACCGGATAAGGCGCAGCGGTCGGGCTGAACGGGGGGTT
CGTGCACACAGCCCAGCTTGGAGCGAACGACCTACACCGAACTGAGATACCTACAGCGTGAGC
TATGAGAAAGCGCCACGCTTCCCGAAGGGAGAAAGGCGGACAGGTATCCGGTAAGCGGCAGGG
TCGGAACAGGAGAGCGCACGAGGGAGCTTCCAGGGGGAAACGCCTGGTATCTTTATAGTCCTG
TCGGGTTTCGCCACCTCTGACTTGAGCGTCGATTTTTGTGATGCTCGTCAGGGGGGCGGAGCC
TATGGAAAAACGCCAGCAACGCGGCCTTTTTACGGTTCCTGGCCTTTTGCTGGCCTTTTGCTC
ACATGTTCTTTCCTGCGTTATCCCCTGATTCTGTGGATAACCGTATTACCGCCTTTGAGTGAG
CTGATACCGCTCGCCGCAGCCGAACGACCGAGCGCAGCGAGTCAGTGAGCGAGGAAGCGGAAG
AGCGCCCAATACGCAAACCGCCTCTCCCCGCGCGTTGGCCGATTCATTAATGCAGCAGCTGCG
CGCTCGCTCGCTCACTGAGGCCGCCCGGGCAAAGCCCGGGCGTCGGGCGACCTTTGGTCGCCC
GGCCTCAGTGAGCGAGCGAGCGCGCAGAGAGGGAGTGGCCAACTCCATCACTAGGGGTTCCTT
GTAGTTAATGATTAACCCGCCATGCTACTTATCTACGTAGCCATGCTCTAGGACATTGATTAT
TGACTAGTGGAGTTCCGCGTTACATAACTTACGGTAAATGGCCCGCCTGGCTGACCGCCCAAC
GACCCCCGCCCATTGACGTCAATAATGACGTATGTTCCCATAGTAACGCCAATAGGGACTTTC
CATTGACGTCAATGGGTGGAGTATTTACGGTAAACTGCCCACTTGGCAGTACATCAAGTGTAT
CATATGCCAAGTACGCCCCCTATTGACGTCAATGACGGTAAATGGCCCGCCTGGCATTATGCC
CAGTACATGACCTTATGGGACTTTCCTACTTGGCAGTACATCTACGTATTAGTCATCGCTATT -continued ACCATGGTCGAGGTGAGCCCCACGTTCTGCTTCACTCTCCCCATCTCCCCCCCCTCCCCACCC
CCAATTTTGTATTTATTTATTTTTTAATTATTTTGTGCAGCGATGGGGGCGGGGGGGGGGGGG
GGCGCGCGCCAGGCGGGGCGGGGGGGGCGAGGGGCGGGGCGGGGCGAGGCGGAGAGGTGCGG
CGGCAGCCAATCAGAGCGGCGCGCTCCGAAAGTTTCCTTTTATGGCGAGGCGGCGGCGGCGGC
GGCCCTATAAAAAGCGAAGCGCGCGGCGGGCGGGAGTCGCTGCGCGCTGCCTTCGCCCCGTGC
CCCGCTCCGCCGCCGCCTCGCGCCGCCCGCCCCGGCTCTGACTGACCGCGTTACTAAAACAGG
TAAGTCCGGCCTCCGCGCCGGGTTTTGGCGCCTCCCGCGGGCGCCCCCCTCCTCACGGCGAGC
GCTGCCACGTCAGACGAAGGGCGCAGCGAGCGTCCTGATCCTTCCGCCCGGACGCTCAGGACA
GCGGCCCGCTGCTCATAAGACTCGGCCTTAGAACCCCAGTATCAGCAGAAGGACATTTTAGGA
CGGGACTTGGGTGACTCTAGGGCACTGGTTTTCTTTCCAGAGAGCGGAACAGGCGAGGAAAAG
TAGTCCCTTCTCGGCGATTCTGCGGAGGGATCTCCGTGGGCGGTGAACGCCGATGATGCCTC
TACTAACCATGTTCATGTTTTCTTTTTTTTTCTACAGGTCCTGGGTGACGAACAGGGTACCGC
CACC3'

SEQ ID NO. 2 (mRNA expression cassette No. 2 - DNAse I-Fc):
5'ATGAGGGGCATGAAGCTGCTGGGGCGCTGCTGGCACTGGCGGCCCTACTGCAGGGGCCG
TGTCCCTGAAGATCGCAGCCTTCAACATCCAGACATTTGGGGAGACCAAGATGTCCAATGCCA
CCCTCGTCAGCTACATTGTGCAGATCCTGAGCCGCTATGACATCGCCCTGGTCCAGGAGGTCA
GAGACAGCCACCTGACTGCCGTGGGGAAGCTGCTGGACAACCTCAATCAGGATGCACCAGACA
CCTATCACTACGTGGTCAGTGAGCCACTGGGACGGAACAGCTATAAGGAGCGCTACCTGTTCG
TGTACAGGCCTGACCAGGTGTCTGCGGTGGACAGCTACTACTACGATGATGGCTGCGAGCCCT
GCGGGAACGACACCTTCAACCGAGAGCCAGCCATTGTCAGGTTCTTCTCCCGGTTCACAGAGG
TCAGGGAGTTTGCCATTGTTCCCCTGCATGCGGCCCCGGGGACGCAGTAGCCGAGATCGACG
CTCTCTATGACGTCTACCTGGATGTCCAAGAGAAATGGGGCTTGGAGGACGTCATGTTGATGG
GCGACTTCAATGCGGGCTGCAGCTATGTGAGACCCTCCCAGTGGTCATCCATCCGCCTGTGGA
CAAGCCCCACCTTCCAGTGGCTGATCCCCGACAGCGCTGACACCACAGCTACACCCACGCACT
GTGCCTATGACAGGATCGTGGTTGCAGGGATGCTGCTCCGAGGCGCCGTTGTTCCCGACTCGG
CTCTTCCCTTTAACTTCCAGGCTGCCTATGGCCTGAGTGACCAACTGGCCCAAGCCATCAGTG
ACCACTATCCAGTGGAGGTGATGCTGAAGGGCGGATCAGGCGGATCACCCAAATCTTGTGACA
AAACTCACACATGCCCACCGTGCCCAGCACCTGAACTCCTGGGGGGACCGTCAGTCTTCCTCT
TCCCCCCAAAACCCAAGGACACCCTCATGATCTCCCGGACCCCTGAGGTCACATGCGTGGTGG
TGGACGTGAGCCACGAAGACCCTGAGGTCAAGTTCAACTGGTACGTGGACGGCGTGGAGGTGC
ATAATGCCAAGACAAAGCCGCGGGAGGAGCAGTACAACAGCACGTACCGTGTGGTCAGCGTCC
TCACCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGGCAGCCCCGAGAACCACAGG
TGTACACCCTGCCCCCATCCCGGGAGGAGATGACCAAGAACCAGGTCAGCCTGACCTGCCTGG
TCAAAGGCTTCTATCCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCTACAGCAAGCTCA
CCGTGGACAAGAGCAGGTGGCAGCAGGGGAACGTCTTCTCATGCTCCGTGATGCATGAGGCTC
TGCACAACCACTACACGCAGAAGAGCCTCTCCCTGTCTCCGGGTAAATAG3'

SEQ ID NO. 3 (mRNA expression cassette No. 3 - TLR3-Fc):
5'GCCAGACCCTGCCGTGCATTTATTTTTGGGGCGGCCTGCTGCCGTTTGGCATGCTGTGCGC -continued

```
GAGCAGCACCACCAAATGCACCGTGAGCCATGAAGTGGCGGATTGCAGCCATCTGAAACTGAC
CCAGGTGCCGGATGATCTGCCGACCAACATTACCGTGCTGAACCTGACCCATAACCAGCTGCG
CCGCCTGCCGGCGGCGAACTTTACCCGCTATAGCCAGCTGACCAGCCTGGATGTGGGCTTTAA
CACCATTAGCAAACTGGAACCGGAACTGTGCCAGAAACTGCCGATGCTGAAAGTGCTGAACCT
GCAGCATAACGAACTGAGCCAGCTGAGCGATAAAACCTTTGCGTTTTGCACCAACCTGACCGA
ACTGCATCTGATGAGCAACAGCATTCAGAAAATTAAAAACAACCCGTTTGTGAAACAGAAAAA
CCTGATTACCCTGGATCTGAGCCATAACGGCCTGAGCAGCACCAAACTGGGCACCCAGGTGCA
GCTGGAAAACCTGCAGGAACTGCTGCTGAGCAACAACAAAATTCAGGCGCTGAAAAGCGAAGA
ACTGGATATTTTTGCGAACAGCAGCCTGAAAAAACTGGAACTGAGCAGCAACCAGATTAAAGA
ATTTAGCCCGGGCTGCTTTCATGCGATTGGCCGCCTGTTTGGCCTGTTTCTGAACAACGTGCA
GCTGGGCCCGAGCCTGACCGAAAAACTGTGCCTGGAACTGGCGAACACCAGCATTCGCAACCT
GAGCCTGAGCAACAGCCAGCTGAGCACCACCAGCAACACCACCTTTCTGGGCCTGAAATGGAC
CAACCTGACCATGCTGGATCTGAGCTATAACAACCTGAACGTGGTGGGCAACGATAGCTTTGC
GTGGCTGCCGCAGCTGGAATATTTTTTCTGGAATATAACAACATTCAGCATCTGTTTAGCCA
TAGCCTGCATGGCCTGTTTAACGTGCGCTATCTGAACCTGAAACGCAGCTTTACCAAACAGAG
CATTAGCCTGGCGAGCCTGCCGAAAATTGATGATTTTAGCTTTCAGTGGCTGAAATGCCTGGA
ACATCTGAACATGGAAGATAACGATATTCCGGGCATTAAAAGCAACATGTTTACCGGCCTGAT
TAACCTGAAATATCTGAGCCTGAGCAACAGCTTTACCAGCCTGCGCACCCTGACCAACGAAAC
CTTTGTGAGCCTGGCGCATAGCCCGCTGCATATTCTGAACCTGACCAAAAACAAAATTAGCAA
AATTGAAAGCGATGCGTTTAGCTGGCTGGGCCATCTGGAAGTGCTGGATCTGGGCCTGAACGA
AATTGGCCAGGAACTGACCGGCCAGGAATGGCGCGGCCTGGAAAACATTTTTGAAATTTATCT
GAGCTATAACAAATATCTGCAGCTGACCCGCAACAGCTTTGCGCTGGTGCCGAGCCTGCAGCG
CCTGATGCTGCGCCGCGTGGCGCTGAAAAACGTGGATAGCAGCCCGAGCCCGTTTCAGCCGCT
GCGCAACCTGACCATTCTGGATCTGAGCAACAACAACATTGCGAACATTAACGATGATATGCT
GGAAGGCCTGGAAAAACTGGAAATTCTGGATCTGCAGCATAACAACCTGGCGCGCCTGTGGAA
ACATGCGAACCCGGGCGGCCCGATTTATTTTCTGAAAGGCCTGAGCCATCTGCATATTCTGAA
CCTGGAAAGCAACGGCTTTGATGAAATTCCGGTGGAAGTGTTTAAAGATCTGTTTGAACTGAA
AATTATTGATCTGGGCCTGAACAACCTGAACACCCTGCCGGCGAGCGTGTTTAACAACCAGGT
GAGCCTGAAAAGCCTGAACCTGCAGAAAAACCTGATTACCAGCGTGGAAAAAAAAGTGTTTGG
CCCGGCGTTTCGCAACCTGACCGAACTGGATATGCGCTTTAACCCGTTTGATTGCACCTGCGA
AAGCATTGCGTGGTTTGTGAACTGGATTAACGAAACCCATACCAACATTCCGGAACTGAGCAG
CCATTATCTGTGCAACACCCCGCCGCATTATCATGGCTTTCCGGTGCGCCTGTTTGATACCAG
CAGCTGCAAAGATAGCGCGCCGTTTGAACTGTTTTTTATGATTAACACCAGCATTCTGCTGAT
TTTTATTTTTATTGTGCTGCTGATTCATTTTGAAGGCTGGCGCATTAGCTTTTATTGGAACGT
GAGCGTGCATCGCGTGCTGGGCTTTAAAGAAATTGATCGCCAGACCGAACAGTTTGAATATGC
GGCGTATATTATTCATGCGTATAAAGATAAAGATTGGGTGTGGGAACATTTTAGCAGCATGGA
AAAAGAAGATCAGAGCCTGAAATTTTGCCTGGAAGAACGCGATTTTGAAGCGGGCGTGTTTGA
ACTGGAAGCGATTGTGAACAGCATTAAACGCAGCCGCAAAATTATTTTTGTGATTACCCATCA
TCTGCTGAAAGATCCGCTGTGCAAACGCTTTAAAGTGCATCATGCGGTGCAGCAGGCGATTGA
ACAGAACCTGGATAGCATTATTCTGGTGTTTCTGGAAGAAATTCCGGATTATAAACTGAACCA
TGCGCTGTGCCTGCGCCGCGGCATGTTTAAAAGCCATTGCATTCTGAACTGGCCGGTGCAGAA
```

-continued

```
AGAACGCATTGGCGCGTTTCGCCATAAACTGCAGGTGGCGCTGGGCAGCAAAAACAGCGTGCA

TGGGCGGATCAGGCGGATCACCCAAATCTTGTGACAAAACTCACACATGCCCACCGTGCCCAG

CACCTGAACTCCTGGGGGGACCGTCAGTCTTCCTCTTCCCCCCAAAACCCAAGGACACCCTCA

TGATCTCCCGGACCCCTGAGGTCACATGCGTGGTGGTGGACGTGAGCCACGAAGACCCTGAGG

TCAAGTTCAACTGGTACGTGGACGGCGTGGAGGTGCATAATGCCAAGACAAAGCCGCGGGAGG

AGCAGTACAACAGCACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCCCATCGAGAAAACCA

TCTCCAAAGCCAAAGGGCAGCCCCGAGAACCACAGGTGTACACCCTGCCCCCATCCCGGGAGG

AGATGACCAAGAACCAGGTCAGCCTGACCTGCCTGGTCAAAGGCTTCTATCCCAGCGACATCG

CCGTGGAGTGGGAGAGCAATGGGCAGCCGGAGAACAACTACAAGACCACGCCTCCCGTGCTGG

ACTCCGACGGCTCCTTCTTCCTCTACAGCAAGCTCACCGTGGACAAGAGCAGGTGGCAGCAGG

GGAACGTCTTCTCATGCTCCGTGATGCATGAGGCTCTGCACAACCACTACACGCAGAAGAGCC

TCTCCCTGTCTCCGGGTAAATAG3'
```

SEQ ID NO. 4 (miRNA expression cassette No. 4 - TLR9-Fc):
```
5'ATGAGGGGCATGAAGCTGCTGGGGGCGCTGCTGGCACTGGCGGCCCTACTGCAGGGGGCCG

TGTCCATGGGCTTTTGCCGCAGCGCGCTGCATCCGCTGAGCCTGCTGGTGCAGGCGATTATGC

TGGCGATGACCCTGGCGCTGGGCACCCTGCCGGCGTTTCTGCCGTGCGAACTGCAGCCGCATG

GCCTGGTGAACTGCAACTGGCTGTTTCTGAAAAGCGTGCCGCATTTTAGCATGGCGGCGCCGC

GCGGCAACGTGACCAGCCTGAGCCTGAGCAGCAACCGCATTCATCATCTGCATGATAGCGATT

TTGCGCATCTGCCGAGCCTGCGCCATCTGAACCTGAAATGGAACTGCCCGCCGGTGGGCCTGA

GCCCGATGCATTTTCCGTGCCATATGACCATTGAACCGAGCACCTTTCTGGCGGTGCCGACCC

TGGAAGAACTGAACCTGAGCTATAACAACATTATGACCGTGCCGGCGCTGCCGAAAAGCCTGA

TTAGCCTGAGCCTGAGCCATACCAACATTCTGATGCTGGATAGCGCGAGCCTGGCGGGCCTGC

ATGCGCTGCGCTTTCTGTTTATGGATGGCAACTGCTATTATAAAAACCCGTGCCGCCAGGCGC

TGGAAGTGGCGCCGGGCGCGCTGCTGGGCCTGGGCAACCTGACCCATCTGAGCCTGAAATATA

ACAACCTGACCGTGGTGCCGCGCAACCTGCCGAGCAGCCTGGAATATCTGCTGCTGAGCTATA

ACCGCATTGTGAAACTGGCGCCGGAAGATCTGGCGAACCTGACCGCGCTGCGCGTGCTGGATG

TGGGCGGCAACTGCCGCCGCTGCGATCATGCGCCGAACCCGTGCATGGAATGCCCGCGCCATT

TTCCGCAGCTGCATCCGGATACCTTTAGCCATCTGAGCCGCCTGGAAGGCCTGGTGCTGAAAG

ATAGCAGCCTGAGCTGGCTGAACGCGAGCTGGTTTCGCGGCCTGGGCAACCTGCGCGTGCTGG

ATCTGAGCGAAAACTTTCTGTATAAATGCATTACCAAAACCAAAGCGTTTCAGGGCCTGACCC

AGCTGCGCAAACTGAACCTGAGCTTTAACTATCAGAAACGCGTGAGCTTTGCGCATCTGAGCC

TGGCGCCGAGCTTTGGCAGCCTGGTGGCGCTGAAAGAACTGGATATGCATGGCATTTTTTTC

GCAGCCTGGATGAAACCACCCTGCGCCCGCTGGCGCGCCTGCCGATGCTGCAGACCCTGCGCC

TGCAGATGAACTTTATTAACCAGGCGCAGCTGGGCATTTTTCGCGCGTTTCCGGGCCTGCGCT

ATGTGGATCTGAGCGATAACCGCATTAGCGGCGCGAGCGAACTGACCGCGACCATGGGCGAAG

CGGATGGCGGCGAAAAAGTGTGGCTGCAGCCGGGCGATCTGGCGCCGGCGCCGGTGGATACCC

CGAGCAGCGAAGATTTTCGCCCGAACTGCAGCACCCTGAACTTTACCCTGGATCTGAGCCGCA

ACAACCTGGTGACCGTGCAGCCGGAAATGTTTGCGCAGCTGAGCCATCTGCAGTGCCTGCGCC

TGAGCCATAACTGCATTAGCCAGGCGGTGAACGGCAGCCAGTTTCTGCCGCTGACCGGCCTGC

AGGTGCTGGATCTGAGCCATAACAAACTGGATCTGTATCATGAACATAGCTTTACCGAACTGC
```

```
CGCGCCTGGAAGCGCTGGATCTGAGCTATAACAGCCAGCCGTTTGGCATGCAGGGCGTGGCC

ATAACTTTAGCTTTGTGGCGCATCTGCGCACCCTGCGCCATCTGAGCCTGGCGCATAACAACA

TTCATAGCCAGGTGAGCCAGCAGCTGTGCAGCACCAGCCTGCGCGCGCTGGATTTTAGCGGCA

ACGCGCTGGGCCATATGTGGGCGGAAGGCGATCTGTATCTGCATTTTTTTCAGGGCCTGAGCG

GCCTGATTTGGCTGGATCTGAGCCAGAACCGCCTGCATACCCTGCTGCCGCAGACCCTGCGCA

ACCTGCCGAAAAGCCTGCAGGTGCTGCGCCTGCGCGATAACTATCTGGCGTTTTTTAAATGGT

GGAGCCTGCATTTTCTGCCGAAACTGGAAGTGCTGGATCTGGCGGGCAACCAGCTGAAAGCGC

TGACCAACGGCAGCCTGCCGGCGGGCACCCGCCTGCGCCGCCTGGATGTGAGCTGCAACAGCA

TTAGCTTTGTGGCGCCGGGCTTTTTTAGCAAAGCGAAAGAACTGCGCGAACTGAACCTGAGCG

CGAACGCGCTGAAAACCGTGGATCATAGCTGGTTTGGCCCGCTGGCGAGCGCGCTGCAGATTC

TGGATGTGAGCGCGAACCCGCTGCATTGCGCGTGCGGCGCGGCGTTTATGGATTTTCTGCTGG

AAGTGCAGGCGGCGGTGCCGGGCCTGCCGAGCCGCGTGAAATGCGGCAGCCCGGGCCAGCTGC

AGGGCCTGAGCATTTTTGCGCAGGATCTGCGCCTGTGCCTGGATGAAGCGCTGAGCTGGGATT

GCTTTGCGCTGAGCCTGCTGGCGGTGGCGCTGGGCCTGGGCGTGCCGATGCTGCATCATCTGT

GCGGCTGGGATCTGTGGTATTGCTTTCATCTGTGCCTGGCGTGGCTGCCGTGGCGCGGCCGCC

AGAGCGGCCGCGATGAAGATGCGCTGCCGTATGATGCGTTTGTGGTGTTTGATAAAACCCAGA

GCGCGGTGGCGGATTGGGTGTATAACGAACTGCGCGGCCAGCTGGAAGAATGCCGCGGCCGCT

GGGCGCTGCGCCTGTGCCTGGAAGAACGCGATTGGCTGCCGGGCAAAACCCTGTTTGAAAACC

TGTGGGCGAGCGTGTATGGCAGCCGCAAAACCCTGTTTGTGCTGGCGCATACCGATCGCGTGA

GCGGCCTGCTGCGCGCGAGCTTTCTGCTGGCGCAGCAGCGCCTGCTGGAAGATCGCAAAGATG

TGGTGGTGCTGGTGATTCTGAGCCCGGATGGCCGCCGCAGCCGCTATGTGCGCCTGCGCCAGC

GCCTGTGCCGCCAGAGCGTGCTGCTGTGGCCGCATCAGCCGAGCGGCCAGCGCAGCTTTTGGG

CGCAGCTGGGCATGGCGCTGACCCGCGATAACCATCATTTTTATAACCGCAACTTTTGCCAGG

GCCCGACCGCGGAAGGGCGGATCAGGCGGATCACCCAAATCTTGTGACAAAACTCACACATGC

CCACCGTGCCCAGCACCTGAACTCCTGGGGGACCGTCAGTCTTCCTCTTCCCCCCAAACCC

AAGGACACCCTCATGATCTCCCGGACCCCTGAGGTCACATGCGTGGTGGTGGACGTGAGCCAC

GAAGACCCTGAGGTCAAGTTCAACTGGTACGTGGACGGCGTGGAGGTGCATAATGCCAAGACA

AAGCCGCGGGAGGAGCAGTACAACAGCACGTACCGTGTGGTCAGCGTCCTCACCGTCCTGCAC

CAGGACTGGCTGAATGGCAAGGAGTACAAGTGCAAGGTCTCCAACAAAGCCCTCCCAGCCCCC

ATCGAGAAAACCATCTCCAAAGCCAAAGGGCAGCCCCGAGAACCACAGGTGTACACCCTGCCC

CCATCCCGGGAGGAGATGACCAAGAACCAGGTCAGCCTGACCTGCCTGGTCAAAGGCTTCTAT

CCCAGCGACATCGCCGTGGAGTGGGAGAGCAATGGGCAGCCGGAGAACAACTACAAGACCACG

CCTCCCGTGCTGGACTCCGACGGCTCCTTCTTCCTCTACAGCAAGCTCACCGTGGACAAGAGC

AGGTGGCAGCAGGGGAACGTCTTCTCATGCTCCGTGATGCATGAGGCTCTGCACAACCACTAC

ACGCAGAAGAGCCTCTCCCTGTCTCCGGGTAAATAG3'
SEQ ID NO. 5 (mRNA expression cassette No. 5 - NGF-Fc):
5'ATGAGGGGCATGAAGCTGCTGGGGGCGCTGCTGGCACTGGCGGCCCTACTGCAGGGGGCCG

TGTCCATGAGCATGCTGTTTTATACCCTGATTACCGCGTTTCTGATTGGCATTCAGGCGGAAC

CGCATAGCGAAAGCAACGTGCCGGCGGGCCATACCATTCCGCAGGCGCATTGGACCAAACTGC

AGCATAGCCTGGATACCGCGCTGCGCCGCGCGCGCAGCGCGCCGGCGGCGGCGATTGCGGCGC

GCGTGGCGGGCCAGACCCGCAACATTACCGTGGATCCGCGCCTGTTTAAAAAACGCCGCCTGC
```

-continued

GCAGCCCGCGCGTGCTGTTTAGCACCCAGCCGCCGCGCGAAGCGGCGGATACCCAGGATCTGG

ATTTTGAAGTGGGCGGCGCGGCGCCGTTTAACCGCACCCATCGCAGCAAACGCAGCAGCAGCC

ATCCGATTTTTCATCGCGGCGAATTTAGCGTGTGCGATAGCGTGAGCGTGTGGGTGGGCGATA

AAACCACCGCGACCGATATTAAAGGCAAAGAAGTGATGGTGCTGGGCGAAGTGAACATTAACA

ACAGCGTGTTTAAACAGTATTTTTTTGAAACCAAATGCCGCGATCCGAACCCGGTGGATAGCG

GCTGCCGCGGCATTGATAGCAAACATTGGAACAGCTATTGCACCACCACCCATACCTTTGTGA

AAGCGCTGACCATGGATGGCAAACAGGCGGCGTGGCGCTTTATTCGCATTGATACCGCGTGCG

TGTGCGTGCTGAGCCGAAAGCGGTGCGCCGCGCGGGCGGATCAGGCGGATCACCCAAATCTT

GTGACAAAACTCACACATGCCCACCGTGCCCAGCACCTGAACTCCTGGGGGACCGTCAGTCT

TCCTCTTCCCCCCAAAACCCAAGGACACCCTCATGATCTCCCGGACCCCTGAGGTCACATGCG

TGGTGGTGGACGTGAGCCACGAAGACCCTGAGGTCAAGTTCAACTGGTACGTGGACGGCGTGG

AGGTGCATAATGCCAAGACAAAGCCGCGGGAGGAGCAGTACAACAGCACGTACCGTGTGGTCA

GCGTCCTCACCGTCCTGCACCAGGACTGGCTGAATGGCAAGGAGTACAAGTGCAAGGTCTCCA

ACAAAGCCCTCCCAGCCCCCATCGAGAAAACCATCTCCAAAGCCAAAGGGCAGCCCCGAGAAC

CACAGGTGTACACCCTGCCCCCATCCCGGGAGGAGATGACCAAGAACCAGGTCAGCCTGACCT

GCCTGGTCAAAGGCTTCTATCCCAGCGACATCGCCGTGGAGTGGGAGAGCAATGGGCAGCCGG

AGAACAACTACAAGACCACGCCTCCCGTGCTGGACTCCGACGGCTCCTTCTTCCTCTACAGCA

AGCTCACCGTGGACAAGAGCAGGTGGCAGCAGGGGAACGTCTTCTCATGCTCCGTGATGCATG

AGGCTCTGCACAACCACTACACGCAGAAGAGCCTCTCCCTGTCTCCGGGTAAATAG3'

SEQ ID NO. 6 (mRNA expression cassette No. 6 - insulin-Fc):
5'ATGAGGGGCATGAAGCTGCTGGGGGCGCTGCTGGCACTGGCGGCCCTACTGCAGGGGCCG

TGTCCATGGCGCTGTGGATGCGCCTGCTGCCGCTGCTGGCGCTGCTGGCGCTGTGGGCCCGG

ATCCGGCGGCGGCGTTTGTGAACCAGCATCTGTGCGGCAGCCATCTGGTGGAAGCGCTGTATC

TGGTGTGCGGCGAACGCGGCTTTTTTTATACCCCGAAAACCCGCCGCGAAGCGGAAGATCTGC

AGGTGGGCCAGGTGGAACTGGGCGGCGGCCCGGGCGCGGGCAGCCTGCAGCCGCTGGCGCTGG

AAGGCAGCCTGCAGAAACGCGGCATTGTGGAACAGTGCTGCACCAGCATTTGCAGCCTGTATC

AGCTGGAAAACTATTGCAACGGGCGGATCAGGCGGATCACCCAAATCTTGTGACAAAACTCAC

ACATGCCCACCGTGCCCAGCACCTGAACTCCTGGGGGACCGTCAGTCTTCCTCTTCCCCCCA

AAACCCAAGGACACCCTCATGATCTCCCGGACCCCTGAGGTCACATGCGTGGTGGTGGACGTG

AGCCACGAAGACCCTGAGGTCAAGTTCAACTGGTACGTGGACGGCGTGGAGGTGCATAATGCC

AAGACAAAGCCGCGGGAGGAGCAGTACAACAGCACGTACCGTGTGGTCAGCGTCCTCACCGTC

CTGCACCAGGACTGGCTGAATGGCAAGGAGTACAAGTGCAAGGTCTCCAACAAAGCCCTCCCA

GCCCCCATCGAGAAAACCATCTCCAAAGCCAAAGGGCAGCCCCGAGAACCACAGGTGTACACC

CTGCCCCCATCCCGGGAGGAGATGACCAAGAACCAGGTCAGCCTGACCTGCCTGGTCAAAGGC

TTCTATCCCAGCGACATCGCCGTGGAGTGGGAGAGCAATGGGCAGCCGGAGAACAACTACAAG

ACCACGCCTCCCGTGCTGGACTCCGACGGCTCCTTCTTCCTCTACAGCAAGCTCACCGTGGAC

AAGAGCAGGTGGCAGCAGGGGAACGTCTTCTCATGCTCCGTGATGCATGAGGCTCTGCACAAC

CACTACACGCAGAAGAGCCTCTCCCTGTCTCCGGGTAAATAG3'

SEQ ID NO: 7 = SEQ ID NO: 1 + SEQ ID NO: 2
5'TTCTAGAATAATCAACCTCTGGATTACAAAATTTGTGAAAGATTGACTGGTATTCTTAACT

ATGTTGCTCCTTTTACGCTATGTGGATACGCTGCTTTAATGCCTTTGTATCATGCTATTGCTT

-continued

```
CCCGTATGGCTTTCATTTTCTCCTCCTTGTATAAATCCTGGTTGCTGTCTCTTTATGAGGAGT
TGTGGCCCGTTGTCAGGCAACGTGGCGTGGTGTGCACTGTGTTTGCTGACGCAACCCCCACTG
GTTGGGGCATTGCCACCACCTGTCAGCTCCTTTCCGGGACTTTCGCTTTCCCCCTCCCTATTG
CCACGGCGGAACTCATCGCCGCCTGCCTTGCCCGCTGCTGGACAGGGGCTCGGCTGTTGGGCA
CTGACAATTCCGTGGTGTTGTCGGGGAAATCATCGTCCTTTCCTTGGCTGCTCGCCTGTGTTG
CCACCTGGATTCTGCGCGGGACGTCCTTCTGCTACGTCCCTTCGGCCCTCAATCCAGCGGACC
TTCCTTCCCGCGGCCTGCTGCCGGCTCTGCGGCCTCTTCCGCGTCTTCGCCTTCGCCCTCAGA
CGAGTCGGATCTCCCTTTGGGCCGCCTCCCCGCCTAAGCTTATCGATACCGTCGAGATCTAAC
TTGTTTATTGCAGCTTATAATGGTTACAAATAAAGCAATAGCATCACAAATTTCACAAATAAA
GCATTTTTTCACTGCATTCTAGTTGTGGTTTGTCCAAACTCATCAATGTATCTTATCATGTC
TGGATCTCGACCTCGACTAGAGCATGGCTACGTAGATAAGTAGCATGGCGGGTTAATCATTAA
CTACAAGGAACCCCTAGTGATGGAGTTGGCCACTCCCTCTCTGCGCGCTCGCTCGCTCACTGA
GGCCGGGCGACCAAAGGTCGCCCGACGCCCGGGCTTTGCCCGGGCGGCCTCAGTGAGCGAGCG
AGCGCGCCAGCTGGCGTAATAGCGAAGAGGCCCGCACCGATCGCCCTTCCCAACAGTTGCGCA
GCCTGAATGGCGAATGGAATTCCAGACGATTGAGCGTCAAAATGTAGGTATTTCCATGAGCGT
TTTTCCTGTTGCAATGGCTGGCGGTAATATTGTTCTGGATATTACCAGCAAGGCCGATAGTTT
GAGTTCTTCTACTCAGGCAAGTGATGTTATTACTAATCAAAGAAGTATTGCGACAACGGTTAA
TTTGCGTGATGGACAGACTCTTTTACTCGGTGGCCTCACTGATTATAAAAACACTTCTCAGGA
TTCTGGCGTACCGTTCCTGTCTAAAATCCCTTTAATCGGCCTCCTGTTTAGCTCCCGCTCTGA
TTCTAACGAGGAAAGCACGTTATACGTGCTCGTCAAAGCAACCATAGTACGCGCCCTGTAGCG
GCGCATTAAGCGCGGCGGGTGTGGTGGTTACGCGCAGCGTGACCGCTACACTTGCCAGCGCCC
TAGCGCCCGCTCCTTTCGCTTTCTTCCCTTCCTTTCTCGCCACGTTCGCCGGCTTTCCCCGTC
AAGCTCTAAATCGGGGGCTCCCTTTAGGGTTCCGATTTAGTGCTTTACGGCACCTCGACCCCA
AAAAACTTGATTAGGGTGATGGTTCACGTAGTGGGCCATCGCCCTGATAGACGGTTTTTCGCC
CTTTGACGTTGGAGTCCACGTTCTTTAATAGTGGACTCTTGTTCCAAACTGGAACAACACTCA
ACCCTATCTCGGTCTATTCTTTTGATTTATAAGGGATTTTGCCGATTTCGGCCTATTGGTTAA
AAAATGAGCTGATTTAACAAAAATTTAACGCGAATTTTAACAAAATATTAACGTTTACAATTT
AAATATTTGCTTATACAATCTTCCTGTTTTTGGGGCTTTTCTGATTATCAACCGGGGTACATA
TGATTGACATGCTAGTTTTACGATTACCGTTCATCGATTCTCTTGTTTGCTCCAGACTCTCAG
GCAATGACCTGATAGCCTTTGTAGAGACCTCTCAAAAATAGCTACCCTCTCCGGCATGAATTT
ATCAGCTAGAACGGTTGAATATCATATTGATGGTGATTTGACTGTCTCCGGCCTTTCTCACCC
GTTTGAATCTTTACCTACACATTACTCAGGCATTGCATTTAAAATATATGAGGGTTCTAAAAA
TTTTTATCCTTGCGTTGAAATAAAGGCTTCTCCCGCAAAAGTATTACAGGGTCATAATGTTTT
TGGTACAACCGATTTAGCTTTATGCTCTGAGGCTTTATTGCTTAATTTTGCTAATTCTTTGCC
TTGCCTGTATGATTTATTGGATGTTGGAATTCCTGATGCGGTATTTTCTCCTTACGCATCTGT
GCGGTATTTCACACCGCATATGGTGCACTCTCAGTACAATCTGCTCTGATGCCGCATAGTTAA
GCCAGCCCCGACACCCGCCAACACCCGCTGACGCGCCCTGACGGGCTTGTCTGCTCCCGGCAT
CCGCTTACAGACAAGCTGTGACCGTCTCCGGGAGCTGCATGTGTCAGAGGTTTTCACCGTCAT
CACCGAAACGCGCGAGACGAAAGGGCCTCGTGATACGCCTATTTTTATAGGTTAATGTCATGA
TAATAATGGTTTCTTAGACGTCAGGTGGCACTTTTCGGGGAAATGTGCGCGGAACCCCTATTT
GTTTATTTTTCTAAATACATTCAAATATGTATCCGCTCATGAGACAATAACCCTGATAAATGC
```

-continued

```
TTCAATAATATTGAAAAAGGAAGAGTATGAGTATTCAACATTTCCGTGTCGCCCTTATTCCCT

TTTTTGCGGCATTTTGCCTTCCTGTTTTTGCTCACCCAGAAACGCTGGTGAAAGTAAAAGATG

CTGAAGATCAGTTGGGTGCACGAGTGGGTTACATCGAACTGGATCTCAACAGCGGTAAGATCC

TTGAGAGTTTTCGCCCCGAAGAACGTTTTCCAATGATGAGCACTTTTAAAGTTCTGCTATGTG

GCGCGGTATTATCCCGTATTGACGCCGGGCAAGAGCAACTCGGTCGCCGCATACACTATTCTC

AGAATGACTTGGTTGAGTACTCACCAGTCACAGAAAAGCATCTTACGGATGGCATGACAGTAA

GAGAATTATGCAGTGCTGCCATAACCATGAGTGATAACACTGCGGCCAACTTACTTCTGACAA

CGATCGGAGGACCGAAGGAGCTAACCGCTTTTTTGCACAACATGGGGGATCATGTAACTCGCC

TTGATCGTTGGGAACCGGAGCTGAATGAAGCCATACCAAACGACGAGCGTGACACCACGATGC

CTGTAGCAATGGCAACAACGTTGCGCAAACTATTAACTGGCGAACTACTTACTCTAGCTTCCC

GGCAACAATTAATAGACTGGATGGAGGCGGATAAAGTTGCAGGACCACTTCTGCGCTCGGCCC

TTCCGGCTGGCTGGTTTATTGCTGATAAATCTGGAGCCGGTGAGCGTGGGTCTCGCGGTATCA

TTGCAGCACTGGGGCCAGATGGTAAGCCCTCCCGTATCGTAGTTATCTACACGACGGGGAGTC

AGGCAACTATGGATGAACGAAATAGACAGATCGCTGAGATAGGTGCCTCACTGATTAAGCATT

GGTAACTGTCAGACCAAGTTTACTCATATATACTTTAGATTGATTTAAAACTTCATTTTTAAT

TTAAAAGGATCTAGGTGAAGATCCTTTTTGATAATCTCATGACCAAAATCCCTTAACGTGAGT

TTTCGTTCCACTGAGCGTCAGACCCCGTAGAAAAGATCAAAGGATCTTCTTGAGATCCTTTTT

TTCTGCGCGTAATCTGCTGCTTGCAAACAAAAAAACCACCGCTACCAGCGGTGGTTTGTTTGC

CGGATCAAGAGCTACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCTGTAGCACCGCCTA

CATACCTCGCTCTGCTAATCCTGTTACCAGTGGCTGCTGCCAGTGGCGATAAGTCGTGTCTTA

CCGGGTTGGACTCAAGACGATAGTTACCGGATAAGGCGCAGCGGTCGGGCTGAACGGGGGGTT

CGTGCACACAGCCCAGCTTGGAGCGAACGACCTACACCGAACTGAGATACCTACAGCGTGAGC

TATGAGAAAGCGCCACGCTTCCCGAAGGGAGAAAGGCGGACAGGTATCCGGTAAGCGGCAGGG

TCGGAACAGGAGAGCGCACGAGGGAGCTTCCAGGGGGAAACGCCTGGTATCTTTATAGTCCTG

TCGGGTTTCGCCACCTCTGACTTGAGCGTCGATTTTTGTGATGCTCGTCAGGGGGGCGGAGCC

TATGGAAAAACGCCAGCAACGCGGCCTTTTTACGGTTCCTGGCCTTTTGCTGGCCTTTTGCTC

ACATGTTCTTTCCTGCGTTATCCCCTGATTCTGTGGATAACCGTATTACCGCCTTTGAGTGAG

CTGATACCGCTCGCCGCAGCCGAACGACCGAGCGCAGCGAGTCAGTGAGCGAGGAAGCGGAAG

AGCGCCCAATACGCAAACCGCCTCTCCCCGCGCGTTGGCCGATTCATTAATGCAGCAGCTGCG

CGCTCGCTCGCTCACTGAGGCCGCCCGGGCAAAGCCCGGGCGTCGGGCGACCTTTGGTCGCCC

GGCCTCAGTGAGCGAGCGAGCGCGCAGAGAGGGAGTGGCCAACTCCATCACTAGGGGTTCCTT

GTAGTTAATGATTAACCCGCCATGCTACTTATCTACGTAGCCATGCTCTAGGACATTGATTAT

TGACTAGTGGAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAGGGACTTTC

CATTGACGTCAATGGGTGGAGTATTTACGGTAAACTGCCCACTTGGCAGTACATCAAGTGTAT

CATATGCCAAGTACGCCCCCTATTGACGTCAATGACGGTAAATGGCCCGCCTGGCATTATGCC

CAGTACATGACCTTATGGGACTTTCCTACTTGGCAGTACATCTACGTATTAGTCATCGCTATT

ACCATGGTCGAGGTGAGCCCCACGTTCTGCTTCACTCTCCCCATCTCCCCCCCCTCCCCACCC

CCAATTTTGTATTTATTTATTTTTTAATTATTTTGTGCAGCGATGGGGGCGGGGGGGGGGGGG
```

```
GGCGCGCGCCAGGCGGGGGGGGGGGCGAGGGGCGGGGCGGGGCGAGGCGGAGAGGTGCGGC

GGCAGCCAATCAGAGCGGCGCGCTCCGAAAGTTTCCTTTTATGGCGAGGCGGCGGCGGCGG

GCCCTATAAAAAGCGAAGCGCGCGGCGGGCGGGAGTCGCTGCGCGCTGCCTTCGCCCCGTGCC

CCGCTCCGCCGCCGCCTCGCGCCGCCCGCCCCGGCTCTGACTGACCGCGTTACTAAAACAGGT

AAGTCCGGCCTCCGCGCCGGGTTTTGGCGCCTCCCGCGGGCGCCCCCCTCCTCACGGCGAGCG

CTGCCACGTCAGACGAAGGGCGCAGCGAGCGTCCTGATCCTTCCGCCCGGACGCTCAGGACAG

CGGCCCGCTGCTCATAAGACTCGGCCTTAGAACCCCAGTATCAGCAGAAGGACATTTTAGGAC

GGGACTTGGGTGACTCTAGGGCACTGGTTTTCTTTCCAGAGAGCGGAACAGGCGAGGAAAAGT

AGTCCCTTCTCGGCGATTCTGCGGAGGGATCTCCGTGGGCGGTGAACGCCGATGATGCCTCT

ACTAACCATGTTCATGTTTTCTTTTTTTTTCTACAGGTCCTGGGTGACGAACAGGGTACCGCC

ACCATGAGGGGCATGAAGCTGCTGGGGGCGCTGCTGGCACTGGCGGCCCTACTGCAGGGGGCC

GTGTCCCTGAAGATCGCAGCCTTCAACATCCAGACATTTGGGGAGACCAAGATGTCCAATGCC

ACCCTCGTCAGCTACATTGTGCAGATCCTGAGCCGCTATGACATCGCCCTGGTCCAGGAGGTC

AGAGACAGCCACCTGACTGCCGTGGGGAAGCTGCTGGACAACCTCAATCAGGATGCACCAGAC

ACCTATCACTACGTGGTCAGTGAGCCACTGGGACGGAACAGCTATAAGGAGCGCTACCTGTTC

GTGTACAGGCCTGACCAGGTGTCTGCGGTGGACAGCTACTACTACGATGATGGCTGCGAGCCC

TGCGGGAACGACACCTTCAACCGAGAGCCAGCCATTGTCAGGTTCTTCTCCCGGTTCACAGAG

GTCAGGGAGTTTGCCATTGTTCCCCTGCATGCGGCCCCGGGGGACGCAGTAGCCGAGATCGAC

GCTCTCTATGACGTCTACCTGGATGTCCAAGAGAAATGGGGCTTGGAGGACGTCATGTTGATG

GGCGACTTCAATGCGGGCTGCAGCTATGTGAGACCCTCCCAGTGGTCATCCATCCGCCTGTGG

ACAAGCCCCACCTTCCAGTGGCTGATCCCCGACAGCGCTGACACCACAGCTACACCCACGCAC

TGTGCCTATGACAGGATCGTGGTTGCAGGGATGCTGCTCCGAGGCGCCGTTGTTCCCGACTCG

GCTCTTCCCTTTAACTTCCAGGCTGCCTATGGCCTGAGTGACCAACTGGCCCAAGCCATCAGT

GACCACTATCCAGTGGAGGTGATGCTGAAGGGCGGATCAGGCGGATCACCCAAATCTTGTGAC

AAAACTCACACATGCCCACCGTGCCCAGCACCTGAACTCCTGGGGGGACCGTCAGTCTTCCTC

TTCCCCCCAAAACCCAAGGACACCCTCATGATCTCCCGGACCCCTGAGGTCACATGCGTGGTG

GTGGACGTGAGCCACGAAGACCCTGAGGTCAAGTTCAACTGGTACGTGGACGGCGTGGAGGTG

CATAATGCCAAGACAAAGCCGCGGGAGGAGCAGTACAACAGCACGTACCGTGTGGTCAGCGTC

CTCACCGTCCTGCACCAGGACTGGCTGAATGGCAAGGAGTACAAGTGCAAGGTCTCCAACAAA

GCCCTCCCAGCCCCCATCGAGAAAACCATCTCCAAAGCCAAAGGGCAGCCCCGAGAACCACAG

GTGTACACCCTGCCCCCATCCCGGGAGGAGATGACCAAGAACCAGGTCAGCCTGACCTGCCTG

GTCAAAGGCTTCTATCCCAGCGACATCGCCGTGGAGTGGGAGAGCAATGGGCAGCCGGAGAAC

AACTACAAGACCACGCCTCCCGTGCTGGACTCCGACGGCTCCTTCTTCCTCTACAGCAAGCTC

ACCGTGGACAAGAGCAGGTGGCAGCAGGGGAACGTCTTCTCATGCTCCGTGATGCATGAGGCT

CTGCACAACCACTACACGCAGAAGAGCCTCTCCCTGTCTCCGGGTAAATAG3'

SEQ ID NO: 8 = SEQ ID NO: 1 + SEQ ID NO: 3
5'TTCTAGAATAATCAACCTCTGGATTACAAAATTTGTGAAAGATTGACTGGTATTCTTAACT

ATGTTGCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAGGAGT

TGTGGCCCGTTGTCAGGCAACGTGGCGTGGTGTGCACTGTGTTTGCTGACGCAACCCCCACTG

GTTGGGGCATTGCCACCACCTGTCAGCTCCTTTCCGGGACTTTCGCTTTCCCCCTCCCTATTG
```

-continued

```
CCACGGCGGAACTCATCGCCGCCTGCCTTGCCCGCTGCTGGACAGGGGCTCGGCTGTTGGCA

CTGACAATTCCGTGGTGTTGTCGGGGAAATCATCGTCCTTTCCTTGGCTGCTCGCCTGTGTTG

CCACCTGGATTCTGCGCGGGACGTCCTTCTGCTACGTCCCTTCGGCCCTCAATCCAGCGGACC

TTCCTTCCCGCGGCCTGCTGCCGGCTCTGCGGCCTCTTCCGCGTCTTCGCCTTCGCCCTCAGA

CGAGTCGGATCTCCCTTTGGGCCGCCTCCCCGCCTAAGCTTATCGATACCGTCGAGATCTAAC

TTGTTTATTGCAGCTTATAATGGTTACAAATAAAGCAATAGCATCACAAATTTCACAAATAAA

GCATTTTTTCACTGCATTCTAGTTGTGGTTTGTCCAAACTCATCAATGTATCTTATCATGTC

TGGATCTCGACCTCGACTAGAGCATGGCTACGTAGATAAGTAGCATGGCGGGTTAATCATTAA

CTACAAGGAACCCCTAGTGATGGAGTTGGCCACTCCCTCTCTGCGCGCTCGCTCGCTCACTGA

GGCCGGGCGACCAAAGGTCGCCCGACGCCCGGGCTTTGCCCGGGCGGCCTCAGTGAGCGAGCG

AGCGCGCCAGCTGGCGTAATAGCGAAGAGGCCCGCACCGATCGCCCTTCCCAACAGTTGCGCA

GCCTGAATGGCGAATGGAATTCCAGACGATTGAGCGTCAAAATGTAGGTATTTCCATGAGCGT

TTTTCCTGTTGCAATGGCTGGCGGTAATATTGTTCTGGATATTACCAGCAAGGCCGATAGTTT

GAGTTCTTCTACTCAGGCAAGTGATGTTATTACTAATCAAAGAAGTATTGCGACAACGGTTAA

TTTGCGTGATGGACAGACTCTTTTACTCGGTGGCCTCACTGATTATAAAAACACTTCTCAGGA

TTCTGGCGTACCGTTCCTGTCTAAAATCCCTTTAATCGGCCTCCTGTTTAGCTCCCGCTCTGA

TTCTAACGAGGAAAGCACGTTATACGTGCTCGTCAAAGCAACCATAGTACGCGCCCTGTAGCG

GCGCATTAAGCGCGGCGGGTGTGGTGGTTACGCGCAGCGTGACCGCTACACTTGCCAGCGCCC

TAGCGCCCGCTCCTTTCGCTTTCTTCCCTTCCTTTCTCGCCACGTTCGCCGGCTTTCCCCGTC

AAGCTCTAAATCGGGGGCTCCCTTTAGGGTTCCGATTTAGTGCTTTACGGCACCTCGACCCCA

AAAAACTTGATTAGGGTGATGGTTCACGTAGTGGGCCATCGCCCTGATAGACGGTTTTTCGCC

CTTTGACGTTGGAGTCCACGTTCTTTAATAGTGGACTCTTGTTCCAAACTGGAACAACACTCA

ACCCTATCTCGGTCTATTCTTTTGATTTATAAGGGATTTTGCCGATTTCGGCCTATTGGTTAA

AAAATGAGCTGATTTAACAAAAATTTAACGCGAATTTTAACAAAATATTAACGTTTACAATTT

AAATATTTGCTTATACAATCTTCCTGTTTTTGGGGCTTTTCTGATTATCAACCGGGGTACATA

TGATTGACATGCTAGTTTTACGATTACCGTTCATCGATTCTCTTGTTTGCTCCAGACTCTCAG

GCAATGACCTGATAGCCTTTGTAGAGACCTCTCAAAAATAGCTACCCTCTCCGGCATGAATTT

ATCAGCTAGAACGGTTGAATATCATATTGATGGTGATTTGACTGTCTCCGGCCTTTCTCACCC

GTTTGAATCTTTACCTACACATTACTCAGGCATTGCATTTAAAATATATGAGGGTTCTAAAAA

TTTTTATCCTTGCGTTGAAATAAAGGCTTCTCCCGCAAAAGTATTACAGGGTCATAATGTTTT

TGGTACAACCGATTTAGCTTTATGCTCTGAGGCTTTATTGCTTAATTTTGCTAATTCTTTGCC

TTGCCTGTATGATTTATTGGATGTTGGAATTCCTGATGCGGTATTTTCTCCTTACGCATCTGT

GCGGTATTTCACACCGCATATGGTGCACTCTCAGTACAATCTGCTCTGATGCCGCATAGTTAA

GCCAGCCCCGACACCCGCCAACACCCGCTGACGCGCCCTGACGGGCTTGTCTGCTCCCGGCAT

CCGCTTACAGACAAGCTGTGACCGTCTCCGGGAGCTGCATGTGTCAGAGGTTTTCACCGTCAT

CACCGAAACGCGCGAGACGAAAGGGCCTCGTGATACGCCTATTTTTATAGGTTAATGTCATGA

TAATAATGGTTTCTTAGACGTCAGGTGGCACTTTTCGGGGAAATGTGCGCGGAACCCCTATTT

GTTTATTTTTCTAAATACATTCAAATATGTATCCGCTCATGAGACAATAACCCTGATAAATGC

TTCAATAATATTGAAAAAGGAAGAGTATGAGTATTCAACATTTCCGTGTCGCCCTTATTCCCT

TTTTTGCGGCATTTTGCCTTCCTGTTTTTGCTCACCCAGAAACGCTGGTGAAAGTAAAAGATG

CTGAAGATCAGTTGGGTGCACGAGTGGGTTACATCGAACTGGATCTCAACAGCGGTAAGATCC
```

-continued

```
TTGAGAGTTTTCGCCCCGAAGAACGTTTTCCAATGATGAGCACTTTTAAAGTTCTGCTATGTG

GCGCGGTATTATCCCGTATTGACGCCGGGCAAGAGCAACTCGGTCGCCGCATACACTATTCTC

AGAATGACTTGGTTGAGTACTCACCAGTCACAGAAAAGCATCTTACGGATGGCATGACAGTAA

GAGAATTATGCAGTGCTGCCATAACCATGAGTGATAACACTGCGGCCAACTTACTTCTGACAA

CGATCGGAGGACCGAAGGAGCTAACCGCTTTTTTGCACAACATGGGGGATCATGTAACTCGCC

TTGATCGTTGGGAACCGGAGCTGAATGAAGCCATACCAAACGACGAGCGTGACACCACGATGC

CTGTAGCAATGGCAACAACGTTGCGCAAACTATTAACTGGCGAACTACTTACTCTAGCTTCCC

GGCAACAATTAATAGACTGGATGGAGGCGGATAAAGTTGCAGGACCACTTCTGCGCTCGGCCC

TTCCGGCTGGCTGGTTTATTGCTGATAAATCTGGAGCCGGTGAGCGTGGGTCTCGCGGTATCA

TTGCAGCACTGGGGCCAGATGGTAAGCCCTCCCGTATCGTAGTTATCTACACGACGGGGAGTC

AGGCAACTATGGATGAACGAAATAGACAGATCGCTGAGATAGGTGCCTCACTGATTAAGCATT

GGTAACTGTCAGACCAAGTTTACTCATATATACTTTAGATTGATTTAAAACTTCATTTTTAAT

TTAAAAGGATCTAGGTGAAGATCCTTTTTGATAATCTCATGACCAAAATCCCTTAACGTGAGT

TTTCGTTCCACTGAGCGTCAGACCCCGTAGAAAAGATCAAAGGATCTTCTTGAGATCCTTTTT

TTCTGCGCGTAATCTGCTGCTTGCAAACAAAAAAACCACCGCTACCAGCGGTGGTTTGTTTGC

CGGATCAAGAGCTACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCTGTAGCACCGCCTA

CATACCTCGCTCTGCTAATCCTGTTACCAGTGGCTGCTGCCAGTGGCGATAAGTCGTGTCTTA

CCGGGTTGGACTCAAGACGATAGTTACCGGATAAGGCGCAGCGGTCGGGCTGAACGGGGGGTT

CGTGCACACAGCCCAGCTTGGAGCGAACGACCTACACCGAACTGAGATACCTACAGCGTGAGC

TATGAGAAAGCGCCACGCTTCCCGAAGGGAGAAAGGCGGACAGGTATCCGGTAAGCGGCAGGG

TCGGAACAGGAGAGCGCACGAGGGAGCTTCCAGGGGGAAACGCCTGGTATCTTTATAGTCCTG

TCGGGTTTCGCCACCTCTGACTTGAGCGTCGATTTTTGTGATGCTCGTCAGGGGGCGGAGCC

TATGGAAAAACGCCAGCAACGCGGCCTTTTTACGGTTCCTGGCCTTTTGCTGGCCTTTTGCTC

ACATGTTCTTTCCTGCGTTATCCCCTGATTCTGTGGATAACCGTATTACCGCCTTTGAGTGAG

CTGATACCGCTCGCCGCAGCCGAACGACCGAGCGCAGCGAGTCAGTGAGCGAGGAAGCGGAAG

AGCGCCCAATACGCAAACCGCCTCTCCCCGCGCGTTGGCCGATTCATTAATGCAGCAGCTGCG

CGCTCGCTCGCTCACTGAGGCCGCCCGGGCAAAGCCCGGGCGTCGGGCGACCTTTGGTCGCCC

GGCCTCAGTGAGCGAGCGAGCGCGCAGAGAGGGAGTGGCCAACTCCATCACTAGGGGTTCCTT

GTAGTTAATGATTAACCCGCCATGCTACTTATCTACGTAGCCATGCTCTAGGACATTGATTAT

TGACTAGTGGAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAGGGACTTTC

CATTGACGTCAATGGGTGGAGTATTTACGGTAAACTGCCCACTTGGCAGTACATCAAGTGTAT

CATATGCCAAGTACGCCCCCTATTGACGTCAATGACGGTAAATGGCCCGCCTGGCATTATGCC

CAGTACATGACCTTATGGGACTTTCCTACTTGGCAGTACATCTACGTATTAGTCATCGCTATT

ACCATGGTCGAGGTGAGCCCCACGTTCTGCTTCACTCTCCCCATCTCCCCCCCTCCCCACCC

CCAATTTTGTATTTATTTATTTTTAATTATTTTGTGCAGCGATGGGGGCGGGGGGGGGGGGG

GGCGCGCGCCAGGCGGGGCGGGGGGGGCGAGGGGCGGGCGGGGCGAGGCGGAGAGGTGCGG

CGGCAGCCAATCAGAGCGGCGCGCTCCGAAAGTTTCCTTTTATGGCGAGGCGGCGGCGGCGGC

GGCCCTATAAAAAGCGAAGCGCGCGGCGGGCGGGAGTCGCTGCGCGCTGCCTTCGCCCCGTGC
```

-continued

```
CCCGCTCCGCCGCCGCCTCGCGCCGCCCGCCCCGGCTCTGACTGACCGCGTTACTAAAACAGG
TAAGTCCGGCCTCCGCGCCGGGTTTTGGCGCCTCCCGCGGGCGCCCCCCTCCTCACGGCGAGC
GCTGCCACGTCAGACGAAGGGCGCAGCGAGCGTCCTGATCCTTCCGCCCGGACGCTCAGGACA
GCGGCCCGCTGCTCATAAGACTCGGCCTTAGAACCCCAGTATCAGCAGAAGGACATTTTAGGA
CGGGACTTGGGTGACTCTAGGGCACTGGTTTTCTTTCCAGAGAGCGGAACAGGCGAGGAAAAG
TAGTCCCTTCTCGGCGATTCTGCGGAGGGATCTCCGTGGGGCGGTGAACGCCGATGATGCCTC
TACTAACCATGTTCATGTTTTCTTTTTTTTCTACAGGTCCTGGGTGACGAACAGGGTACCGC
CACCGCCAGACCCTGCCGTGCATTTATTTTTGGGGCGGCCTGCTGCCGTTTGGCATGCTGTGC
GCGAGCAGCACCACCAAATGCACCGTGAGCCATGAAGTGGCGGATTGCAGCCATCTGAAACTG
ACCCAGGTGCCGGATGATCTGCCGACCAACATTACCGTGCTGAACCTGACCCATAACCAGCTG
CGCCGCCTGCCGGCGGCGAACTTTACCCGCTATAGCCAGCTGACCAGCCTGGATGTGGGCTTT
AACACCATTAGCAAACTGGAACCGGAACTGTGCCAGAAACTGCCGATGCTGAAAGTGCTGAAC
CTGCAGCATAACGAACTGAGCCAGCTGAGCGATAAAACCTTTGCGTTTTGCACCAACCTGACC
GAACTGCATCTGATGAGCAACAGCATTCAGAAAATTAAAAACAACCCGTTTGTGAAACAGAAA
AACCTGATTACCCTGGATCTGAGCCATAACGGCCTGAGCAGCACCAAACTGGGCACCCAGGTG
CAGCTGGAAAACCTGCAGGAACTGCTGCTGAGCAACAACAAAATTCAGGCGCTGAAAAGCGAA
GAACTGGATATTTTTGCGAACAGCAGCCTGAAAAAACTGGAACTGAGCAGCAACCAGATTAAA
GAATTTAGCCCGGGCTGCTTTCATGCGATTGGCCGCCTGTTTGGCCTGTTTCTGAACAACGTG
CAGCTGGGCCCGAGCCTGACCGAAAAACTGTGCCTGGAACTGGCGAACACCAGCATTCGCAAC
CTGAGCCTGAGCAACAGCCAGCTGAGCACCACCAGCAACACCACCTTTCTGGGCCTGAAATGG
ACCAACCTGACCATGCTGGATCTGAGCTATAACAACCTGAACGTGGTGGGCAACGATAGCTTT
GCGTGGCTGCCGCAGCTGGAATATTTTTTCTGGAATATAACAACATTCAGCATCTGTTTAGC
CATAGCCTGCATGGCCTGTTTAACGTGCGCTATCTGAACCTGAAACGCAGCTTTACCAAACAG
AGCATTAGCCTGGCGAGCCTGCCGAAAATTGATGATTTTAGCTTTCAGTGGCTGAAATGCCTG
GAACATCTGAACATGGAAGATAACGATATTCCGGGCATTAAAAGCAACATGTTTACCGGCCTG
ATTAACCTGAAATATCTGAGCCTGAGCAACAGCTTTACCAGCCTGCGCACCCTGACCAACGAA
ACCTTTGTGAGCCTGGCGCATAGCCCGCTGCATATTCTGAACCTGACCAAAAACAAAATTAGC
AAAATTGAAAGCGATGCGTTTAGCTGGCTGGGCCATCTGGAAGTGCTGGATCTGGGCCTGAAC
GAAATTGGCCAGGAACTGACCGGCCAGGAATGGCGCGGCCTGGAAAACATTTTTGAAATTTAT
CTGAGCTATAACAAATATCTGCAGCTGACCCGCAACAGCTTTGCGCTGGTGCCGAGCCTGCAG
CGCCTGATGCTGCGCCGCGTGGCGCTGAAAAACGTGGATAGCAGCCCGAGCCCGTTTCAGCCG
CTGCGCAACCTGACCATTCTGGATCTGAGCAACAACAACATTGCGAACATTAACGATGATATG
CTGGAAGGCCTGGAAAAACTGGAAATTCTGGATCTGCAGCATAACAACCTGGCGCGCCTGTGG
AAACATGCGAACCCGGGCGGCCCGATTTATTTTCTGAAAGGCCTGAGCCATCTGCATATTCTG
AACCTGGAAAGCAACGGCTTTGATGAAATTCCGGTGGAAGTGTTTAAAGATCTGTTTGAACTG
AAAATTATTGATCTGGGCCTGAACAACCTGAACACCCTGCCGGCGAGCGTGTTTAACAACCAG
GTGAGCCTGAAAAGCCTGAACCTGCAGAAAAAACCTGATTACCAGCGTGGAAAAAAAAGTGTTT
GGCCCGGCGTTTCGCAACCTGACCGAACTGGATATGCGCTTTAACCCGTTTGATTGCACCTGC
GAAAGCATTGCGTGGTTTGTGAACTGGATTAACGAAACCCATACCAACATTCCGGAACTGAGC
AGCCATTATCTGTGCAACACCCCGCCGCATTATCATGGCTTTCCGGTGCGCCTGTTTGATACC
AGCAGCTGCAAAGATAGCGCGCCGTTTGAACTGTTTTTTATGATTAACACCAGCATTCTGCTG
```

-continued

ATTTTTATTTTTATTGTGCTGCTGATTCATTTTGAAGGCTGGCGCATTAGCTTTTATTGGAAC

GTGAGCGTGCATCGCGTGCTGGGCTTTAAAGAAATTGATCGCCAGACCGAACAGTTTGAATAT

GCGGCGTATATTATTCATGCGTATAAAGATAAAGATTGGGTGTGGGAACATTTTAGCAGCATG

GAAAAAGAAGATCAGAGCCTGAAATTTTGCCTGGAAGAACGCGATTTTGAAGCGGGCGTGTTT

GAACTGGAAGCGATTGTGAACAGCATTAAACGCAGCCGCAAAATTATTTTTGTGATTACCCAT

CATCTGCTGAAAGATCCGCTGTGCAAACGCTTTAAAGTGCATCATGCGGTGCAGCAGGCGATT

GAACAGAACCTGGATAGCATTATTCTGGTGTTTCTGGAAGAAATTCCGGATTATAAACTGAAC

CATGCGCTGTGCCTGCGCCGCGGCATGTTTAAAAGCCATTGCATTCTGAACTGGCCGGTGCAG

AAAGAACGCATTGGCGCGTTTCGCCATAAACTGCAGGTGGCGCTGGGCAGCAAAAACAGCGTG

CATGGGCGGATCAGGCGGATCACCCAAATCTTGTGACAAAACTCACACATGCCCACCGTGCCC

AGCACCTGAACTCCTGGGGGACCGTCAGTCTTCCTCTTCCCCCCAAAACCCAAGGACACCCT

CATGATCTCCCGGACCCCTGAGGTCACATGCGTGGTGGTGGACGTGAGCCACGAAGACCCTGA

GGTCAAGTTCAACTGGTACGTGGACGGCGTGGAGGTGCATAATGCCAAGACAAAGCCGCGGGA

GGAGCAGTACAACAGCACGTACCGTGTGGTCAGCGTCCTCACCGTCCTGCACCAGGACTGGCT

GAATGGCAAGGAGTACAAGTGCAAGGTCTCCAACAAAGCCCTCCCAGCCCCCATCGAGAAAAC

CATCTCCAAAGCCAAAGGGCAGCCCCGAGAACCACAGGTGTACACCCTGCCCCCATCCCGGGA

GGAGATGACCAAGAACCAGGTCAGCCTGACCTGCCTGGTCAAAGGCTTCTATCCCAGCGACAT

CGCCGTGGAGTGGGAGAGCAATGGGCAGCCGGAGAACAACTACAAGACCACGCCTCCCGTGCT

GGACTCCGACGGCTCCTTCTTCCTCTACAGCAAGCTCACCGTGGACAAGAGCAGGTGGCAGCA

GGGGAACGTCTTCTCATGCTCCGTGATGCATGAGGCTCTGCACAACCACTACACGCAGAAGAG

CCTCTCCCTGTCTCCGGGTAAATAG3'

SEQ ID NO: 9 = SEQ ID NO: 1 + SEQ ID NO: 4
5'TTCTAGAATAATCAACCTCTGGATTACAAAATTTGTGAAAGATTGACTGGTATTCTTAACT

ATGTTGCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAGGAGT

TGTGGCCCGTTGTCAGGCAACGTGGCGTGGTGTGCACTGTGTTTGCTGACGCAACCCCCACTG

GTTGGGGCATTGCCACCACCTGTCAGCTCCTTTCCGGGACTTTCGCTTTCCCCCTCCCTATTG

CCACGGCGGAACTCATCGCCGCCTGCCTTGCCCGCTGCTGGACAGGGGCTCGGCTGTTGGGCA

CTGACAATTCCGTGGTGTTGTCGGGGAAATCATCGTCCTTTCCTTGGCTGCTCGCCTGTGTTG

CCACCTGGATTCTGCGCGGGACGTCCTTCTGCTACGTCCCTTCGGCCCTCAATCCAGCGGACC

TTCCTTCCCGCGGCCTGCTGCCGGCTCTGCGGCCTCTTCCGCGTCTTCGCCTTCGCCCTCAGA

CGAGTCGGATCTCCCTTTGGGCCGCCTCCCCGCCTAAGCTTATCGATACCGTCGAGATCTAAC

TTGTTTATTGCAGCTTATAATGGTTACAAATAAAGCAATAGCATCACAAATTTCACAAATAAA

GCATTTTTTTCACTGCATTCTAGTTGTGGTTTGTCCAAACTCATCAATGTATCTTATCATGTC

TGGATCTCGACCTCGACTAGAGCATGGCTACGTAGATAAGTAGCATGGCGGGTTAATCATTAA

CTACAAGGAACCCCTAGTGATGGAGTTGGCCACTCCCTCTCTGCGCGCTCGCTCGCTCACTGA

GGCCGGGCGACCAAAGGTCGCCCGACGCCCGGGCTTTGCCCGGGCGGCCTCAGTGAGCGAGCG

AGCGCGCCAGCTGGCGTAATAGCGAAGAGGCCCGCACCGATCGCCCTTCCCAACAGTTGCGCA

GCCTGAATGGCGAATGGAATTCCAGACGATTGAGCGTCAAAATGTAGGTATTTCCATGAGCGT

TTTTCCTGTTGCAATGGCTGGCGGTAATATTGTTCTGGATATTACCAGCAAGGCCGATAGTTT

GAGTTCTTCTACTCAGGCAAGTGATGTTATTACTAATCAAAGAAGTATTGCGACAACGGTTAA

-continued

```
TTTGCGTGATGGACAGACTCTTTTACTCGGTGGCCTCACTGATTATAAAAACACTTCTCAGGA
TTCTGGCGTACCGTTCCTGTCTAAAATCCCTTTAATCGGCCTCCTGTTTAGCTCCCGCTCTGA
TTCTAACGAGGAAAGCACGTTATACGTGCTCGTCAAAGCAACCATAGTACGCGCCCTGTAGCG
GCGCATTAAGCGCGGCGGGTGTGGTGGTTACGCGCAGCGTGACCGCTACACTTGCCAGCGCCC
TAGCGCCCGCTCCTTTCGCTTTCTTCCCTTCCTTTCTCGCCACGTTCGCCGGCTTTCCCCGTC
AAGCTCTAAATCGGGGGCTCCCTTTAGGGTTCCGATTTAGTGCTTTACGGCACCTCGACCCCA
AAAAACTTGATTAGGGTGATGGTTCACGTAGTGGGCCATCGCCCTGATAGACGGTTTTTCGCC
CTTTGACGTTGGAGTCCACGTTCTTTAATAGTGGACTCTTGTTCCAAACTGGAACAACACTCA
ACCCTATCTCGGTCTATTCTTTTGATTTATAAGGGATTTTGCCGATTTCGGCCTATTGGTTAA
AAAATGAGCTGATTTAACAAAAATTTAACGCGAATTTTAACAAAATATTAACGTTTACAATTT
AAATATTTGCTTATACAATCTTCCTGTTTTTGGGCTTTTCTGATTATCAACCGGGGTACATA
TGATTGACATGCTAGTTTTACGATTACCGTTCATCGATTCTCTTGTTTGCTCCAGACTCTCAG
GCAATGACCTGATAGCCTTTGTAGAGACCTCTCAAAAATAGCTACCCTCTCCGGCATGAATTT
ATCAGCTAGAACGGTTAATATCATATTGATGGTGATTTGACTGTCTCCGGCCTTTCTCACCC
GTTTGAATCTTTACCTACACATTACTCAGGCATTGCATTTAAAATATATGAGGGTTCTAAAAA
TTTTTATCCTTGCGTTGAAATAAAGGCTTCTCCCGCAAAAGTATTACAGGGTCATAATGTTTT
TGGTACAACCGATTTAGCTTTATGCTCTGAGGCTTTATTGCTTAATTTTGCTAATTCTTTGCC
TTGCCTGTATGATTTATTGGATGTTGGAATTCCTGATGCGGTATTTTCTCCTTACGCATCTGT
GCGGTATTTCACACCGCATATGGTGCACTCTCAGTACAATCTGCTCTGATGCCGCATAGTTAA
GCCAGCCCCGACACCCGCCAACACCCGCTGACGCGCCCTGACGGGCTTGTCTGCTCCCGGCAT
CCGCTTACAGACAAGCTGTGACCGTCTCCGGGAGCTGCATGTGTCAGAGGTTTTCACCGTCAT
CACCGAAACGCGCGAGACGAAAGGGCCTCGTGATACGCCTATTTTTATAGGTTAATGTCATGA
TAATAATGGTTTCTTAGACGTCAGGTGGCACTTTTCGGGGAAATGTGCGCGGAACCCCTATTT
GTTTATTTTTCTAAATACATTCAAATATGTATCCGCTCATGAGACAATAACCCTGATAAATGC
TTCAATAATATTGAAAAAGGAAGAGTATGAGTATTCAACATTTCCGTGTCGCCCTTATTCCCT
TTTTTGCGGCATTTTGCCTTCCTGTTTTTGCTCACCCAGAAACGCTGGTGAAAGTAAAAGATG
CTGAAGATCAGTTGGGTGCACGAGTGGGTTACATCGAACTGGATCTCAACAGCGGTAAGATCC
TTGAGAGTTTTCGCCCCGAAGAACGTTTTCCAATGATGAGCACTTTTAAAGTTCTGCTATGTG
GCGCGGTATTATCCCGTATTGACGCCGGGCAAGAGCAACTCGGTCGCCGCATACACTATTCTC
AGAATGACTTGGTTGAGTACTCACCAGTCACAGAAAAGCATCTTACGGATGGCATGACAGTAA
GAGAATTATGCAGTGCTGCCATAACCATGAGTGATAACACTGCGGCCAACTTACTTCTGACAA
CGATCGGAGGACCGAAGGAGCTAACCGCTTTTTTGCACAACATGGGGATCATGTAACTCGCC
TTGATCGTTGGGAACCGGAGCTGAATGAAGCCATACCAAACGACGAGCGTGACACCACGATGC
CTGTAGCAATGGCAACAACGTTGCGCAAACTATTAACTGGCGAACTACTTACTCTAGCTTCCC
GGCAACAATTAATAGACTGGATGGAGGCGGATAAAGTTGCAGGACCACTTCTGCGCTCGGCCC
TTCCGGCTGGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGACGGGGAGTC
AGGCAACTATGGATGAACGAAATAGACAGATCGCTGAGATAGGTGCCTCACTGATTAAGCATT
GGTAACTGTCAGACCAAGTTTACTCATATATACTTTAGATTGATTTAAAACTTCATTTTTAAT
TTAAAAGGATCTAGGTGAAGATCCTTTTTGATAATCTCATGACCAAAATCCCTTAACGTGAGT
```

-continued

```
TTTCGTTCCACTGAGCGTCAGACCCCGTAGAAAAGATCAAAGGATCTTCTTGAGATCCTTTTT

TTCTGCGCGTAATCTGCTGCTTGCAAACAAAAAAACCACCGCTACCAGCGGTGGTTTGTTTGC

CGGATCAAGAGCTACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCTGTAGCACCGCCTA

CATACCTCGCTCTGCTAATCCTGTTACCAGTGGCTGCTGCCAGTGGCGATAAGTCGTGTCTTA

CCGGGTTGGACTCAAGACGATAGTTACCGGATAAGGCGCAGCGGTCGGGCTGAACGGGGGGTT

CGTGCACACAGCCCAGCTTGGAGCGAACGACCTACACCGAACTGAGATACCTACAGCGTGAGC

TATGAGAAAGCGCCACGCTTCCCGAAGGGAGAAAGGCGGACAGGTATCCGGTAAGCGGCAGGG

TCGGAACAGGAGAGCGCACGAGGGAGCTTCCAGGGGGAAACGCCTGGTATCTTTATAGTCCTG

TCGGGTTTCGCCACCTCTGACTTGAGCGTCGATTTTTGTGATGCTCGTCAGGGGGGCGGAGCC

TATGGAAAAACGCCAGCAACGCGGCCTTTTTACGGTTCCTGGCCTTTTGCTGGCCTTTTGCTC

ACATGTTCTTTCCTGCGTTATCCCCTGATTCTGTGGATAACCGTATTACCGCCTTTGAGTGAG

CTGATACCGCTCGCCGCAGCCGAACGACCGAGCGCAGCGAGTCAGTGAGCGAGGAAGCGGAAG

AGCGCCCAATACGCAAACCGCCTCTCCCCGCGCGTTGGCCGATTCATTAATGCAGCAGCTGCG

CGCTCGCTCGCTCACTGAGGCCGCCCGGGCAAAGCCCGGGCGTCGGGCGACCTTTGGTCGCCC

GGCCTCAGTGAGCGAGCGAGCGCGCAGAGAGGGAGTGGCCAACTCCATCACTAGGGGTTCCTT

GTAGTTAATGATTAACCCGCCATGCTACTTATCTACGTAGCCATGCTCTAGGACATTGATTAT

TGACTAGTGGAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAGGGACTTTC

CATTGACGTCAATGGGTGGAGTATTTACGGTAAACTGCCCACTTGGCAGTACATCAAGTGTAT

CATATGCCAAGTACGCCCCCTATTGACGTCAATGACGGTAAATGGCCCGCCTGGCATTATGCC

CAGTACATGACCTTATGGGACTTTCCTACTTGGCAGTACATCTACGTATTAGTCATCGCTATT

ACCATGGTCGAGGTGAGCCCCACGTTCTGCTTCACTCTCCCCATCTCCCCCCCCTCCCCACCC

CCAATTTTGTATTTATTTATTTTTTAATTATTTTGTGCAGCGATGGGGGCGGGGGGGGGGGG

GGCGCGCGCCAGGCGGGGGGGGCGGGGCGAGGGGCGGGGGGGCGAGGCGGAGAGGTGCGGCG

GCAGCCAATCAGAGCGGCGCGCTCCGAAAGTTTCCTTTTATGGCGAGGCGGCGGCGGCGGCGG

CCCTATAAAAAGCGAAGCGCGCGGCGGGCGGGAGTCGCTGCGCGCTGCCTTCGCCCCGTGCCC

CGCTCCGCCGCCGCCTCGCGCCGCCCGCCCCGGCTCTGACTGACCGCGTTACTAAAACAGGTA

AGTCCGGCCTCCGCGCCGGGTTTTGGCGCCTCCCGCGGGCGCCCCCTCCTCACGGCGAGCGC

TGCCACGTCAGACGAAGGGCGCAGCGAGCGTCCTGATCCTTCCGCCCGGACGCTCAGGACAGC

GGCCCGCTGCTCATAAGACTCGGCCTTAGAACCCCAGTATCAGCAGAAGGACATTTAGGACG

GGACTTGGGTGACTCTAGGGCACTGGTTTTCTTTCCAGAGAGCGGAACAGGCGAGGAAAAGTA

GTCCCTTCTCGGCGATTCTGCGGAGGGATCTCCGTGGGCGGTGAACGCCGATGATGCCTCTA

CTAACCATGTTCATGTTTTCTTTTTTTTCTACAGGTCCTGGGTGACGAACAGGGTACCGCCA

CCATGAGGGGCATGAAGCTGCTGGGGCGCTGCTGGCACTGGCGGCCCTACTGCAGGGGCCG

TGTCCATGGGCTTTTGCCGCAGCGCGCTGCATCCGCTGAGCCTGCTGGTGCAGGCGATTATGC

TGGCGATGACCCTGGCGCTGGGCACCCTGCCGGCGTTTCTGCCGTGCGAACTGCAGCCGCATG

GCCTGGTGAACTGCAACTGGCTGTTTCTGAAAAGCGTGCCGCATTTTAGCATGGCGGCGCCGC

GCGGCAACGTGACCAGCCTGAGCCTGAGCAGCAACCGCATTCATCATCTGCATGATAGCGATT

TTGCGCATCTGCCGAGCCTGCGCCATCTGAACCTGAAATGGAACTGCCCGCCGGTGGGCCTGA

GCCCGATGCATTTTCCGTGCCATATGACCATTGAACCGAGCACCTTTCTGGCGGTGCCGACCC
```

-continued

```
TGGAAGAACTGAACCTGAGCTATAACAACATTATGACCGTGCCGGCGCTGCCGAAAAGCCTGA

TTAGCCTGAGCCTGAGCCATACCAACATTCTGATGCTGGATAGCGCGAGCCTGGCGGGCCTGC

ATGCGCTGCGCTTTCTGTTTATGGATGGCAACTGCTATTATAAAAACCCGTGCCGCCAGGCGC

TGGAAGTGGCGCCGGGCGCGCTGCTGGGCCTGGGCAACCTGACCCATCTGAGCCTGAAATATA

ACAACCTGACCGTGGTGCCGCGCAACCTGCCGAGCAGCCTGGAATATCTGCTGCTGAGCTATA

ACCGCATTGTGAAACTGGCGCCGGAAGATCTGGCGAACCTGACCGCGCTGCGCGTGCTGGATG

TGGGCGGCAACTGCCGCCGCTGCGATCATGCGCCGAACCCGTGCATGGAATGCCCGCGCCATT

TTCCGCAGCTGCATCCGGATACCTTTAGCCATCTGAGCCGCCTGGAAGGCCTGGTGCTGAAAG

ATAGCAGCCTGAGCTGGCTGAACGCGAGCTGGTTTCGCGGCCTGGGCAACCTGCGCGTGCTGG

ATCTGAGCGAAAACTTTCTGTATAAATGCATTACCAAAACCAAAGCGTTTCAGGGCCTGACCC

AGCTGCGCAAACTGAACCTGAGCTTTAACTATCAGAAACGCGTGAGCTTTGCGCATCTGAGCC

TGGCGCCGAGCTTTGGCAGCCTGGTGGCGCTGAAAGAACTGGATATGCATGGCATTTTTTTTC

GCAGCCTGGATGAAACCACCCTGCGCCCGCTGGCGCGCCTGCCGATGCTGCAGACCCTGCGCC

TGCAGATGAACTTTATTAACCAGGCGCAGCTGGGCATTTTTCGCGCGTTTCCGGGCCTGCGCT

ATGTGGATCTGAGCGATAACCGCATTAGCGGCGCGAGCGAACTGACCGCGACCATGGGCGAAG

CGGATGGCGGCGAAAAAGTGTGGCTGCAGCCGGGCGATCTGGCGCCGGCGCCGGTGGATACCC

CGAGCAGCGAAGATTTTCGCCCGAACTGCAGCACCCTGAACTTTACCCTGGATCTGAGCCGCA

ACAACCTGGTGACCGTGCAGCCGGAAATGTTTGCGCAGCTGAGCCATCTGCAGTGCCTGCGCC

TGAGCCATAACTGCATTAGCCAGGCGGTGAACGGCAGCCAGTTTCTGCCGCTGACCGGCCTGC

AGGTGCTGGATCTGAGCCATAACAAACTGGATCTGTATCATGAACATAGCTTTACCGAACTGC

CGCGCCTGGAAGCGCTGGATCTGAGCTATAACAGCCAGCCGTTTGGCATGCAGGGCGTGGGCC

ATAACTTTAGCTTTGTGGCGCATCTGCGCACCCTGCGCCATCTGAGCCTGGCGCATAACAACA

TTCATAGCCAGGTGAGCCAGCAGCTGTGCAGCACCAGCCTGCGCGCGCTGGATTTTAGCGGCA

ACGCGCTGGGCCATATGTGGGCGGAAGGCGATCTGTATCTGCATTTTTTTCAGGGCCTGAGCG

GCCTGATTTGGCTGGATCTGAGCCAGAACCGCCTGCATACCCTGCTGCCGCAGACCCTGCGCA

ACCTGCCGAAAAGCCTGCAGGTGCTGCGCCTGCGCGATAACTATCTGGCGTTTTTTAAATGGT

GGAGCCTGCATTTTCTGCCGAAACTGGAAGTGCTGGATCTGGCGGGCAACCAGCTGAAAGCGC

TGACCAACGGCAGCCTGCCGGCGGGCACCCGCCTGCGCCGCCTGGATGTGAGCTGCAACAGCA

TTAGCTTTGTGGCGCCGGGCTTTTTTAGCAAAGCGAAAGAACTGCGCGAACTGAACCTGAGCG

CGAACGCGCTGAAAACCGTGGATCATAGCTGGTTTGGCCCGCTGGCGAGCGCGCTGCAGATTC

TGGATGTGAGCGCGAACCCGCTGCATTGCGCGTGCGGCGCGGCGTTTATGGATTTTCTGCTGG

AAGTGCAGGCGGCGGTGCCGGGCCTGCCGAGCCGCGTGAAATGCGGCAGCCCGGGCCAGCTGC

AGGGCCTGAGCATTTTTGCGCAGGATCTGCGCCTGTGCCTGGATGAAGCGCTGAGCTGGATT

GCTTTGCGCTGAGCCTGCTGGCGGTGGCGCTGGGCCTGGGCGTGCCGATGCTGCATCATCTGT

GCGGCTGGGATCTGTGGTATTGCTTTCATCTGTGCCTGGCGTGGCTGCCGTGGCGCGGCCGCC

AGAGCGGCCGCGATGAAGATGCGCTGCCGTATGATGCGTTTGTGGTGTTTGATAAAACCCAGA

GCGCGGTGGCGGATTGGGTGTATAACGAACTGCGCGGCCAGCTGGAAGAATGCCGCGGCCGCT

GGGCGCTGCGCCTGTGCCTGGAAGAACGCGATTGGCTGCCGGGCAAAACCCTGTTTGAAAACC

TGTGGGCGAGCGTGTATGGCAGCCGCAAAACCCTGTTTGTGCTGGCGCATACCGATCGCGTGA

GCGGCCTGCTGCGCGCGAGCTTTCTGCTGGCGCAGCAGCGCCTGCTGGAAGATCGCAAAGATG
```

-continued
TGGTGGTGCTGGTGATTCTGAGCCCGGATGGCCGCCGCAGCCGCTATGTGCGCCTGCGCCAGC

GCCTGTGCCGCCAGAGCGTGCTGCTGTGGCCGCATCAGCCGAGCGGCCAGCGCAGCTTTTGGG

CGCAGCTGGGCATGGCGCTGACCCGCGATAACCATCATTTTTATAACCGCAACTTTTGCCAGG

GCCCGACCGCGGAAGGGCGGATCAGGCGGATCACCCAAATCTTGTGACAAAACTCACACATGC

CCACCGTGCCCAGCACCTGAACTCCTGGGGGACCGTCAGTCTTCCTCTTCCCCCCAAAACCC

AAGGACACCCTCATGATCTCCCGGACCCCTGAGGTCACATGCGTGGTGGTGGACGTGAGCCAC

GAAGACCCTGAGGTCAAGTTCAACTGGTACGTGGACGGCGTGGAGGTGCATAATGCCAAGACA

AAGCCGCGGGAGGAGCAGTACAACAGCACGTACCGTGTGGTCAGCGTCCTCACCGTCCTGCAC

CAGGACTGGCTGAATGGCAAGGAGTACAAGTGCAAGGTCTCCAACAAAGCCCTCCCAGCCCCC

ATCGAGAAAACCATCTCCAAAGCCAAAGGGCAGCCCCGAGAACCACAGGTGTACACCCTGCCC

CCATCCCGGGAGGAGATGACCAAGAACCAGGTCAGCCTGACCTGCCTGGTCAAAGGCTTCTAT

CCCAGCGACATCGCCGTGGAGTGGGAGAGCAATGGGCAGCCGGAGAACAACTACAAGACCACG

CCTCCCGTGCTGGACTCCGACGGCTCCTTCTTCCTCTACAGCAAGCTCACCGTGGACAAGAGC

AGGTGGCAGCAGGGGAACGTCTTCTCATGCTCCGTGATGCATGAGGCTCTGCACAACCACTAC

ACGCAGAAGAGCCTCTCCCTGTCTCCGGGTAAATAG3'

SEQ ID NO: 10 = SEQ ID NO: 1 + SEQ ID NO: 5
5'TTCTAGAATAATCAACCTCTGGATTACAAAATTTGTGAAAGATTGACTGGTATTCTTAACT

ATGTTGCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAGGAGT

TGTGGCCCGTTGTCAGGCAACGTGGCGTGGTGTGCACTGTGTTTGCTGACGCAACCCCCACTG

GTTGGGGCATTGCCACCACCTGTCAGCTCCTTTCCGGGACTTTCGCTTTCCCCCTCCCTATTG

CCACGGCGGAACTCATCGCCGCCTGCCTTGCCCGCTGCTGGACAGGGGCTCGGCTGTTGGGCA

CTGACAATTCCGTGGTGTTGTCGGGGAAATCATCGTCCTTTCCTTGGCTGCTCGCCTGTGTTG

CCACCTGGATTCTGCGCGGGACGTCCTTCTGCTACGTCCCTTCGGCCCTCAATCCAGCGGACC

TTCCTTCCCGCGGCCTGCTGCCGGCTCTGCGGCCTCTTCCGCGTCTTCGCCTTCGCCCTCAGA

CGAGTCGGATCTCCCTTTGGGCCGCCTCCCCGCCTAAGCTTATCGATACCGTCGAGATCTAAC

TTGTTTATTGCAGCTTATAATGGTTACAAATAAAGCAATAGCATCACAAATTTCACAAATAAA

GCATTTTTTCACTGCATTCTAGTTGTGGTTTGTCCAAACTCATCAATGTATCTTATCATGTC

TGGATCTCGACCTCGACTAGAGCATGGCTACGTAGATAAGTAGCATGGCGGGTTAATCATTAA

CTACAAGGAACCCCTAGTGATGGAGTTGGCCACTCCCTCTCTGCGCGCTCGCTCGCTCACTGA

GGCCGGGCGACCAAAGGTCGCCCGACGCCCGGGCTTTGCCCGGGCGGCCTCAGTGAGCGAGCG

AGCGCGCCAGCTGGCGTAATAGCGAAGAGGCCCGCACCGATCGCCCTTCCCAACAGTTGCGCA

GCCTGAATGGCGAATGGAATTCCAGACGATTGAGCGTCAAAATGTAGGTATTTCCATGAGCGT

TTTTCCTGTTGCAATGGCTGGCGGTAATATTGTTCTGGATATTACCAGCAAGGCCGATAGTTT

GAGTTCTTCTACTCAGGCAAGTGATGTTATTACTAATCAAAGAAGTATTGCGACAACGGTTAA

TTTGCGTGATGGACAGACTCTTTTACTCGGTGGCCTCACTGATTATAAAAACACTTCTCAGGA

TTCTGGCGTACCGTTCCTGTCTAAAATCCCTTTAATCGGCCTCCTGTTTAGCTCCCGCTCTGA

TTCTAACGAGGAAAGCACGTTATACGTGCTCGTCAAAGCAACCATAGTACGCGCCCTGTAGCG

GCGCATTAAGCGCGGCGGGTGTGGTGGTTACGCGCAGCGTGACCGCTACACTTGCCAGCGCCC

TAGCGCCCGCTCCTTTCGCTTTCTTCCCTTCCTTTCTCGCCACGTTCGCCGGCTTTCCCCGTC

AAGCTCTAAATCGGGGGCTCCCTTTAGGGTTCCGATTTAGTGCTTTACGGCACCTCGACCCCA

-continued

```
AAAAACTTGATTAGGGTGATGGTTCACGTAGTGGGCCATCGCCCTGATAGACGGTTTTTCGCC
CTTTGACGTTGGAGTCCACGTTCTTTAATAGTGGACTCTTGTTCCAAACTGGAACAACACTCA
ACCCTATCTCGGTCTATTCTTTTGATTTATAAGGGATTTTGCCGATTTCGGCCTATTGGTTAA
AAAATGAGCTGATTTAACAAAAATTTAACGCGAATTTTAACAAAATATTAACGTTTACAATTT
AAATATTTGCTTATACAATCTTCCTGTTTTTGGGGCTTTTCTGATTATCAACCGGGGTACATA
TGATTGACATGCTAGTTTTACGATTACCGTTCATCGATTCTCTTGTTTGCTCCAGACTCTCAG
GCAATGACCTGATAGCCTTTGTAGAGACCTCTCAAAAATAGCTACCCTCTCCGGCATGAATTT
ATCAGCTAGAACGGTTGAATATCATATTGATGGTGATTTGACTGTCTCCGGCCTTTCTCACCC
GTTTGAATCTTTACCTACACATTACTCAGGCATTGCATTTAAAATATATGAGGGTTCTAAAAA
TTTTTATCCTTGCGTTGAAATAAAGGCTTCTCCCGCAAAAGTATTACAGGGTCATAATGTTTT
TGGTACAACCGATTTAGCTTTATGCTCTGAGGCTTTATTGCTTAATTTTGCTAATTCTTTGCC
TTGCCTGTATGATTTATTGGATGTTGGAATTCCTGATGCGGTATTTTCTCCTTACGCATCTGT
GCGGTATTTCACACCGCATATGGTGCACTCTCAGTACAATCTGCTCTGATGCCGCATAGTTAA
GCCAGCCCCGACACCCGCCAACACCCGCTGACGCGCCCTGACGGGCTTGTCTGCTCCCGGCAT
CCGCTTACAGACAAGCTGTGACCGTCTCCGGGAGCTGCATGTGTCAGAGGTTTTCACCGTCAT
CACCGAAACGCGCGAGACGAAAGGGCCTCGTGATACGCCTATTTTTATAGGTTAATGTCATGA
TAATAATGGTTTCTTAGACGTCAGGTGGCACTTTTCGGGGAAATGTGCGCGGAACCCCTATTT
GTTTATTTTTCTAAATACATTCAAATATGTATCCGCTCATGAGACAATAACCCTGATAAATGC
TTCAATAATATTGAAAAAGGAAGAGTATGAGTATTCAACATTTCCGTGTCGCCCTTATTCCCT
TTTTTGCGGCATTTTGCCTTCCTGTTTTTGCTCACCCAGAAACGCTGGTGAAAGTAAAAGATG
CTGAAGATCAGTTGGGTGCACGAGTGGGTTACATCGAACTGGATCTCAACAGCGGTAAGATCC
TTGAGAGTTTTCGCCCCGAAGAACGTTTTCCAATGATGAGCACTTTTAAAGTTCTGCTATGTG
GCGCGGTATTATCCCGTATTGACGCCGGGCAAGAGCAACTCGGTCGCCGCATACACTATTCTC
AGAATGACTTGGTTGAGTACTCACCAGTCACAGAAAAGCATCTTACGGATGGCATGACAGTAA
GAGAATTATGCAGTGCTGCCATAACCATGAGTGATAACACTGCGGCCAACTTACTTCTGACAA
CGATCGGAGGACCGAAGGAGCTAACCGCTTTTTTGCACAACATGGGGGATCATGTAACTCGCC
TTGATCGTTGGGAACCGGAGCTGAATGAAGCCATACCAAACGACGAGCGTGACACCACGATGC
CTGTAGCAATGGCAACAACGTTGCGCAAACTATTAACTGGCGAACTACTTACTCTAGCTTCCC
GGCAACAATTAATAGACTGGATGGAGGCGGATAAAGTTGCAGGACCACTTCTGCGCTCGGCCC
TTCCGGCTGGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGACGGGGAGTC
AGGCAACTATGGATGAACGAAATAGACAGATCGCTGAGATAGGTGCCTCACTGATTAAGCATT
GGTAACTGTCAGACCAAGTTTACTCATATATACTTTAGATTGATTTAAAACTTCATTTTTAAT
TTAAAAGGATCTAGGTGAAGATCCTTTTTGATAATCTCATGACCAAAATCCCTTAACGTGAGT
TTTCGTTCCACTGAGCGTCAGACCCCGTAGAAAAGATCAAAGGATCTTCTTGAGATCCTTTTT
TTCTGCGCGTAATCTGCTGCTTGCAAACAAAAAAACCACCGCTACCAGCGGTGGTTTGTTTGC
CGGATCAAGAGCTACCAACTCTTTTTCCGAAGGTAACTGGCTTCAGCAGAGCGCAGATACCAA
ATACTGTCCTTCTAGTGTAGCCGTAGTTAGGCCACCACTTCAAGAACTCTGTAGCACCGCCTA
CATACCTCGCTCTGCTAATCCTGTTACCAGTGGCTGCTGCCAGTGGCGATAAGTCGTGTCTTA
CCGGGTTGGACTCAAGACGATAGTTACCGGATAAGGCGCAGCGGTCGGGCTGAACGGGGGGTT
CGTGCACACAGCCCAGCTTGGAGCGAACGACCTACACCGAACTGAGATACCTACAGCGTGAGC
```

```
TATGAGAAAGCGCCACGCTTCCCGAAGGGAGAAAGGCGGACAGGTATCCGGTAAGCGGCAGGG

TCGGAACAGGAGAGCGCACGAGGGAGCTTCCAGGGGGAAACGCCTGGTATCTTTATAGTCCTG

TCGGGTTTCGCCACCTCTGACTTGAGCGTCGATTTTTGTGATGCTCGTCAGGGGGGCGGAGCC

TATGGAAAAACGCCAGCAACGCGGCCTTTTTACGGTTCCTGGCCTTTTGCTGGCCTTTTGCTC

ACATGTTCTTTCCTGCGTTATCCCCTGATTCTGTGGATAACCGTATTACCGCCTTTGAGTGAG

CTGATACCGCTCGCCGCAGCCGAACGACCGAGCGCAGCGAGTCAGTGAGCGAGGAAGCGGAAG

AGCGCCCAATACGCAAACCGCCTCTCCCCGCGCGTTGGCCGATTCATTAATGCAGCAGCTGCG

CGCTCGCTCGCTCACTGAGGCCGCCCGGGCAAAGCCCGGGCGTCGGGCGACCTTTGGTCGCCC

GGCCTCAGTGAGCGAGCGAGCGCGCAGAGAGGGAGTGGCCAACTCCATCACTAGGGGTTCCTT

GTAGTTAATGATTAACCCGCCATGCTACTTATCTACGTAGCCATGCTCTAGGACATTGATTAT

TGACTAGTGGAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAGGGACTTTC

CATTGACGTCAATGGGTGGAGTATTTACGGTAAACTGCCCACTTGGCAGTACATCAAGTGTAT

CATATGCCAAGTACGCCCCCTATTGACGTCAATGACGGTAAATGGCCCGCCTGGCATTATGCC

CAGTACATGACCTTATGGGACTTTCCTACTTGGCAGTACATCTACGTATTAGTCATCGCTATT

ACCATGGTCGAGGTGAGCCCCACGTTCTGCTTCACTCTCCCCATCTCCCCCCCCTCCCCACCC

CCAATTTTGTATTTATTTATTTTTTAATTATTTTGTGCAGCGATGGGGGCGGGGGGGGGGGG

GGCGCGCGCCAGGCGGGGGGGGGGGGCGAGGGGCGGGGGGGCGAGGCGGAGAGGTGCGGCG

GCAGCCAATCAGAGCGGCGCGCTCCGAAAGTTTCCTTTTATGGCGAGGCGGCGGCGGCGGCGG

CCCTATAAAAAGCGAAGCGCGCGGCGGGCGGGAGTCGCTGCGCGCTGCCTTCGCCCCGTGCCC

CGCTCCGCCGCCGCCTCGCGCCGCCCGCCCCGGCTCTGACTGACCGCGTTACTAAAACAGGTA

AGTCCGGCCTCCGCGCCGGGTTTTGGCGCCTCCCGCGGGCGCCCCCCTCCTCACGGCGAGCGC

TGCCACGTCAGACGAAGGGCGCAGCGAGCGTCCTGATCCTTCCGCCCGGACGCTCAGGACAGC

GGCCCGCTGCTCATAAGACTCGGCCTTAGAACCCCAGTATCAGCAGAAGGACATTTTAGGACG

GGACTTGGGTGACTCTAGGGCACTGGTTTTCTTTCCAGAGAGCGGAACAGGCGAGGAAAAGTA

GTCCCTTCTCGGCGATTCTGCGGAGGGATCTCCGTGGGGCGGTGAACGCCGATGATGCCTCTA

CTAACCATGTTCATGTTTTCTTTTTTTTCTACAGGTCCTGGGTGACGAACAGGGTACCGCCA

CCATGAGGGGCATGAAGCTGCTGGGGGCGCTGCTGGCACTGGCGGCCCTACTGCAGGGGCCG

TGTCCATGAGCATGCTGTTTTATACCCTGATTACCGCGTTTCTGATTGGCATTCAGGCGGAAC

CGCATAGCGAAAGCAACGTGCCGGCGGGCCATACCATTCCGCAGGCGCATTGGACCAAACTGC

AGCATAGCCTGGATACCGCGCTGCGCCGCGCGCGCAGCGCGCCGGCGGCGGCGATTGCGGCGC

GCGTGGCGGGCCAGACCCGCAACATTACCGTGGATCCGCGCCTGTTTAAAAAACGCCGCCTGC

GCAGCCCGCGCGTGCTGTTTAGCACCCAGCCGCCGCGCGAAGCGGCGGATACCCAGGATCTGG

ATTTTGAAGTGGGCGGCGCGGCGCCGTTTAACCGCACCCATCGCAGCAAACGCAGCAGCAGCC

ATCCGATTTTTCATCGCGGCGAATTTAGCGTGTGCGATAGCGTGAGCGTGTGGGTGGGCGATA

AAACCACCGCGACCGATATTAAAGGCAAAGAAGTGATGGTGCTGGGCGAAGTGAACATTAACA

ACAGCGTGTTTAAACAGTATTTTTTTGAAACCAAATGCCGCGATCCGAACCCGGTGGATAGCG

GCTGCCGCGGCATTGATAGCAAACATTGGAACAGCTATTGCACCACCACCCATACCTTTGTGA

AAGCGCTGACCATGGATGGCAAACAGGCGGCGTGGCGCTTTATTCGCATTGATACCGCGTGCG

TGTGCGTGCTGAGCCGCAAAGCGGTGCGCCGCGCGGGCGGATCAGGCGGATCACCCAAATCTT
```

-continued

```
GTGACAAAACTCACACATGCCCACCGTGCCCAGCACCTGAACTCCTGGGGGACCGTCAGTCT

TCCTCTTCCCCCCAAAACCCAAGGACACCCTCATGATCTCCCGGACCCCTGAGGTCACATGCG

TGGTGGTGGACGTGAGCCACGAAGACCCTGAGGTCAAGTTCAACTGGTACGTGGACGGCGTGG

AGGTGCATAATGCCAAGACAAAGCCGCGGGAGGAGCAGTACAACAGCACGTACCGTGTGGTCA

GCGTCCTCACCGTCCTGCACCAGGACTGGCTGAATGGCAAGGAGTACAAGTGCAAGGTCTCCA

ACAAAGCCCTCCCAGCCCCCATCGAGAAAACCATCTCCAAAGCCAAAGGGCAGCCCCGAGAAC

CACAGGTGTACACCCTGCCCCCATCCCGGGAGGAGATGACCAAGAACCAGGTCAGCCTGACCT

GCCTGGTCAAAGGCTTCTATCCCAGCGACATCGCCGTGGAGTGGGAGAGCAATGGGCAGCCGG

AGAACAACTACAAGACCACGCCTCCCGTGCTGGACTCCGACGGCTCCTTCTTCCTCTACAGCA

AGCTCACCGTGGACAAGAGCAGGTGGCAGCAGGGGAACGTCTTCTCATGCTCCGTGATGCATG

AGGCTCTGCACAACCACTACACGCAGAAGAGCCTCTCCCTGTCTCCGGGTAAATAG3'

SEQ ID NO: 11 = SEQ ID NO: 1 + SEQ ID NO: 6
5'TTCTAGAATAATCAACCTCTGGATTACAAAATTTGTGAAAGATTGACTGGTATTCTTAACT

ATGTTGCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAGGAGT

TGTGGCCCGTTGTCAGGCAACGTGGCGTGGTGTGCACTGTGTTTGCTGACGCAACCCCCACTG

GTTGGGGCATTGCCACCACCTGTCAGCTCCTTTCCGGGACTTTCGCTTTCCCCCTCCCTATTG

CCACGGCGGAACTCATCGCCGCCTGCCTTGCCCGCTGCTGGACAGGGGCTCGGCTGTTGGGCA

CTGACAATTCCGTGGTGTTGTCGGGGAAATCATCGTCCTTTCCTTGGCTGCTCGCCTGTGTTG

CCACCTGGATTCTGCGCGGGACGTCCTTCTGCTACGTCCCTTCGGCCCTCAATCCAGCGGACC

TTCCTTCCCGCGGCCTGCTGCCGGCTCTGCGGCCTCTTCCGCGTCTTCGCCTTCGCCCTCAGA

CGAGTCGGATCTCCCTTTGGGCCGCCTCCCCGCCTAAGCTTATCGATACCGTCGAGATCTAAC

TTGTTTATTGCAGCTTATAATGGTTACAAATAAAGCAATAGCATCACAAATTTCACAAATAAA

GCATTTTTTTCACTGCATTCTAGTTGTGGTTTGTCCAAACTCATCAATGTATCTTATCATGTC

TGGATCTCGACCTCGACTAGAGCATGGCTACGTAGATAAGTAGCATGGCGGGTTAATCATTAA

CTACAAGGAACCCCTAGTGATGGAGTTGGCCACTCCCTCTCTGCGCGCTCGCTCGCTCACTGA

GGCCGGGCGACCAAAGGTCGCCCGACGCCCGGGCTTTGCCCGGGCGGCCTCAGTGAGCGAGCG

AGCGCGCCAGCTGGCGTAATAGCGAAGAGGCCCGCACCGATCGCCCTTCCCAACAGTTGCGCA

GCCTGAATGGCGAATGGAATTCCAGACGATTGAGCGTCAAAATGTAGGTATTTCCATGAGCGT

TTTTCCTGTTGCAATGGCTGGCGGTAATATTGTTCTGGATATTACCAGCAAGGCCGATAGTTT

GAGTTCTTCTACTCAGGCAAGTGATGTTATTACTAATCAAAGAAGTATTGCGACAACGGTTAA

TTTGCGTGATGGACAGACTCTTTTACTCGGTGGCCTCACTGATTATAAAAACACTTCTCAGGA

TTCTGGCGTACCGTTCCTGTCTAAAATCCCTTTAATCGGCCTCCTGTTTAGCTCCCGCTCTGA

TTCTAACGAGGAAAGCACGTTATACGTGCTCGTCAAAGCAACCATAGTACGCGCCCTGTAGCG

GCGCATTAAGCGCGGCGGGTGTGGTGGTTACGCGCAGCGTGACCGCTACACTTGCCAGCGCCC

TAGCGCCCGCTCCTTTCGCTTTCTTCCCTTCCTTTCTCGCCACGTTCGCCGGCTTTCCCCGTC

AAGCTCTAAATCGGGGGCTCCCTTTAGGGTTCCGATTTAGTGCTTTACGGCACCTCGACCCCA

AAAAACTTGATTAGGGTGATGGTTCACGTAGTGGGCCATCGCCCTGATAGACGGTTTTTCGCC

CTTTGACGTTGGAGTCCACGTTCTTTAATAGTGGACTCTTGTTCCAAACTGGAACAACACTCA

ACCCTATCTCGGTCTATTCTTTTGATTTATAAGGGATTTTGCCGATTTCGGCCTATTGGTTAA

AAAATGAGCTGATTTAACAAAAATTTAACGCGAATTTTAACAAAATATTAACGTTTACAATTT
```

```
AAATATTTGCTTATACAATCTTCCTGTTTTTGGGGCTTTTCTGATTATCAACCGGGGTACATA

TGATTGACATGCTAGTTTTACGATTACCGTTCATCGATTCTCTTGTTTGCTCCAGACTCTCAG

GCAATGACCTGATAGCCTTTGTAGAGACCTCTCAAAAATAGCTACCCTCTCCGGCATGAATTT

ATCAGCTAGAACGGTTGAATATCATATTGATGGTGATTTGACTGTCTCCGGCCTTTCTCACCC

GTTTGAATCTTTACCTACACATTACTCAGGCATTGCATTTAAAATATATGAGGGTTCTAAAAA

TTTTTATCCTTGCGTTGAAATAAAGGCTTCTCCCGCAAAAGTATTACAGGGTCATAATGTTTT

TGGTACAACCGATTTAGCTTTATGCTCTGAGGCTTTATTGCTTAATTTTGCTAATTCTTTGCC

TTGCCTGTATGATTTATTGGATGTTGGAATTCCTGATGCGGTATTTTCTCCTTACGCATCTGT

GCGGTATTTCACACCGCATATGGTGCACTCTCAGTACAATCTGCTCTGATGCCGCATAGTTAA

GCCAGCCCCGACACCCGCCAACACCCGCTGACGCGCCCTGACGGGCTTGTCTGCTCCCGGCAT

CCGCTTACAGACAAGCTGTGACCGTCTCCGGGAGCTGCATGTGTCAGAGGTTTTCACCGTCAT

CACCGAAACGCGCGAGACGAAAGGGCCTCGTGATACGCCTATTTTTATAGGTTAATGTCATGA

TAATAATGGTTTCTTAGACGTCAGGTGGCACTTTTCGGGGAAATGTGCGCGGAACCCCTATTT

GTTTATTTTTCTAAATACATTCAAATATGTATCCGCTCATGAGACAATAACCCTGATAAATGC

TTCAATAATATTGAAAAAGGAAGAGTATGAGTATTCAACATTTCCGTGTCGCCCTTATTCCCT

TTTTTGCGGCATTTTGCCTTCCTGTTTTTGCTCACCCAGAAACGCTGGTGAAAGTAAAAGATG

CTGAAGATCAGTTGGGTGCACGAGTGGGTTACATCGAACTGGATCTCAACAGCGGTAAGATCC

TTGAGAGTTTTCGCCCCGAAGAACGTTTTCCAATGATGAGCACTTTTAAAGTTCTGCTATGTG

GCGCGGTATTATCCCGTATTGACGCCGGGCAAGAGCAACTCGGTCGCCGCATACACTATTCTC

AGAATGACTTGGTTGAGTACTCACCAGTCACAGAAAAGCATCTTACGGATGGCATGACAGTAA

GAGAATTATGCAGTGCTGCCATAACCATGAGTGATAACACTGCGGCCAACTTACTTCTGACAA

CGATCGGAGGACCGAAGGAGCTAACCGCTTTTTTGCACAACATGGGGGATCATGTAACTCGCC

TTGATCGTTGGGAACCGGAGCTGAATGAAGCCATACCAAACGACGAGCGTGACACCACGATGC

CTGTAGCAATGGCAACAACGTTGCGCAAACTATTAACTGGCGAACTACTTACTCTAGCTTCCC

GGCAACAATTAATAGACTGGATGGAGGCGGATAAAGTTGCAGGACCACTTCTGCGCTCGGCCC

TTCCGGCTGGCTGGTTTATTGCTGATAAATCTGGAGCCGGTGAGCGTGGGTCTCGCGGTATCA

TTGCAGCACTGGGGCCAGATGGTAAGCCCTCCCGTATCGTAGTTATCTACACGACGGGGAGTC

AGGCAACTATGGATGAACGAAATAGACAGATCGCTGAGATAGGTGCCTCACTGATTAAGCATT

GGTAACTGTCAGACCAAGTTTACTCATATATACTTTAGATTGATTTAAAACTTCATTTTTAAT

TTAAAAGGATCTAGGTGAAGATCCTTTTTGATAATCTCATGACCAAAATCCCTTAACGTGAGT

TTTCGTTCCACTGAGCGTCAGACCCCGTAGAAAAGATCAAAGGATCTTCTTGAGATCCTTTTT

TTCTGCGCGTAATCTGCTGCTTGCAAACAAAAAAACCACCGCTACCAGCGGTGGTTTGTTTGC

CGGATCAAGAGCTACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCTGTAGCACCGCCTA

CATACCTCGCTCTGCTAATCCTGTTACCAGTGGCTGCTGCCAGTGGCGATAAGTCGTGTCTTA

CCGGGTTGGACTCAAGACGATAGTTACCGGATAAGGCGCAGCGGTCGGGCTGAACGGGGGGTT

CGTGCACACAGCCCAGCTTGGAGCGAACGACCTACACCGAACTGAGATACCTACAGCGTGAGC

TATGAGAAAGCGCCACGCTTCCCGAAGGGAGAAAGGCGGACAGGTATCCGGTAAGCGGCAGGG

TCGGAACAGGAGAGCGCACGAGGGAGCTTCCAGGGGGAAACGCCTGGTATCTTTATAGTCCTG

TCGGGTTTCGCCACCTCTGACTTGAGCGTCGATTTTTGTGATGCTCGTCAGGGGGCGGAGCC

TATGGAAAAACGCCAGCAACGCGGCCTTTTTACGGTTCCTGGCCTTTTGCTGGCCTTTTGCTC
```

-continued

```
ACATGTTCTTTCCTGCGTTATCCCCTGATTCTGTGGATAACCGTATTACCGCCTTTGAGTGAG

CTGATACCGCTCGCCGCAGCCGAACGACCGAGCGCAGCGAGTCAGTGAGCGAGGAAGCGGAAG

AGCGCCCAATACGCAAACCGCCTCTCCCCGCGCGTTGGCCGATTCATTAATGCAGCAGCTGCG

CGCTCGCTCGCTCACTGAGGCCGCCCGGGCAAAGCCCGGGCGTCGGGCGACCTTTGGTCGCCC

GGCCTCAGTGAGCGAGCGAGCGCGCAGAGAGGGAGTGGCCAACTCCATCACTAGGGGTTCCTT

GTAGTTAATGATTAACCCGCCATGCTACTTATCTACGTAGCCATGCTCTAGGACATTGATTAT

TGACTAGTGGAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAGGGACTTTC

CATTGACGTCAATGGGTGGAGTATTTACGGTAAACTGCCCACTTGGCAGTACATCAAGTGTAT

CATATGCCAAGTACGCCCCCTATTGACGTCAATGACGGTAAATGGCCCGCCTGGCATTATGCC

CAGTACATGACCTTATGGGACTTTCCTACTTGGCAGTACATCTACGTATTAGTCATCGCTATT

ACCATGGTCGAGGTGAGCCCCACGTTCTGCTTCACTCTCCCCATCTCCCCCCCCTCCCCACCC

CCAATTTTGTATTTATTTATTTTTTAATTATTTTGTGCAGCGATGGGGGCGGGGGGGGGGGG

GGCGCGCGCCAGGCGGGGCGGGGGGGGCGAGGGGCGGGGCGGGGCGAGGCGGAGAGGTGCGG

CGGCAGCCAATCAGAGCGGCGCGCTCCGAAAGTTTCCTTTTATGGCGAGGCGGCGGCGGCGGC

GGCCCTATAAAAAGCGAAGCGCGCGGCGGGCGGGAGTCGCTGCGCGCTGCCTTCGCCCCGTGC

CCCGCTCCGCCGCCGCCTCGCGCCGCCCGCCCCGGCTCTGACTGACCGCGTTACTAAAACAGG

TAAGTCCGGCCTCCGCGCCGGGTTTTGGCGCCTCCCGCGGGCGCCCCCCTCCTCACGGCGAGC

GCTGCCACGTCAGACGAAGGGCGCAGCGAGCGTCCTGATCCTTCCGCCCGGACGCTCAGGACA

GCGGCCCGCTGCTCATAAGACTCGGCCTTAGAACCCCAGTATCAGCAGAAGGACATTTTAGGA

CGGGACTTGGGTGACTCTAGGGCACTGGTTTTCTTTCCAGAGAGCGGAACAGGCGAGGAAAAG

TAGTCCCTTCTCGGCGATTCTGCGGAGGGATCTCCGTGGGCGGTGAACGCCGATGATGCCTC

TACTAACCATGTTCATGTTTTCTTTTTTTTCTACAGGTCCTGGGTGACGAACAGGGTACCGC

CACCATGAGGGGCATGAAGCTGCTGGGGGCGCTGCTGGCACTGGCGGCCCTACTGCAGGGGGC

CGTGTCCATGGCGCTGTGGATGCGCCTGCTGCCGCTGCTGGCGCTGCTGGCGCTGTGGGCCC

GGATCCGGCGGCGGCGTTTGTGAACCAGCATCTGTGCGGCAGCCATCTGGTGGAAGCGCTGTA

TCTGGTGTGCGGCGAACGCGGCTTTTTTTATACCCCGAAAACCCGCCGCGAAGCGGAAGATCT

GCAGGTGGGCCAGGTGGAACTGGGCGGCGGCCCGGGCGCGGGCAGCCTGCAGCCGCTGGCGCT

GGAAGGCAGCCTGCAGAAACGCGGCATTGTGGAACAGTGCTGCACCAGCATTTGCAGCCTGTA

TCAGCTGGAAAACTATTGCAACGGCGGATCAGGCGGATCACCCAAATCTTGTGACAAAACTC

ACACATGCCCACCGTGCCCAGCACCTGAACTCCTGGGGGGACCGTCAGTCTTCCTCTTCCCCC

CAAAACCCAAGGACACCCTCATGATCTCCCGGACCCCTGAGGTCACATGCGTGGTGGTGGACG

TGAGCCACGAAGACCCTGAGGTCAAGTTCAACTGGTACGTGGACGGCGTGGAGGTGCATAATG

CCAAGACAAAGCCGCGGGAGGAGCAGTACAACAGCACGTACCGTGTGGTCAGCGTCCTCACCG

TCCTGCACCAGGACTGGCTGAATGGCAAGGAGTACAAGTGCAAGGTCTCCAACAAAGCCCTCC

CAGCCCCCATCGAGAAAACCATCTCCAAAGCCAAAGGGCAGCCCCGAGAACCACAGGTGTACA

CCCTGCCCCCATCCCGGGAGGAGATGACCAAGAACCAGGTCAGCCTGACCTGCCTGGTCAAAG

GCTTCTATCCCAGCGACATCGCCGTGGAGTGGGAGAGCAATGGGCAGCCGGAGAACAACTACA
```

```
AGACCACGCCTCCCGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCATGAGGCTCTGCACA

ACCACTACACGCAGAAGAGCCTCTCCCTGTCTCCGGGTAAATAG3'
```

As will be appreciated by those skilled in the art, because the recombinant plasmid is a circular vector, the one or more sequences of the mRNA expression cassettes may be connected at the 3' end of SEQ ID NO.1, as shown in SEQ ID NO.7-11 or at the 5' end of SEQ ID NO.1.

As will be appreciated by those skilled in the art, a perfect match of nucleotides with each of the miRNA expression cassette sequences is not necessary in order to have the desired result of increased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the mRNA expression cassettes causes the desired result. In some embodiments of the present disclosure, about 85% to about 100% nucleotide sequence matching with each of the mRNA expression cassettes causes the desired result. In some embodiments of the present disclosure, about 90% to about 100% nucleotide sequence matching with each of the mRNA expression cassettes causes the desired result. In some embodiments of the present disclosure, about 95% to about 100% nucleotide sequence matching with each of the mRNA expression cassettes causes the desired result.

Example 1—Expression Cassette

Expression cassettes for expressing mRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mRNA expression cassette was amplified by polymerase chain reaction (PCR) using Taq polymerase and the PCR products were gel purified and the bands on interest were also excised and purified using a gel extraction kit. These PCR products contained the mRNA expression cassettes in addition to 15 base pair 5' and 3' overhangs that aligned with the ends of the linearized pAVA-00200 backbone. Using in-fusion cloning, the amplified mRNA expression cassettes are integrated with the pAVA-00200 backbone via homologous recombination. The resulting RP contained the following: 5' ITR, CASI promoter, miRNA expression cassette, WPRE, SV40 polyA and ITR 3'.

The invention claimed is:

1. An isolated plasmid comprising the nucleic acid sequence of SEQ ID NO: 2 encoding a messenger RNA (mRNA) encoding a fusion protein comprising a DNAse-I protein and an Fc domain.

2. The isolated plasmid of claim 1, wherein the isolated plasmid is inserted within one or more suitable pharmaceutically acceptable carriers.

3. An isolated plasmid comprising the nucleic acid sequence of SEQ ID NO: 7 encoding a messenger RNA (mRNA) encoding a fusion protein comprising a DNAse-I protein and an Fc domain.

* * * * *

SEQUENCE LISTING

```
Sequence total quantity: 11
SEQ ID NO: 1              moltype = DNA  length = 5861
FEATURE                   Location/Qualifiers
source                    1..5861
                          mol_type = other DNA
                          organism = synthetic construct
SEQUENCE: 1
ttctagaata atcaacctct ggattacaaa atttgtgaaa gattgactgg tattcttaac   60
tatgttgctc cttttacgct atgtggatac gctgctttaa tgcctttgta tcatgctatt  120
gcttcccgta tggctttcat tttctcctcc ttgtataaat cctggttgct gtctctttat  180
gaggagttgt ggcccgttgt caggcaacgt ggcgtggtgt gcactgtgtt tgctgacgca  240
accccactg gttggggcat tgccaccacc tgtcagctcc tttccgggac tttcgctttc   300
cccctcccta ttgccacggc ggaactcatc gccgcctgcc ttgcccgctg ctggacaggg  360
gctcggctgt tgggcactga caattccgtg gtgttgtcgg ggaaatcatc gtcctttcct  420
tggctgctcg cctgtgttgc cacctggatt ctgcgcggga cgtccttctg ctacgtccct  480
tcggccctca atccagcgga ccttccttcc cgcggcctgc tgccggctct gcggcctctt  540
ccgcgtcttc gccttcgccc tcagacgagt cggatctccc tttgggcgcc ctccccgcct  600
aagcttatcg ataccgtcga gatctaactt gtttattgca gcttataatg gttacaaata  660
aagcaatagc atcacaaatt tcacaaataa agcattttt tcactgcatt ctagttgtgg  720
tttgtccaaa ctcatcaatg tatcttatca tgtctggatc tcgacctcga ctagagcatg  780
gctacgtaga taagtagcat ggcgggttaa tcattaacta caaggaaccc ctagtgatgg  840
agttggccac tccctctctg cgcgctcgct cgctcactga ggccgggcga ccaaaggtcg  900
cccgacgccc gggctttgcc cgggcggcct cagtgagcga gcgagcgcgc cagctggcgt  960
aatagcgaag aggcccgcac cgatcgccct tcccaacagt tgcgcagcct gaatggcgaa 1020
tggaattcca gacgattgag cgtcaaaatg taggtatttc catgagcgtt tttcctgttg 1080
caatggctgg cggtaatatt gttctggata ttaccagcaa ggccgatagt ttgagttctt 1140
ctactcaggc aagtgatgtt attactaatc aaagaagtat tgcgacaacg gttaatttgc 1200
gtgatggaca gactctttta ctcggtggcc tcactgatta taaaaacact tctcaggatt 1260
ctggcgtacc gttcctgtct aaaatccctt taatcggcct cctgtttagc tcccgctctg 1320
attctaacga ggaaagcacg ttatacgtgc tcgtcaaagc aaccatagta cgcgccctgt 1380
agcggcgcat taagcgcggc gggtgtggtg gttacgcgca gcgtgaccgc tacacttgcc 1440
agcgccctag cgcccgctcc tttcgctttc ttcccttcct ttctcgccac gttcgccggc 1500
tttccccgtc aagctctaaa tcgggggctc cctttagggt tccgatttag tgctttacgg 1560
cacctcgacc ccaaaaaact tgattaggggt gatggttcac gtagtgggcc atcgccctga 1620
tagacggttt ttcgcccttt gacgttggag tccacgttct ttaatagtgg actcttgttc 1680
caaactggaa caacactcaa ccctatccg gtctattctt ttgatttata agggattttg 1740
ccgatttcgg cctattggtt aaaaaatgag ctgatttaac aaaaatttaa cgcgaatttt 1800
```

```
aacaaaatat taacgtttac aatttaaata tttgcttata caatcttcct gttttgggg    1860
cttttctgat tatcaaccgg ggtacatatg attgacatgc tagttttacg attaccgttc    1920
atcgattctc ttgtttgctc cagactctca ggcaatgacc tgatagcctt tgtagagacc    1980
tctcaaaaat agctaccctc tccggcatga atttatcagc tagaacggtt gaatatcata    2040
ttgatggtga tttgactgtc tccggccttt ctcacccgtt tgaatcttta cctacacatt    2100
actcaggcat tgcatttaaa atatatgagg gttctaaaaa tttttatcct tgcgttgaaa    2160
taaaggcttc tcccgcaaaa gtattacagg gtcataatgt ttttggtaca accgatttag    2220
ctttatgctc tgaggcttta ttgcttaatt ttgctaattc tttgccttgc ctgtatgatt    2280
tattggatgt tggaattcct gatgcggtat tttctcctta cgcatctgtg cggtatttca    2340
caccgcatat ggtgcactct cagtacaatc tgctctgatg ccgcatagtt aagccagccc    2400
cgacacccgc caacccgc tgacgcgccc tgacgggctt gtctgctccc ggcatccgct    2460
tacagacaag ctgtgaccgt ctccgggagc tgcatgtgtc agaggttttc accgtcatca    2520
ccgaaacgcg cgagacgaaa gggcctcgtg atacgcctat ttttataggt taatgtcatg    2580
ataataaatgg tttcttagac gtcaggtggc actttttcgg gaaatgtgcg cggaacccct    2640
atttgtttat ttttctaaat acattcaaat atgtatccgc tcatgagaca ataaccctga    2700
taaatgcttc aataatattg aaaaggaag agtatgagta ttcaacattt ccgtgtcgcc    2760
cttattccct tttttgcggc atttttgcctt cctgtttttg ctcacccaga aacgctggtg    2820
aaagtaaaag atgctgaaga tcagttgggt gcacgagtgg gttacatcga actgatctc    2880
aacagcggta agatccttga gagttttcgc cccgaagaac gttttccaat gatgagcact    2940
tttaaagttc tgctatgtgg cgcggtatta tcccgtattg acgccgggca agagcaactc    3000
ggtcgccgca tacactattc tcagaatgac ttggttgagt actcaccagt cacagaaaag    3060
catcttacgg atggcatgac agtaagagaa ttatgcagtg ctgccataac catgagtgat    3120
aacactgcgg ccaacttact tctgacaacg atcggaggac cgaaggagct aaccgctttt    3180
ttgcacaaca tgggggatca tgtaactcgc cttgatcgtt gggaaccgga gctgaatgaa    3240
gccataccaa acgacgagcg tgacaccacg atgcctgtag caatggcaac aacgttgcgc    3300
aaactattaa ctggcgaact acttactcta gcttcccggc aacaattaat agactggatg    3360
gaggcggata aagttgcagg accacttctg cgctcggccc ttccggctgg ctggtttatt    3420
gctgataaat ctggagccgg tgagcgtggg tctcgcggta tcattgcagc actggggcca    3480
gatggtaagc cctcccgtat cgtagttatc tacacgacgg ggagtcaggc aactatggat    3540
gaacgaaata gacagatcgc tgagataggt gcctcactga ttaagcattg gtaactgtca    3600
gaccaagttt actcatatat actttagatt gatttaaaac ttcatttta atttaaaagg    3660
atctaggtga agatcctttt tgataatctc atgaccaaaa tcccttaacg tgagttttcg    3720
ttccactgag cgtcagaccc cgtagaaaag atcaaaggat cttcttgaga tccttttttt    3780
ctgcgcgtaa tctgctgctt gcaaacaaaa aaaccaccgc taccagcggt ggtttgtttg    3840
ccggatcaag agctaccaac tctttttccg aaggtaactg gcttcagcag agcgcagata    3900
ccaaatactg tccttctagt gtagccgtag ttaggccacc acttcaagaa ctctgtagca    3960
ccgcctacat acctcgctct gctaatcctg ttaccagtgg ctgctgccag tggcgataag    4020
tcgtgtctta ccgggttgga ctcaagacga tagttaccgg ataaggcgca gcggtcgggc    4080
tgaacggggg gttcgtgcac acagcccagc ttggagcgaa cgacctacac cgaactgaga    4140
tacctacagc gtgagctatg agaaagcgcc acgcttcccg aagggagaaa ggcggacagg    4200
tatccggtaa gcggcaggt cggaacagga gagcgcacga gggagcttcc agggggaaac    4260
gcctggtatc tttatagtcc tgtcgggttt cgccacctct gacttgagcg tcgatttttg    4320
tgatgctcgt cagggggggcg gagcctatgg aaaaacgcca gcaacgcggc ctttttacgg    4380
ttcctggcct tttgctggcc ttttgctcac atgttctttc ctgcgttatc ccctgattct    4440
gtggataacc gtattaccgc ctttgagtga gctgataccg ctcgccgcag ccgaacgacc    4500
gagcgcagcg agtcagtgag cgaggaagcg gaagagcgcc caatacgcaa accgcctctc    4560
cccgcgcgtt ggccgattca ttaatgcagc agctgcgcgc tcgctcgctc actgaggccg    4620
cccgggcaaa gcccgggcgt cgggcgacct tggtcgcccc ggcctcagtg agcgagcgag    4680
cgcgcagaga gggagtggcc aactccatca ctaggggttc cttgtagtta atgattaacc    4740
cgccatgcta cttatctacg tagccatgct ctaggacatt gattattgac tagtggagtt    4800
ccgcgttaca taacttacgg taaatgccc gcctggctga ccgcccaacg accccccgcc    4860
attgacgtca ataatgacgt atgttcccat agtaacgcca atagggactt tccattgacg    4920
tcaatgggtg gagtatttac ggtaaactgc ccacttggca gtacatcaag tgtatcatat    4980
gccaagtacg ccccctattg acgtcaatga cggtaaatgg cccgcctggc attatgccca    5040
gtacatgacc ttatgggact ttcctacttg gcagtacatc tacgtattag tcatcgctat    5100
taccatggtc gaggtgagcc ccacgttctg cttcactctc cccatctccc ccccctcccc    5160
accccccaatt ttgtatttat ttatttttta attattttgt gcagcgatgg gggcggggg    5220
ggggggggc gcgcgccagg cggggcgggg cgggcgagg ggcggggcgg ggcgaggcgg    5280
agaggtgcgg cggcagccaa tcagagcggc gcgctccgaa agtttccttt tatgcgagg    5340
cggcggcggc ggcggcccta taaaaagcga agcgcgcggc gggcgggagt cgctgcgcgc    5400
tgccttcgcc ccgtgccccg ctccgccgcc gcctcgcgcc gcccgccccg gctctgactg    5460
accgcgttac taaaacaggt aagtccggcc tccgcgccgg gttttggcgc ctcccgcggg    5520
cgccccctc ctcacggcga gcgctgccac gtcagacgaa gggcgcagcg agcgtcctga    5580
tccttccgcc cggacgctca ggacagcggc ccgctgctca taagactcgg cctagaacc    5640
ccagtatcag cagaaggaca tttttaggacg ggacttgggt gactctaggg cactggtttt    5700
ctttccagag agcggaacag gcgaggaaaa gtagtcccttt ctcggcgatt ctgcggaggg    5760
atctccgtgg ggcggtgaac gccgatgatg cctctactaa ccatgttcat gtttttctttt    5820
tttttctaca ggtcctgggt gacgaacagg gtaccgccac c                       5861
```

SEQ ID NO: 2          moltype = DNA   length = 1560
FEATURE               Location/Qualifiers
source                1..1560
                        mol_type = other DNA
                        organism = synthetic construct
SEQUENCE: 2

```
atgagggca tgaagctgct gggggcgctg ctggcactgg cggccctact gcaggggcc    60
gtgtccctga agatcgcagc cttcaacatc cagacatttg gggagaccaa gatgtccaat    120
gccaccctcg tcagctacat tgtgcagatc ctgagccgct atgacatcgc cctggtccag    180
gaggtcagag acagccacct gactgccgtg gggaagctgc tggacaacct caatcaggat    240
```

```
gcaccagaca cctatcacta cgtggtcagt gagccactgg gacggaacag ctataaggag    300
cgctacctgt tcgtgtacag gcctgaccag gtgtctgcgg tggacagcta ctactacgat    360
gatggctgcg agcccgcgg gaacgacacc ttcaaccgag agccagccat tgtcaggttc    420
ttctcccggt tcacagaggt cagggagttt gccattgttc ccctgcatgc ggccccgggg    480
gacgcagtag ccgagatcga cgctctctat gacgtctacc tggatgtcca agagaaatgg    540
ggcttggagg acgtcatgtt gatgggcgac ttcaatgcgg gctgcagcta tgtgagaccc    600
tcccagtggt catccatccg cctgtggaca agccccacct tccagtggct gatccccgac    660
agcgctgaca ccacagctac acccacgcac tgtgcctatg acaggatcgt ggttgcaggg    720
atgctgctcc gaggcgccgt tgttcccgac tcggctcttc cctttaactt ccaggctgcc    780
tatggcctga gtgaccaact ggccaagcc atcagtgacc actatccagt ggaggtgatg    840
ctgaagggcg gatcaggcgg atcacccaaa tcttgtgaca aaactcacac atgcccaccg    900
tgcccagcac ctgaactcct gggggggaccg tcagtcttcc tcttcccccc aaaacccaag    960
gacaccctca tgatctcccg gacccctgag gtcacatgcg tggtggtgga cgtgagccac   1020
gaagaccctg aggtcaagtt caactggtac gtggacggcg tggaggtgca taatgccaag   1080
acaaagccgc gggaggagca gtacaacagc acgtaccgtg tggtcagcgt cctcaccgtc   1140
ctgcaccagg actggctgaa tggcaaggag tacaagtgca aggtctccaa caaagccctc   1200
ccagccccca tcgagaaaac catctccaaa gccaagggc agccccgaga accacaggtg   1260
tacacccctgc ccccatcccg ggaggagatg accaagaacc aggtcagcct gacctgcctg   1320
gtcaaaggct tctatcccag cgacatcgcc gtggagtggg agagcaatgg gcagccggag   1380
aacaactaca agaccacgcc tcccgtgctg gactccgacg gctccttctt cctctacagc   1440
aagctcaccg tggacaagag caggtggcag caggggaacg tcttctcatg ctccgtgatg   1500
catgaggctc tgcacaacca ctacacgcag aagagcctct ccctgtctcc gggtaaatag   1560

SEQ ID NO: 3             moltype = DNA   length = 3423
FEATURE                  Location/Qualifiers
source                   1..3423
                         mol_type = other DNA
                         organism = synthetic construct
SEQUENCE: 3
gccagaccct gccgtgcatt tattttttggg gcggcctgct gccgtttggc atgctgtgcg     60
cgagcagcac caccaaatgc accgtgagcc atgaagtggc ggattgcagc catctgaaac    120
tgacccaggt gccggatgat ctgccgacca acattaccgt gctgaacctg acccataacc    180
agctgcgccg cctgccggcg gcgaacttta cccgctatag ccagctgacc agcctggatg    240
tgggctttaa caccattagc aaactggaac cggaactgtg tcagaaactg gccgatgctga    300
aagtgctgaa cctgcagcga aacgactga gccagctgga cgataaaacc tttgcgtttt    360
gcaccaacct gaccgaactg catctgatga gcaacagcat tcagaaaatt aaaaacaacc    420
cgtttgtgaa acagaaaaac ctgattaccc tggatctgag ccataacggc ctgagcagca    480
ccaaactggg cacccaggtg cagctggaaa acctgcagga actgctgctg agcaacaaca    540
aaattcaggc gctgaaaagc gaagaactgg atatttttgc gaacagcagc ctgaaaaaac    600
tggaactgag cagcaaccag attaaagaat ttagcccggg ctgctttcat gcgattggcc    660
gcctgtttgg cctgtttctg aacaacgtgc agctgggccc gagcctgacc gaaaaactgt    720
gcctggaact ggcgaacacc agcattgcga acctgagcct gagcaacagc cagctgagca    780
ccaccagcaa caccacctt ctgggcctga atggaccaa gaccatg ctggatctgga    840
gctataacaa cctgaacgtg gtgggcaacg atagctttgc gtggctgccg cagctggaat    900
attttttttct ggaatataac aacattcagc atctgtttag ccatagcctg catggcctgt    960
ttaacgtgcg ctatctgaac ctgaaacgca gctttaccaa acagagcatt agcctggcga   1020
gcctgccgaa aattgatgat tttagctttc agtggctgaa gtgcctggaa catctgaaca   1080
tggaagataa cgatattccg ggcattaaaa gcaacatgtt taccggcctg attaacctga   1140
aatatctgag cctgagcaac agctttacca gcctgcgcac cctgaccaac gaaacctttg   1200
tgagcctggc gcatagcccg ctgcatattc tgaacctgac caaaaacaaa attagcaaaa   1260
ttgaaagcga tgcgtttagc tggctgggcc atctggaagt gctggatcg ggcctgaacg   1320
aaattggcca ggaactgacc ggccaggaat ggcgcggcct ggaaaacatt tttgaaattt   1380
atctgagcta taacaaatat ctgcagctga cccgcaacag ctttgcgctg gtgccgagcc   1440
tgcagcgcct gatgctgcgc cgcgtggcgc tgaaaaacgt ggatagcagc ccgagcccgt   1500
ttcagccgct gcgcaaacatg accattctgg atctgagcaa caacaacatt gcgaacatta   1560
acgatgatat gctggaaggc ctggaaaaac tggaaattct ggatctgcag cataacaacc   1620
tggcgcgcct gtgaaacat gcgaacccgg gcggccgat ttattttctg aaaggcctga   1680
gccatcgca tattctgaac ctggaaagca cggctttga tgaaattccg gtggaagtgt   1740
ttaaagatct gtttgaactg aaaattattg atctgggcct gaacaacctg aaccaccctgt   1800
cggcgagcgt gtttaacaac caggtgagcc tgaaaagcct gaacctgcag aaaaacctga   1860
ttaccagcgt ggaaaaaaaa gtgtttggcc cggcgtttcg caacctgacc gaactggata   1920
tgcgctttaa cccgtttgat tgcacctgcg aaagcattgc gtggtttgtg aactggatta   1980
acgaaaccca taccaacatt ccggaactga gcagccatta tctgtgcaac ccccgccgc   2040
attatcatgg ctttccggtg cgcctgtttg ataccagcag ctgcaaagat agcgcgccgt   2100
ttgaactgtt ttttatgatt aacaccagca ttctgctgat ttttattttt attgtgctgc   2160
tgattcattt tgaaggctgg cgcattagct ttattggaa cgtgagcgtg catcgcgtgc   2220
tgggctttaa agaaattgat cgccagaccg aacagtttga atatgcggcg tatattattc   2280
atgcgtataa agataaaagat tgggtgtggg aacattttag cagcggaaaa gaagatc    2340
agagcctgaa attttgcctg gaagaaacgc attttgaagc gggcgtgttt gaactggaag   2400
cgattgtgaa cagcattaaa gcagcccga aattattttt tgtgattacc catcatctgc   2460
tgaaagatcc gctgtgcaaa cgctttaaag tgcatcatgc ggtgcagcag gcgattgaac   2520
agaacctgga tagcattatt ctggtgtttc tggaagaaat tccggattat aaactgaacc   2580
atgcgctgtg cctgcgccgc ggcatgttta aagccattgc attctgaac tggccggtgc   2640
agaaagaacg cattgcggcg tttcgccata aactgcaggt ggcgaaaaaca ttttgaaggtgacg   2700
gcgtgcatgg gcggatcagg cggatcaccc aaatcttgtg acaaaactca catgcccca   2760
ccgtgcccag cacctgaact cctgggggga ccgtcagtct tcctcttccc cccaaaaccc   2820
aaggacaccc tcatgatctc ccggaccctt gaggtcacat gcgtggtggt ggacgtgagc   2880
cacgaagacc ctgaggtcaa gttcaactgg tacgtggacg gcgtggaggt gcataatgcc   2940
aagacaaagc cgcgggagga gcagtacaac agcacgtacc gtgtggtcag cgtcctcacc   3000
```

```
gtcctgcacc aggactggct gaatggcaag gagtacaagt gcaaggtctc aacaaagcc   3060
ctcccagccc ccatcgagaa aaccatctcc aaagccaaag gcagccccg agaaccacag   3120
gtgtacaccc tgcccccatc ccgggaggag atgaccaaga accaggtcag cctgacctgc   3180
ctggtcaaag gcttctatcc cagcgacatc gccgtggagt gggagagcaa tgggcagccg   3240
gagaacaact acaagaccac gcctcccgtg ctggactccg acggctcctt cttcctctac   3300
agcaagctca ccgtggacaa gagcaggtgg cagcagggga acgtcttctc atgctccgtg   3360
atgcatgagg ctctgcacaa ccactacacg cagaagagcc tctccctgtc tccgggtaaa   3420
tag                                                                3423

SEQ ID NO: 4           moltype = DNA   length = 3877
FEATURE                Location/Qualifiers
source                 1..3877
                       mol_type = other DNA
                       organism = synthetic construct
SEQUENCE: 4
atgaggggca tgaagctgct gggggcgctg ctggcactgg cggccctact gcaggggcc   60
gtgtccatgg gcttttgccg cagcgcgctg catccgctga gcctgctggt gcaggcgatt   120
atgctggcga tgaccctggc gctgggcacc ctgccggcgt ttctgccgtg cgaactgcag   180
ccgcatggcc tggtgaactg caactggctg tttctgaaaa gcgtgccgca ttttagcatg   240
gcggcgccgc gcggcaacgt gaccagcctg agcctgagca gcaaccgcat tcatcatctg   300
catgatagcg attttgcgca tctgccgagc ctgccgccatc tgaacctgaa atggaactgc   360
ccgccggtgg gcctgagccc gatgcatttt ccgtgccata tgaccattga accgagcacc   420
tttctggcgg tgccgaccct ggaagaactg aacctgagct ataacaacat tatgaccgtg   480
ccggcgctgc cgaaaagcct gattagcctg agcctgagcc ataccaacat tctgatgctg   540
gatagcgcga gcctggcggg cctgcatgcg ctgcgctttc tgtttatgga tggcaactgc   600
tattataaaa acccgtgccg ccaggcgctg gaagtgctgc cgcgcgcgct gctgggcctg   660
ggcaacctga cccatctgag cctgaaatat aacaacctga ccgtggtgcc gcgcaacctg   720
ccgagcagcc tggaatatct gctgctgagc tataaccgca ttgtgaaact ggcgccggaa   780
gatctggcga acctgaccgc gctgcgcgtg ctggatgtgg cggcaactg ccgccgctgc   840
gatcatgcc cgaacccgtg catgaatgc ccgcgccatt ttccgcagct gcatccgcat   900
acctttagcc atctgagccg cctggaaggc ctggtgctga agatagcag cctgagctgg   960
ctgaacgcga gctggtttcg cggcctgggc aacctgcgcg tgctggatct gagcgaaaac   1020
tttctgtata aatgcattac caaaaccaaa gcgtttcagg gcctgaccca gctgcgcaaa   1080
ctgaacctga gctttaacta tcagaaacgc gtgagctttg cgcatctgag cctggcgccg   1140
agctttggca gcctggtggc gctgaaagaa ctggatatgc atggcatttt ttttcgcagc   1200
ctggatgaaa ccaccctgcg cccgctggcg cgctgccga tgctgcagac cctgcgcctg   1260
cagatgaact tattaacca ggcgcagctg ggcattttc gcgcgtttcc gggcctgcgc   1320
tatgtggatc tgagcgataa ccgcattagc ggcgcgagcg aactgaccgc gaccatgggc   1380
gaagcggatg gcggcgaaaa agtgtggctg cagccgggcg atctggcgcc ggcgccggtg   1440
gatacccga gcagcgaaga ttttcgcccc aactgcagca ccctgaactt taccctggat   1500
ctgagccgca caacctggt gaccgtgcag ccggaaatgt tgcgcagct gagccatctg   1560
cagtgcctgc gcctgagcca taactgcatt agccaggcgg tgaacggcag ccagtttctg   1620
ccgctgaccg gcctgcaggt gctggatctg agccataaca aactggatct gtatcatgaa   1680
catagcttta ccgaactgcc gcgcctgaa gcgctggatc tgagctataa cagccagccc   1740
tttggcatgc agggcgtggg ccataacttt agctttgtgg cgcatctgcg caccctgcgc   1800
catctgagcc tggcgcataa caacattcat agccaggtga ccagcagct gtgcagcacc   1860
agcctgcgcg cgctggattt tagcggcaac gcgctggccg atatgtgggc ggaaggcgat   1920
ctgtatctgc attttttttca gggcctgagc ggcctgattt gctggatct gagccagaac   1980
cgcctgcata ccctgctgcc gcagaccctg cgcaacctgc gaaaagcct gcaggtgctg   2040
cgcctgcgcg ataactatct ggcgtttttt aaatggtgga gcctgcattt tctgccgaaa   2100
ctggaagtgc tggatctggc gggcaaccag ctgaaagcgc tgaccaacgg cagcctgccg   2160
gcgggcaccc gcctgcgccg cctgatgtg agctgcaaca gcattagctt tgtggccgcg   2220
ggctttttta gcaaagcgaa agaactgcgc gaactgaacc tgagcgcgaa cgcgctgaaa   2280
accgtgatc atagctggtt tggccgctg gcgagcgcgc tgcagattct ggatgtgagc   2340
gcgaaccgc tgcattgcgc gtgctggcg gcgtttatgg atttttctgct ggaagtgcag   2400
gcggcggtgc cgggcctgcc gagccgcgtg aaatgcggca gcccgggcca gctgcagggc   2460
ctgagcattt ttgcgcagga tctgcgcctg tgcctggatg aagcgctgag ctgggattgc   2520
tttgcgctga gcctgctggc ggtggcgctg gcctgggcg tgccgatgct gcatcatctg   2580
tgcggctggg atctgtggta ttgctttcat ctgtgcctgg cgtggctgcc gtggcgcggc   2640
cgccagagcg gccgcagtga agatgcgctg ccgtatgatg cgtttgtggt gtttgataaa   2700
acccagagcg cggtggcgga ttgggtgtat aacgaactgc gcggccagct ggaagaatgc   2760
cgcggccgct gggcgctgcg cctgtgcctg gaagaacgcg attggctgcc gggcaaaacc   2820
ctgtttgaaa acctgtgggc gagcgtgtat ggcagccgca aaccctgtt tgtgctggcg   2880
cataccgatc gcgtgagcgg cctgctgcgc gcgagctttc tgctgcgca gcagcgctg   2940
ctggaagatc gcaaagatgt ggtggtgctg gtgattctga gcccggatgg ccgccgcagc   3000
cgctatgtgc cgctgcgcca gcgctgtgcc gccagagcg tgctgctgtg gccgcatcag   3060
ccgagcggcc agcgcagctt tgggcgcag ctgggcatgg cgctgacccg cgataaccat   3120
catttttata accgcaactt tgccagggc ccgaccgcg aagggcggat caggcggatc   3180
acccaaatct tgtgacaaaa ctcacacatg cccaccgtgc ccagcacctg aactcctgga   3240
gggaccgtca gtcttcctct tccccccaaa acccaaggac accctcatga tctcccggac   3300
ccctgaggtc acatgcgtgg tggtggacgt gagccacgaa gaccctgagg tcaagttcaa   3360
ctggtacgtg gacggcgtgg aggtgcataa tgccaagaca aagccgcggg aggagcagta   3420
caacagcacg taccgtgtgg tcagcgtcct caccgtcctg caccaggact ggctgaatgg   3480
caaggagtac aagtgcaagg tctccaacaa agccctccca gccccatcga gaaaaccat   3540
ctccaaagcc aaagggcagc ccgagaacc acaggtgtac accctgcccc catcccggga   3600
ggagatgacc aagaaccagg tcagcctgac ctgcctggtc aaaggcttct atccagcga   3660
catcgccgtg gagtgggaga gcaatgggca gccggagaac aactacaaga ccacgcctcc   3720
cgtgctggac tccgacggct ccttcttcct ctacagcaag ctcaccgtgg acaagagcag   3780
gtggcagcag gggaacgtct tctcatgctc cgtgatgcat gaggctctgc acaaccacta   3840
```

| | | |
|---|---|---|
| cacgcagaag agcctctccc tgtctccggg taaatag | | 3877 |

SEQ ID NO: 5          moltype = DNA  length = 1503
FEATURE             Location/Qualifiers
source              1..1503
                     mol_type = other DNA
                     organism = synthetic construct
SEQUENCE: 5

| | |
|---|---|
| atgaggggca tgaagctgct ggggggcgctg ctggcactgg cggccctact gcaggggggcc | 60 |
| gtgtccatga gcatgctgtt ttatacccctg attaccgcgt ttctgattgg cattcaggcg | 120 |
| gaaccgcata gcgaaagcaa cgtgccggcg ggccatacca ttccgcaggc gcattggacc | 180 |
| aaactgcagc atagcctgga taccgcgctg cgccgcgcgc gcagcgcgcc ggcggcggcc | 240 |
| attgcggcgc gcgtggcggg ccagacccgc aacattaccg tggatccgcg cctgtttaaa | 300 |
| aaacgcgcc tgcgcagccc gcgcgtgctg tttagcaccc agcaccgccg cgaagcgggg | 360 |
| gatacccagg atctggattt tgaagtgggc ggcgcggcgc cgtttaaccg cacccatcgc | 420 |
| agcaaacgca gcagcagcca tccgattttt catcgcggcg aatttagcgt gtgcgatagc | 480 |
| gtgagcgtgt gggtgggcga taaaaccacc gcgaccgata ttaaaggcaa agaagtgatg | 540 |
| gtgctgggcg aagtgaacat taacaacagc gtgtttaaac agtattttt tgaaaccaaa | 600 |
| tgccgcgatc cgaacccggt ggatagcggc tgccgcggca ttgatagcaa acattggaac | 660 |
| agctattgca ccaccaccca taccttttgtg aaagcgctga ccatggatgg caaacaggcg | 720 |
| gcgtggcgct tattcgcat tgataccgcg tgcgtgtgcg tgctgagccg caaagcggtg | 780 |
| cgccgcgcgg gcggatcagg cggatcaccc aaatcttgtg acaaaactca cacatgccca | 840 |
| ccgtgcccag cacctgaact cctgggggga ccgtcagtct tcctcttccc cccaaaaccc | 900 |
| aaggacaccc tcatgatctc ccggaccccct gaggtcacat gcgtggtggt ggacgtgagc | 960 |
| cacgaagacc ctgaggtcaa gttcaactgg tacgtggacg gcgtggaggt gcataatgcc | 1020 |
| aagacaaagc cgcggggagga gcagtacaac agcacgtacc gtgtggtcag cgtcctcacc | 1080 |
| gtcctgcacc aggactggct gaatggcaag gagtacaagt gcaaggtctc caacaaagcc | 1140 |
| ctcccagccc ccatcgagaa aaccatctcc aaagccaaag gcagccccg agaaccacag | 1200 |
| gtgtacaccc tgcccccatc ccgggaggag atgaccaaga accaggtcag cctgacctgc | 1260 |
| ctggtcaaag gcttctatcc cagcgacatc gccgtggagt gggagagcaa tgggcagccg | 1320 |
| gagaacaact acaagaccac gcctcccgtg ctggactccg acggctcctt cttcctctac | 1380 |
| agcaagctca ccgtggacaa gagcaggtgg cagcagggga acgtcttctc atgctccgtg | 1440 |
| atgcatgagg ctctgcacaa ccactacacg cagaagagcc tctccctgtc tccgggtaaa | 1500 |
| tag | 1503 |

SEQ ID NO: 6          moltype = DNA  length = 1111
FEATURE             Location/Qualifiers
source              1..1111
                     mol_type = other DNA
                     organism = synthetic construct
SEQUENCE: 6

| | |
|---|---|
| atgaggggca tgaagctgct ggggggcgctg ctggcactgg cggccctact gcaggggggcc | 60 |
| gtgtccatgg cgctgtggat gcgcctgctg ccgctgctgc gctgcgggac gctggggcc | 120 |
| ccggatccgg cggcgcgtt tgtgaaccag catctgtgcg gcagccatct ggtgaaagcc | 180 |
| ctgtatctgg tgtgcggcga acgcggcttt ttttatacccc cgaaaacccg ccgcgaagcg | 240 |
| gaagatctgc aggtgggcca ggtggaactg gcggcggcc cgggcgcggg cagcctgcag | 300 |
| ccgctggcac tggaaggcag cctgcagaaa cgcggcattg tgaacagtg ctgcaccagc | 360 |
| atttgcagcc tgtatcagct ggaaaactat tgcaacgggc ggatcaggcg gatcacccaa | 420 |
| atcttgtgac aaaactcaca catgcccacc gtgcccagca cctgaactcc tgggggggacc | 480 |
| gtcagtcttc ctcttccccc caaaacccaa ggacaccctc atgatctccc ggacccctga | 540 |
| ggtcacatgc gtggtggtgg acgtgagcca cgaagaccct gaggtcaagt tcaactggta | 600 |
| cgtggacggc gtggaggtgc ataatgccaa gacaaagccg cggggaggagc agtacaacag | 660 |
| cacgtaccgt gtggtcagcg tcctcaccgt cctgcaccag gactggctga atggcaagga | 720 |
| gtacaagtgc aaggtctcca acaaagcccct ccagccccc atcgagaaaa ccatctccaa | 780 |
| agccaaaggg cagccccgag aaccacaggt gtacaccctg ccccccatcc cgggaggaga | 840 |
| tgaccaagaa ccaggtcagc ctgacctgcc tggtcaaagg cttctatccc agcgacatcg | 900 |
| ccgtggagtg ggagagcaat gggcagccgg agaacaacta caagaccacg cctcccgtgc | 960 |
| tggactccga cggctccttc ttcctctacag caagctcacc gtggacaaga gcaggtggca | 1020 |
| gcaggggaac gtcttctcat gctccgtgat gcatgaggct ctgcacaacc actacacgca | 1080 |
| gaagagcctc tccctgtctc cgggtaaata g | 1111 |

SEQ ID NO: 7          moltype = DNA  length = 7421
FEATURE             Location/Qualifiers
source              1..7421
                     mol_type = other DNA
                     organism = synthetic construct
SEQUENCE: 7

| | |
|---|---|
| ttctagaata atcaacctct ggattacaaa atttgtgaaa gattgactgg tattcttaac | 60 |
| tatgttgctc cttttacgct atgtggatac gctgctttaa tgcctttgta tcatgctatt | 120 |
| gcttcccgta tggctttcat tttctcctcc ttgtataaat cctggttgct gtctctttat | 180 |
| gaggagttgt ggcccgttgt caggcaacgt ggcgtggtgt gcactgtgtt tgctgacgca | 240 |
| accccccactg gttggggcat tgccaccacc tgtcagctcc tttccgggac tttcgctttc | 300 |
| cccctcccta ttgccacggc ggaactcatc gccgcctgcc ttgcccgctg ctggacaggg | 360 |
| gctcggctgt tgggcactga caattccgtg gtgttgtcgg ggaaatcatc gtcctttcct | 420 |
| tggctgctcg cctgtgttgc cacctggatt ctgcgcggga cgtccttctg ctacgtccct | 480 |
| tcggccctca atccagcgga ccttccttcc cgcggcctgc tgccggctct gcggcctctt | 540 |
| ccgcgtcttc gccttcgccc tcagacgagt cggatctccc tttgggccgc ctccccgcct | 600 |
| aagcttatcg ataccgtcga gatctaactt gtttattgca gcttataatg gttacaaata | 660 |
| aagcaatagc atcacaaatt tcacaaataa agcatttttt tcactgcatt ctagttgtgg | 720 |

```
tttgtccaaa ctcatcaatg tatcttatca tgtctggatc tcgacctcga ctagagcatg    780
gctacgtaga taagtagcat ggcgggttaa tcattaacta caaggaaccc ctagtgatgg    840
agttggccac tccctctctg cgcgctcgct cgctcactga ggccgggcga ccaaaggtcg    900
cccgacgccc gggctttgcc cgggcggcct cagtgagcga gcgagcgcgc cagctggcgt    960
aatagcgaag aggcccgcac cgatcgccct tcccaacagt tgccgagcct gaatggcgaa   1020
tggaattcca gacgattgag cgtcaaaatg taggtatttc catgagcgtt tttcctgttg   1080
caatggctgg cggtaaatat tgttctggat attaccagca aggccgatag ttgagttctt   1140
ctactcaggc aagtgatgtt attactaatc aaagaagtat tgcgacaacg gttaatttgc   1200
gtgatggaca gactcttta ctcggtggcc tcactgatta taaaaacact tctcaggatt   1260
ctggcgtacc gttcctgtct aaaatcccctt taatcggcct cctgtttagc tcccgctctg   1320
attctaacga ggaaagcacg ttatacgtgc tcgtcaaagc aaccatagta cgcgccctgt   1380
agcggcgcat taagcgcggc gggtgtggtg gttacgcgca gcgtgaccgc tacacttgcc   1440
agcgccctag cgcccgctcc tttcgctttc ttcccttcct ttctcgccac gttcgccggc   1500
tttccccgtc aagctctaaa tcgggggctc cctttagggt tccgatttag tgctttacgg   1560
cacctcgacc ccaaaaaact tgattagggt gatggttcac gtagtgggcc atcgccctga   1620
tagacggttt ttcgcccttt gacgttggag tccacgttct ttaatagtgg actcttgttc   1680
caaactggaa caacactcaa ccctatctcg gtctattctt ttgatttata agggattttg   1740
ccgatttcgg cctattggtt aaaaaatgag ctgattaac aaaatttaa cgcgaattt   1800
aacaaaatat taacgtttac aatttaaata tttgcttata caatcttcct gttttttggg   1860
cttttctgat tatcaaccgg ggtacatatg attgacatgc tagttttacg attaccgttc   1920
atcgattctc ttgtttgctc cagactctca ggcaatgacc tgatagcctt tgtagagacc   1980
tctcaaaaat agctaccctc tccggcatga atttatcagc tagaacggtt gaatatcata   2040
ttgatggtga tttgactgtc tccggccttt ctcacccgtt tgaatcttta cctacacatt   2100
actcaggcat tgcatttaaa atatatgagg gttctaaaaa ttttttatcct tgcgttgaaa   2160
taaaggcttc tcccgcaaaa gtattacagg gtcataatgt ttttggtaca accgatttag   2220
ctttatgctc tgaggcttta ttgcttaatt ttgccttgc ctgtatgatt   2280
tattggatgt tggaattcct gatgcggtat tttctcctta cgcatctgtg cggtatttca   2340
caccgcatat ggtgcactct cagtacaatc tgctctgatg ccgcatagtt aagccagccc   2400
cgacacccgc caacacccgc tgacgcgccc tgacgggctt gtctgctccc ggcatccgct   2460
tacagacaag ctgtgaccgt ctccgggagc tgcatgtgtc agaggttttc accgtcatca   2520
ccgaaacgcg cgagacgaaa gggcctcgtg atacgcctat ttttataggt taatgtcatg   2580
ataataatgg tttcttagac gtcaggtggc acttttcggg gaaatgtgcg cggaaccct   2640
atttgtttat ttttctaaat acattcaaat atgtatccgc tcatgagaca ataaccctga   2700
taaatgcttc aataattattg aaaaaggaag agtatgagta ttcaacattt ccgtgtcgcc   2760
cttattccct tttttgcggc attttgcctt cctgtttttg ctcacccaga aacgctggtg   2820
aaagtaaaag atgctgaaga tcagttgggt gcacgagtgg gttacatcga actggatctc   2880
aacagcggta agatccttga gagttttcgc cccgaagaac gttttccaat gatgagcact   2940
tttaaagttc tgctatgtgg cgcggtatta tcccgtattg acgccgggca agagcaactc   3000
ggtcgccgca tacactattc tcagaatgac ttggttgagt actcaccagt cacagaaaag   3060
catcttacgg atggcatgac agtaagagaa ttatgcagtg ctgccataac catgagtgat   3120
aacactgcgg ccaacttact tctgacaacg atcggaggac cgaaggagct aaccgctttt   3180
ttgcacaaca tgggggatca tgtaactcgc cttgatcgtt gggaaccgga gctgaatgaa   3240
gccataccaa acgacgagcg tgacaccacg atgcctgtag caatggcaac aacgttgcgc   3300
aaactattaa ctggcgaact acttactcta gcttcccggc aacaattaat agactggatg   3360
gaggcggata aagttgcagg accacttctg cgctcggccc ttccggctgg ctggtttatt   3420
gctgataaat ctggagccgg tgagcgtggg tctcgcggta tcattgcagc actggggcca   3480
gatggtaagc cctcccgtat cgtagttatc tacacgacgg ggagtcaggc aactatggat   3540
gaacgaaata gacagatcgc tgagataggt gcctcactga ttaagcattg gtaactgtca   3600
gaccaagttt actcatatat actttagatt gatttaaaac ttcatttta atttaaaagg   3660
atctaggtga agatccttt tgataatctc atgaccaaaa tcccttaacg tgagttttcg   3720
ttccactgag cgtcagaccc cgtagaaaag atcaaaggat cttcttgaga tcctttttt   3780
ctgcgcgtaa tctgctgctt gcaaacaaaa aaccaccgc taccagcggt ggtttgtttg   3840
ccggatcaag agctaccaac tctttttccg aaggtaactg gcttcagcag agcgcagata   3900
ccaaatactg tccttctagt gtagccgtag ttaggccacc acttcaagaa ctctgtagca   3960
ccgcctacat acctcgctct gctaatcctg ttaccagtgg ctgctgccag tggcgataag   4020
tcgtgtctta ccgggttgga ctcaagacga tagttaccgg ataaggcgca gcggtcgggc   4080
tgaacggggg gttcgtgcac acagcccagc ttggagcgaa cgacctacac cgaactgaga   4140
tacctacagc gtgagctatg agaaagcgcc acgcttcccg aagggagaaa ggcggacagg   4200
tatccggtaa gcggcagggt cggaacagga gagcgcacga gggagcttcc agggggaaac   4260
gcctggtatc tttatagtcc tgtcgggttt cgccacctct gacttgagcg tcgatttttg   4320
tgatgctcgt cagggggcg gagcctatg aaaaacgcca gcaacgcggc ctttttacgg   4380
ttcctggcct tttgctggcc ttttgctcac atgttctttc ctgcgttatc ccctgattct   4440
gtggataacc gtattaccgc ctttgagtga gctgataccg ctcgccgcag ccgaacgacc   4500
gagcgcagcg agtcagtgag cgaggaagcg gaagagcgcc caatacgcaa accgcctctc   4560
cccgcgcgtt ggccgattca ttaatgcagc agctgcgcgc tcgctcgctc actgaggccg   4620
cccgggcaaa gcccgggcgt cgggcgacct tggtcgcccc ggcctcagtg agcgagcgag   4680
cgcgcagaga gggagtggcc aactccatca ctaggggttc cttgtagtta atgattaacc   4740
cgcatgcta cttatctacg tagccatgct ctaggacatt gattattgac tagtggagtt   4800
ccgcgttaca taacttacgg taaatggccc gcctggctga ccgcccaacg acccccgccc   4860
attgacgtca ataatgacgt atgttcccat agtaacgcca atagggactt tccattgacg   4920
tcaatgggtg gagtatttac ggtaaactgc ccacttggca gtacatcaag tgtatcatat   4980
gccaagtacg cccctattg acgtcaatga cggtaaatgg cccgcctggc attatgccca   5040
gtacatgacc ttatgggact ttcctacttg gcagtacatc tacgtattag tcatcgctat   5100
taccatggtc gaggtgagcc ccacgttctg cttcactctc cccatctccc cccccctccc   5160
acccccaatt ttgtatttat ttatttttta attattttgt gcagcgatgg gggcgggggg   5220
ggggggggc gcgcgccagg cggggcgggg cgggcgaggg ggcggggcgg ggcgaggcgg   5280
agaggtgcgg cggcagccaa tcagagcggc gcgctccgaa agtttccttt tatgcgcgagg   5340
cggcggcggc ggcggcccta taaaagcga agcgcgcggc gggcgggagt cgctgcgcgc   5400
tgccttcgcc ccgtgcccg ctccgccgcc gcctcgcgcc gcccgccccg gctctgactg   5460
```

```
accgcgttac taaaacaggt aagtccggcc tccgcgccgg gttttggcgc ctcccgcggg   5520
cgccccctc ctcacggcga gcgctgccac gtcagacgaa gggcgcagcg agcgtcctga   5580
tccttccgcc cggacgctca ggacagcggc ccgctgctca taagactcgg ccttagaacc   5640
ccagtatcag cagaaggaca ttttaggacg ggacttgggt gactctaggg cactggtttt   5700
ctttccagag agcggaacag gcgaggaaaa gtagtcccct ctcggcgatt ctgcggaggg   5760
atctccgtgg ggcggtgaac gccgatgatg cctctactaa ccatgttcat gttttcttt   5820
ttttttctaca ggtcctgggt gacgaacagg gtaccgccac catgaggggc atgaagctgc   5880
tgggggcgct gctggcactg gcggccctac tgcagggggc cgtgtccctg aagatcgcag   5940
ccttcaacat ccagacattt ggggagacca agatgtccaa tgccaccctc gtcagctaca   6000
ttgtgcagat cctgagccgc tatgacatcg ccctggtcca ggaggtcaga gacagccacc   6060
tgactgccgt ggggaagctg ctggacaacc tcaatcagga tgcaccagac acctatcact   6120
acgtggtcag tgagccactg ggacggaaca gctataagga gcgctacctg ttcgtgtaca   6180
ggcctgacca ggtgtctgcg gtggacagct actactacga tgatggctgc gagccctgcg   6240
ggaacgacac cttcaaccga gagccagcca ttgtcaggtt cttctcccgg ttcacagagg   6300
tcagggagtt tgccattgtt cccctgcatg cggcccggg ggacgcagta gccgagatcg   6360
acgctctcta tgacgtctac ctggatgtcc aagagaaatg gggcttggag gacgtcatgt   6420
tgatgggcga cttcaatgcg ggctgcagct atgtgagacc ctcccagtgg tcatccatcc   6480
gcctgtggac aagcccacc ttccagtggc tgatccccga cagcgctgac accacagcta   6540
cacccacgca ctgtgcctat gacaggatcg tggttgcagg gatgctgctc cgaggcgccc   6600
ttgttcccga ctcggctctt ccctttaact tccaggctgc ctatgcctg agtgaccaac   6660
tggcccaagc catcagtgac cactatccag tggaggtgat gctgaagggc ggatcaggcg   6720
gatcacccaa atcttgtgac aaaactcaca catgcccacc gtgcccagca cctgaactcc   6780
tggggggacc gtcagtcttc ctcttccccc caaaacccaa ggacaccctc atgatctccc   6840
ggacccctga ggtcacatgc gtggtggtg acgtgagcca cgaagaccct gaggtcaagt   6900
tcaactggta cgtggacggc gtggaggtgc ataatgccaa gacaaagccg cgggaggagc   6960
agtacaacag cacgtaccgt gtggtcagcg tcctcaccgt cctgcaccag gactggctga   7020
atggcaagga gtacaagtgc aaggtctcca acaaagcccc cccagccccc atcgagaaaa   7080
ccatctccaa agccaagggg cagccccgag aaccacaggt gtacaccctg cccccatccc   7140
gggaggagat gaccaagaac caggtcagcc tgacctgcct ggtcaaaggc ttctatccca   7200
gcgacatcgc cgtggagtgg gagagcaatg ggcagccgga gaacaactac aagaccacgc   7260
ctcccgtgct ggactccgac ggctccttct tcctctacag caagctcacc gtggacaaga   7320
gcaggtggca gcaggggaac gtcttctcat gctccgtgat gcatgaggct ctgcacaacc   7380
actacacgca gaagagcctc tccctgtctc cgggtaaata g                       7421

SEQ ID NO: 8          moltype = DNA   length = 9284
FEATURE               Location/Qualifiers
source                1..9284
                      mol_type = other DNA
                      organism = synthetic construct
SEQUENCE: 8
ttctagaata atcaacctct ggattacaaa atttgtgaaa gattgactgg tattcttaac   60
tatgttgctc cttttacgct atgtggatac gctgctttaa tgcctttgta tcatgctatt   120
gcttcccgta tggctttcat tttctcctcc ttgtataaat cctggttgct gtctctttat   180
gaggagttgt ggcccgttgt caggcaacgt ggcgtggtgt gcactgtgtt tgctgacgca   240
accccactg gttggggcat tgccaccacc tgtcagctcc tttccgggac tttcgctttc   300
cccctcccta ttgccacggc ggaactcatc gccgcctgcc ttgcccgctg ctggacaggg   360
gctctgtgt tgggcactga caattccgtg gtgttgtcgg ggaaatcatc gtccttttcct   420
tggctgctcg cctgtgttgc cacctggatt ctgcgcggga cgtccttctg ctacgtccct   480
tcggccctca atccagcgga ccttccttcc cgcggcctgc tgccggctct gcggcctctt   540
ccgcgtcttc gccttcgccc tcagacgagt cggatctccc tttgggccgc ctccccgcct   600
aagcttatcg ataccgtcga gatctaactt gtttattgca gcttataatg gttacaaata   660
aagcaatagc atcacaaatt tcacaaataa agcatttttt tcactgcatt ctagttgtgg   720
tttgtccaaa ctcatcaatg tatcttatca tgtctggatc tcgacctcga ctagagcatg   780
gctacgtaga taagtagcat ggcggggtaa tcattaacta caaggaaccc ctagtgatgg   840
agttggccac tccctctctg cgcgctcgct cgctcactga cgcgggcga gcgaaaggtcg   900
cccgacgccc gggctttgcc cgggcggcct cagtgagcga gcgagcgcgc cagctggcgt   960
aatagcgaag aggcccgcac cgatcgccct tcccaacagt tgcgcagcct gaatggcgaa   1020
tggaattcca gacgattgag cgtcaaaatg taggtatttc catgagcgtt tttcctgttg   1080
caatggctgg cggtaatatt gttctggata ttaccagcaa ggccgatagt ttgagttctt   1140
ctactcaggc aagtgatgtt attactaatc aaagaagtat tgcgacaacg gttaatttgc   1200
gtgatggaca gactctttta ctcggtggcc tcactgatta taaaaacact tctcaggatt   1260
ctggcgtacc gttcctgtct aaaatcccctt taatcggcct cctgtttagc tcccgctctg   1320
attctaacga ggaaagcacg ttatacgtgc tcgtcaaagc aaccatagta cgcgccctgt   1380
agcggcgcat taagcgcggc gggtgtggtg gttacgcgca gcgtgaccgc tacacttgcc   1440
agcgccctag cgcccgctcc tttcgctttc ttcccttcct ttctcgccac gttcgccggc   1500
tttccccgtc aagctctaaa tcgggggctc cctttagggt tccgatttag tgctttacgg   1560
cacctcgacc ccaaaaaact tgattagggt gatggttcac gtagtgggcc atcgccctga   1620
tagacggttt ttcgcccttt gacgttggag tccacgttct ttaatagtgg actcttgttc   1680
caaactggaa caacactcaa ccctatctcg gtctattctt ttgatttata agggattttg   1740
ccgatttcgg cctattggtt aaaaaatgag ctgatttaac aaaaatttaa cgcgaatttt   1800
aacaaaatat taacgtttac aatttaaata tttgcttata caatcttcct gttttttgggg   1860
cttttctgat tatcaaccgg ggtacatatg attgacatgc tagttttacg attaccgttc   1920
atcgattctc ttgtttgctc cagactctca ggcaatgacc tgatagcctt gtagagacc   1980
tctcaaaaat agctaccctc tccggcatga atttatcgat gaaacggtt gaatatcata   2040
ttgatggtga tttgactgtc tccggccttt ctcacccgtt tgaatcttta cctacacatt   2100
actcaggcat tgcatttaaa atatatgagg gttctaaaaa tttttatcct tgcgttgaaa   2160
taaaggcttc tcccgcaaaa gtattacagg gtcataatgt ttttggtaca accgatttag   2220
ctttatgctc tgaggcttta ttgcttaatt ttgctaattc tttgccttgc ctgtatgatt   2280
tattggatgt tggaattcct gatgcggtat tttctcctta cgcatctgtg cggtatttca   2340
```

```
caccgcatat ggtgcactct cagtacaatc tgctctgatg ccgcatagtt aagccagccc  2400
cgacacccgc caacacccgc tgacgcgccc tgacgggctt gtctgctccc ggcatccgct  2460
tacagacaag ctgtgaccgt ctccgggagc tgcatgtgtc agaggttttc accgtcatca  2520
ccgaaacgcg cgagacgaaa gggcctcgtg atacgcctat ttttataggt taatgtcatg  2580
ataataatgg tttcttagac gtcaggtggc acttttcggg gaaatgtgcg cggaaccccc  2640
atttgtttat ttttctaaat acattcaaat atgtatccgc tcatgagaca ataaccctga  2700
taaatgcttc aataatattg aaaaaggaag agtatgagta ttcaacattt ccgtgtcgcc  2760
cttattccct tttttgcggc attttgcctt cctgtttttg ctcacccaga aacgctggtg  2820
aaagtaaaag atgctgaaga tcagttgggt gcacgagtgg gttacatcga actggatctc  2880
aacagcggta agatccttga gagttttcgc cccgaagaac gttttccaat gatgagcact  2940
tttaaagttc tgctatgtgg cgcggtatta tcccgtattg acgccgggca agagcaactc  3000
ggtcgccgca tacactattc tcagaatgac ttggttgagt actcaccagt cacagaaaag  3060
catcttacgg atggcatgac agtaagagaa ttatgcagtg ctgccataac catgagtgat  3120
aacactgcgg ccaacttact tctgacaacg atcggaggac cgaaggagct aaccgctttt  3180
ttgcacaaca tgggggatca tgtaactcgc cttgatcgtt gggaaccgga gctgaatgaa  3240
gccataccaa acgacgagcg tgacaccacg atgcctgtag caatggcaac aacgttgcgc  3300
aaactattaa ctggcgaact acttactcta gcttcccggc aacaattaat agactggatg  3360
gaggcggata aagttgcagg accacttctg cgctcggccc ttccggctgg ctggtttatt  3420
gctgataaat ctggagccgg tgagcgtggg tctcgcggta tcattgcagc actggggcca  3480
gatggtaagc cctcccgtat cgtagttatc tacacgacgg ggagtcaggc aactatggat  3540
gaacgaaata gacagatcgc tgagataggt gcctcactga ttaagcattg gtaactgtca  3600
gaccaagttt actcatatat actttagatt gatttaaaac ttcattttta atttaaaagg  3660
atctaggtga agatcctttt tgataatctc atgaccaaaa tcccttaacg tgagttttcg  3720
ttccactgag cgtcagaccc cgtagaaaag atcaaaggat cttcttgaga tcctttttt  3780
ctgcgcgtaa tctgctgctt gcaaacaaaa aaaccaccgc taccagcggt ggtttgtttg  3840
ccggatcaag agctaccaac tctttttccg aaggtaactg gcttcagcag agcgcagata  3900
ccaaatactg tccttctagt gtagccgtag ttaggccacc acttcaagaa ctctgtagca  3960
ccgcctacat acctcgctct gctaatcctg ttaccagtgg ctgctgccag tggcgataag  4020
tcgtgtctta ccgggttgga ctcaagacga tagttaccgg ataaggcgca gcggtcgggc  4080
tgaacggggg gttcgtgcac acagcccagc ttggagcgaa cgacctacac cgaactgaga  4140
tacctacagc gtgagctatg agaaagcgcc acgcttcccg aagggagaaa ggcggacagg  4200
tatccggtaa gcggcagggt cggaacagga gagcgcacga gggagcttcc agggggaaac  4260
gcctggtatc tttatagtcc tgtcgggttt cgccacctct gacttgagcg tcgatttttg  4320
tgatgctcgt caggggggcg gagcctatgg aaaaacgcca gcaacgcggc cttttacgg  4380
ttcctggcct tttgctggcc ttttgctcac atgttctttc ctgcgttatc ccctgattct  4440
gtggataacc gtattaccgc ctttgagtga gctgataccg ctcgccgcag ccgaacgacc  4500
gagcgcagcg agtcagtgag cgaggaagcg gaagagcgcc caatacgcaa accgcctctc  4560
cccgcgcgtt ggccgattca ttaatgcagc agctgcgcgc tcgctcgctc actgaggccg  4620
cccgggcaaa gcccgggcgt cgggcgacct ttggtcgccc ggcctcagtg agcgagcgag  4680
cgcgcagaga gggagtggcc aactccatca ctaggggttc cttgtagtta atgattaacc  4740
cgccatgcta cttatctacg tagccatgct ctaggacatt gattattgac tagtggagtt  4800
ccgcgttaca taacttacgg taaatggccc gcctggctga ccgcccaacg accccgcc  4860
attgacgtca ataatgacgt atgttcccat agtaacgcca ataggggactt tccattgacg  4920
tcaatgggtg gagtatttac ggtaaactgc ccacttggca gtacatcaag tgtatcatat  4980
gccaagtacg ccccctattg acgtcaatga cggtaaatgg cccgcctggc attatgccca  5040
gtacatgacc ttatgggact ttcctacttg gcagtacatc tacgtattag tcatcgctat  5100
taccatggtc gaggtgagcc ccacgttctg cttcactctc cccatctccc ccccctcccc  5160
acccccaatt ttgtatttat ttatttttta attattttgt gcagcgatgg ggcgggggg  5220
ggggggggc gcgcgccagg cggggcgggg cgggcgagg ggcggggcgg ggcgaggcgg  5280
agaggtgcgc cggcagccaa tcagagcggc gcgctccgaa agtttccttt tatgcgcagg  5340
cggcggcggc ggcggcccta taaaaagcga agcgcgcggc gggcggcggagt cgctgcgcgc  5400
tgccttcgcc ccgtgccccg ctccgccgcc gcctcgcgcc gcccgccccg gctctgactg  5460
accgcgttac taaaacaggt aagtccggcc tccgcgccgg gttttggcgc ctcccgcggg  5520
cgccccctc ctcacggcga gcgctgccac gtcagacgaa gggcgcagcg agcgtcctga  5580
tccttccgcc cggacgctca ggacagcggc ccgctgctca taagactcgg ccttagaacc  5640
ccagtatcag cagaaggaca ttttaggacg ggacttgggt gactctaggg cactggtttt  5700
ctttccagag agcggaacag gcgaggaaaa gtagtccctt ctcggcgatt ctgcggaggg  5760
atctccgtgg ggcggtgaac gccgatgatg cctctactaa ccatgttcat gttttctttt  5820
tttttctaca ggtcctgggt gacgaacagg gtaccgccac cgccagaccc tgccgtgcat  5880
ttattttttgg ggcggcctgc tgccgtttgg gcgagcagca ccaccaaatg  5940
caccgtgagc catgaagtgg cggattcag ccatctgaaa ctgacccagg tgccggatga  6000
tctgccgacc aacattaccg tgctgaacct gacccataac cagctgcgcc gcctgccggc  6060
ggcgaacttt accgctata gccagctgac cagcctggat gtgggcttta acaccattag  6120
caaactggaa ccggaactgt gccagaaact gccgatgctg aaagtgctga acctgcagca  6180
taacgaactg agccagctga gcgataaaac ctttgcgttt tgcaccaacc tgaccgaact  6240
gcatctgatg agcaacagca ttcagaaaat taaaacaac ccgtttgtga aacagaaaaa  6300
cctgattacc ctggatctga gccataacgg cctgagcagc accaaactgg gcacccaggt  6360
gcagctggaa aacctgcagg aactgctgct gagcaacaac aaaattcagg cgctgaaaag  6420
cgaagaactg agatattttg cgaacagcag cctgaaactg aactgacga gcagcaacca  6480
gattaaagaa tttagcccgg gctgctttca tgcgattggc cgcctgttttg gcctgtttct  6540
gaacaacgtg cagctgggcc cgagcctgac cgaaaaactg tgcctggaac tggcgaacac  6600
cagcattcgc aacctgagcc tgagcaacag ccagctgagc accaccagca acaccacctt  6660
tctgggcctg aaatggacca acctgaccat gctggatctg agctataaca acctgaacgt  6720
ggtgggcaac gatgctttg cgtggctgcc gcagctggaa tattttttc tggaatataa  6780
caacattcag catctgtttta gccatagcct gcatgcctg tttaacgtgc gctatctgaa  6840
cctgaaacgc agctttacca aacagagcat tagcctggcg agcctgccga aaattgatga  6900
ttttagcttt cagtggctga atgcctggga acatctgaac atggaagata cgatattcc  6960
gggcattaaa agcaacatgt ttaccggcct gattaacctg aaatatctga gcctgagcaa  7020
cagctttacc agcctgcgca ccctgaccaa cgaaaccttt gtgagcctgg cgcatagccc  7080
```

```
gctgcatatt ctgaacctga ccaaaaacaa aattagcaaa attgaaagcg atgcgtttag   7140
ctggctgggc catctggaag tgctggatct gggcctgaac gaaattggcc aggaactgac   7200
cggccaggaa tggcgcggcc tggaaaacat ttttgaaatt tatctgagct ataacaaata   7260
tctgcagctg acccgcaaca gctttgcgct ggtgccgagc ctgcagcgcc tgatgctgcg   7320
ccgcgtggcg ctgaaaaacg tggatagcag cccgagcccg tttcagccgc tgcgcaacct   7380
gaccattctg gatctgagca acaacaacat tgcgaacatt aacgatgata tgctggaagg   7440
cctggaaaaa ctggaaattc tggatctgca gcataacaac ctggcgcgcc tgtgcaaaca   7500
tgcgaacccg ggcggcccga tttattttct gaaaggcctg agccatctgc atattctgaa   7560
cctggaaagc aacggctttg atgaaattcc ggtggaagtg tttaaagatc tgtttgaact   7620
gaaaattatt gatctgggcc tgaacaacct gaacaccctg ccggcgagcg tgtttaacaa   7680
ccaggtgagc ctgaaaagcc tgaacctgca gaaaaacctg attaccagcg tggaaaaaaa   7740
agtgtttggc ccggcgtttc gcaacctgac cgaactggat atgcgcttta cccgtttga   7800
ttgcacctgc gaaagcattg cgtggtttgt gaactggatt aacgaaaccc ataccaacat   7860
tccggaactg agcagccatt atctgtgcaa caccccgccg cattatcatg gctttccggt   7920
gcgcctgttt gataccagca gctgcaaaga tagcgcgccg tttgaactgt ttttttatgat   7980
taacaccagc attctgctga ttttatttt tattgtgctg ctgattcatt ttgaaggctg   8040
gcgcattagc ttttattgga acgtgagcgt gcatcgcgtg ctgggcttta agaaattga   8100
tcgccagacc gaacagtttg aatatgcggc gtatattatt catgcgtata aagataaaga   8160
ttgggtgtgg aacatttta gcagcatgga aaaagaagat cagagcctga aattttgcct   8220
ggaagaacgc gattttgaag cgggcgtgtt tgaactggaa gcgattgtga acagcattaa   8280
acgcagccgc aaaattattt ttgtgattac ccatcatctg ctgaaagatc cgctgtgcaa   8340
acgcttttaaa gtgcatcatg cggtgcagca ggcgattgaa cagaacctgg atagcattat   8400
tctggtgtgtt ctggaagaaa ttccggatta taaactgaaa catgcgctgt gcctgcgccg   8460
cggcatgttt aaaagccatt gcattctgaa ctggccggtg cagaaagaac gcattggcgc   8520
gtttcgccat aaactgcagg tggcgctggg cagcaaaaac agcgtgcatg gcggatcag   8580
gcggatcacc caaatcttgt gacaaaactc acacatgcca ccgtgccca gcacctgaac   8640
tcctgggggg accgtcagtc ttcctcttcc ccccaaaacc caaggacacc ctcatgatct   8700
cccggacccc tgaggtcaca tgcgtggtgg tggacgtgag ccacgaagac cctgaggtca   8760
agttcaactg gtacgtggac ggcgtggagg tgcataatgc caagacaaag ccgcggggag   8820
agcagtacaa cagcacgtac cgtgtggtca gcgtcctcac cgtcctgcac caggactggc   8880
tgaatggcaa ggagtacaag tgcaaggtct ccaacaaagc cctcccagcc cccatcgaga   8940
aaaccatctc caaagccaaa gggcagcccc gagaaccaca ggtgtacacc ctgcccccat   9000
cccgggagga tgaccaagaa ccaggtca gcctgacctg cctggtcaaa ggcttctatc   9060
ccagcgacat cgccgtggag tgggagagca atgggcagcc ggagaacaac tacaagacca   9120
cgcctcccgt gctggactcc gacggctcct tcttcctcta cagcaagctc accgtggaca   9180
agagcaggtg gcagcagggg aacgtcttct catgctccgt gatgcatgag gctctgcaca   9240
accactacac gcagaagagc ctctccctgt ctccgggtaa atag                    9284

SEQ ID NO: 9           moltype = DNA   length = 9738
FEATURE                Location/Qualifiers
source                 1..9738
                       mol_type = other DNA
                       organism = synthetic construct
SEQUENCE: 9
ttctagaata atcaacctct ggattacaaa atttgtgaaa gattgactgg tattcttaac     60
tatgttgctc cttttacgct atgtggatac gctgctttaa tgcctttgta tcatgctatt    120
gcttcccgta tggcttttcat tttctcctcc ttgtataaat cctggttgct gtctctttat    180
gaggagttgt ggcccgttgt caggcaacgt ggcgtggtgt gcactgtgtt tgctgacgca    240
accccactg gttggggcat tgccaccacc tgtcagctcc tttccgggac tttcgctttc    300
cccctcccta ttgccacggc ggaactcatc gccgcctgcc ttgcccgctg ctggacaggg    360
gctctggttg tgggcactga caattccgtg gtgttgtcgg ggaaatcatc gtcctttcct    420
tggctgctcg cctgtgttgc cacctggatt ctgcgcggga cgtccttctg ctacgtccct    480
tcggccctca atccagcgga ccttccttcc cgcggcctgc tgccggctct gcggcctctt    540
ccgcgtcttc gccttcgccc tcagacgagt cggatctccc tttgggccgc ctccccgcct    600
aagcttatcg ataccgtcga gatctaactt gtttattgca gcttataatg gttacaaata    660
aagcaatagc atcacaaatt tcacaaataa agcatttttt tcactgcatt ctagttgtgg    720
tttgtccaaa ctcatcaatg tatcttatca tgtctggatc tcgacctcga ctagagcatg    780
gctacgtaga taagtagcat ggcgggttaa tcattaacta caaggaaccc ctagtgatgg    840
agttggccac tccctctctg cgcgctcgct cgctcactga ggccgggcga ccaaaggtcg    900
cccgacgccc gggctttgcc cgggcggcct cagtgagcga gcgagcgcgc cagctgggcgt    960
aatagcgaag aggcccgcac cgatcgccct tcccaacagt tgcgcagcct gaatggcgaa   1020
tggaattcca gacgattgag cgtcaaaatg taggtatttc catgagcgtt tttcctgttg   1080
caatggctgg cggtaatatt gttctggata ttaccagcaa ggccgatagt ttgagttctt   1140
ctactcaggc aagtgatgtt attactaatc aagaagtat tgcgacaagt gttaattgc   1200
gtgatggaca gactctttta ctcggtggcc tcactgatta taaaaacact tctcaggatt   1260
ctggcgtacc gttcctgtct aaaatccctt taatcggcct cctgtttagc tcccgctctg   1320
attctaacga ggaaagcacg ttatacgtgt cgtcaaagc aaccatagta cgcgccctgt   1380
agcggcgcat taagcgcggc gggtgtggtg gttacgcgca gcgtgaccgc tacacttgcc   1440
agcgccctag cgcccgctcc tttcgctttc ttcccttcct ttctcgccac gttcgccggc   1500
tttccccgtc aagctctaaa tcgggggctc cctttagggt tccgatttag tgctttacgg   1560
cacctcgacc ccaaaaaact tgattagggt gatggttcac gtagtgggcc atcgccctga   1620
tagacgtttt tcgccctttt gacgttggag tccacgttct ttaatagtgg actcttgttc   1680
caaactggaa caacactcaa ccctatctcg gtctattctt ttgatttata gggattttg   1740
ccgatttcgg cctattggtt aaaaatgag ctgatttaac aaaaatttaa cgcgaattt   1800
aacaaaatat taacgtttac aatttaaata tttgcttata caatcttcct gttttttggg   1860
cttttctgat tatcaaccgg ggtacatatg attgacatgc tagttttacg attaccgttc   1920
atcgattctc ttgtttgctc cagactctca ggcaatgacc tgatagcctt gtagagacc   1980
tctcaaaaat agctaccctc tccggcatga atttatcagc tagaacggtt gaatatcata   2040
ttgatggtga tttgactgtc tccggccttt ctcacccgtt tgaatcttta cctacacatt   2100
```

-continued

```
actcaggcat tgcatttaaa atatatgagg gttctaaaaa ttttttatcct tgcgttgaaa  2160
taaaggcttc tcccgcaaaa gtattacagg gtcataatgt ttttggtaca accgatttag  2220
ctttatgctc tgaggcttta ttgcttaatt ttgctaattc tttgccttgc ctgtatgatt  2280
tattggatgt tggaattcct gatgcggtat tttctcctta cgcatctgtg cggtatttca  2340
caccgcatat ggtgcactct cagtacaatc tgctctgatg ccgcatagtt aagccagccc  2400
cgacacccgc caacacccgc tgacgcgccc tgacgggctt gtctgctccc ggcatccgct  2460
tacagacaag ctgtgaccgt ctccgggagc tgcatgtgtc agaggttttc accgtcatca  2520
ccgaaacgcg cgagacgaaa gggcctcgtg atacgcctat ttttataggt taatgtcatg  2580
ataataatgg tttcttagac gtcaggtggc acttttcggg gaaatgtgcg cggaacccct  2640
atttgtttat ttttctaaat acattcaaat atgtatccgc tcatgagaca ataaccctga  2700
taaatgcttc aataatattg aaaaaggaag agtatgagta ttcaacattt ccgtgtcgcc  2760
cttattccct tttttgcggc attttgcctt cctgtttttg ctcacccaga aacgctggtg  2820
aaagtaaaag atgctgaaga tcagttgggt gcacgagtgg gttacatcga actggatctc  2880
aacagcggta agatccttga gagttttcgc cccgaagaac gttttccaat gatgagcact  2940
tttaaagttc tgctatgtgg cgcggtatta tcccgtattg acgccgggca agagcaactc  3000
ggtcgccgca tacactattc tcagaatgac ttggttgagt actcaccagt cacagaaaag  3060
catcttacgg atggcatgac agtaagagaa ttatgcagtg ctgccataac catgagtgat  3120
aacactgcgg ccaacttact tctgacaacg atcggaggac cgaaggagct aaccgctttt  3180
ttgcacaaca tgggggatca tgtaactcgc cttgatcgtt gggaaccgga gctgaatgaa  3240
gccataccaa acgacgagcg tgacaccacg atgcctgtag caatggcaac aacgttgcgc  3300
aaactattaa ctggcgaact acttactcta gcttcccggc aacaattaat agactggatg  3360
gaggcggata aagttgcagg ccacttctg cgctcggccc ttccggctgg ctggtttatt  3420
gctgataaat ctggagccgg tgagcgtggg tctcgcggta tcattgcagc actggggcca  3480
gatggtaagc cctcccgtat cgtagttatc tacacgacgg ggagtcaggc aactatggat  3540
gaacgaaata gacagatcgc tgagataggt gcctcactga ttaagcattg gtaactgtca  3600
gaccaagttt actcatatat actttagatt gatttaaaac ttcatttta atttaaaagg  3660
atctaggtga agatcctttt tgataatctc atgaccaaaa tcccttaacg tgagttttcg  3720
ttccactgag cgtcagaccc cgtagaaaag atcaaaggat cttcttgaga tcctttttt  3780
ctgcgcgtaa tctgctgctt gcaaacaaaa aaaccaccgc taccagcggt ggtttgtttg  3840
ccggatcaag agctaccaac tctttttccg aaggtaactg gcttcagcag agcgcagata  3900
ccaaatactg tccttctagt gtagccgtag ttaggccacc acttcaagaa ctctgtagca  3960
ccgcctacat acctcgctct gctaatcctg ttaccagtgg ctgctgccag tggcgataag  4020
tcgtgtctta ccgggttgga ctcaagacga tagttaccgg ataaggcgca gcggtcgggc  4080
tgaacggggg gttcgtgcac acagcccagc ttggagcgaa cgacctacac cgaactgaga  4140
tacctacagc gtgagctatg agaaagcgcc acgcttcccg aaggagaaa ggcggacagg  4200
tatccggtaa gcggcagggt cggaacagga gagcgcacga gggagcttcc agggggaaac  4260
gcctggtatc tttatagtcc tgtcgggttt cgccacctct gacttgagcg tcgatttttg  4320
tgatgctcgt caggggggcg gagcctatgg aaaaacgcca gcaacgcggc cttttacgg  4380
ttcctggcct tttgctgcc ttttgctcac atgttctttc ctgcgttatc ccctgattct  4440
gtggataacc gtattaccgc ctttgagtga gctgataccg ctcgccgcag ccgaacgacc  4500
gagcgcagcg agtcagtgag cgaggaagcg gaagagcgcc caatacgcaa accgcctctc  4560
cccgcgcgtt ggccgattca ttaatgcagc agctgcgcgc tcgctcgctc actgaggccg  4620
cccgggcaaa gcccgggcgt cgggcgacct ttggtcgccc agcgagcgag  4680
cgcgcagaga gggagtggcc aactccatca ctaggggttc cttgtagtta atgattaacc  4740
cgccatgcta cttatctacg tagccatgct ctaggacatt gattattgac tagtggagtt  4800
ccgcgttaca taacttacgg taaatggccc gcctggctga ccgcccaacg acccccgccc  4860
attgacgtca ataatgacgt atgttcccat agtaacgcca atagggactt tccattgacg  4920
tcaatgggtg gagtatttac ggtaaactgc ccacttggca gtacatcaag tgtatcatat  4980
gccaagtacg cccccctattg acgtcaatga cggtaaatgg cccgcctggc attatgccca  5040
gtacatgacc ttatgggact ttcctacttg gcagtacatc tacgtattag tcatcgctat  5100
taccatggtc gaggtgagcc ccacgttctg cttcactctc cccatctccc cccctctccc  5160
acccccaatt ttgtatttat ttattttta attattttgt gcagcgatgg gggcgggggg  5220
gggggggggc gcgcgccagg cggggcgggg cgggcgagg ggcggggcgg ggcgaggcgg  5280
agaggtgcgc cggcagccaa tcagagcggc gcgctccgaa agtttccttt tatggcgagg  5340
cggcggcggc ggcggcccta taaaaagcga agcgcgcggc gggcggggagt cgctgcgcgc  5400
tgccttcgcc ccgtgcccg ctccgccgcc gcctcgcgcc gcccgcccg gctctgactg  5460
accgcgttac taaaacaggt aagtccggcc tccgcgccgg gttttggcgc ctcccgcggg  5520
cgcccccctc ctcacggcga cgctgccac gtcagacgaa gggcgcagcg agcgtcctga  5580
tccttccgcc cggacgctca ggacagcggc ccgctgctca taagactcag ccttagaacc  5640
ccagtatcag cagaaggaca ttttaggacg ggacttgggt gactctaggg cactggtttt  5700
ctttccagag agcggaacag gcgaggaaaa gtagtcccct tcggcgatt ctgcggaggg  5760
atctccgtgg ggcggtgaac gccgatgatg cctctactaa ccatgttcat gttttctttt  5820
tttttctaca ggtcctgggt gacgaacagg gtaccgccac catgagggc atgaagctgc  5880
tgggggcgct gctggcactg gcggccctac tgcaggggc cgtgtccatg ggcttttgc  5940
gcagcgcgct gcatccgctg agcctgctgg tgcaggcgat tatgctgcg atgaccctgg  6000
cgctgggcac cctgccggcg tttgccgt gcgaactgca gccgcatggc ctggtgaact  6060
gcaactggct gtttctgaaa gcgtgccgc atttagcat ggcggcgccg cgcggcaacg  6120
tgaccagcct gagcctgagc agcaaccgca ttcatcatct gcatgatgcc gattttgcgc  6180
atctgccgag cctgcgccat ctgaacctga aatgaactg cccgccggtg ggcctgagcc  6240
cgatgcattt tccgtgccat atgaccattg aaccgagcac ctttctggcg gtgccgaccc  6300
tggaagaact gaacctgagc tataacaaca ttatgaccgt gccggcgctg ccgaaaagcc  6360
tgattagcct gagcctgagc cataccaaca ttctgatgct ggatagcgcg agcctggcgg  6420
gcctgcatgc gctgcgcttt ctgtttatgg atggcaactg ctattataaa aacccgtgcc  6480
gccaggcgct ggaagtgcg ccgggcgcgc tgcgggcgc acccatctga  6540
ggctgaaata taacaacctg accgtgtgc gcgcaacct gccgagcagc tggaatatc  6600
tgctgctgag ctataaccgc attgtgaaac tggcgccgga agatctgcg aacctgaccg  6660
cgctgcgcgt gctggatgtg gcggcaact gccgccgctg cgatcatgcg ccgaacccgt  6720
gcatggaatg cccgcgccat tttccgcagc tgcatccgga tacctttagc catctgagcc  6780
gcctggaagg cctggtgctg aaagatagca gcctgagctg gctgaacgcg agctggtttc  6840
```

```
gcggcctggg caacctgcgc gtgctggatc tgagcgaaaa ctttctgtat aaatgcatta   6900
ccaaaaccaa agcgtttcag ggcctgaccc agctgcgcaa actgaacctg agctttaact   6960
atcagaaacg cgtgagcttt gcgcatctga gcctggcgcc gagctttggc agcctggtgg   7020
cgctgaaaga actggatatg catggcattt tttttcgcag cctggatgaa accaccctgc   7080
gcccgctggc gcgcctgccg atgctgcaga ccctgcgcct gcagatgaac tttattaacc   7140
aggcgcagct gggcattttt cgcgcgtttc cgggcctgcg ctatgtggat ctgagcgata   7200
accgcattag cggcgcgagc gaactgaccg cgaccatggg cgaagcggat ggcggcgaaa   7260
aagtgtggct gcagccgggc gatctggcgc cggcgccggt ggatacccg agcagcgaag   7320
attttcgccc gaactgcagc accctgaact ttaccctgga tctgagccgc aacaacctgg   7380
tgaccgtgca gccggaaatg tttgcgcagc tgagccatct gcagtgcctg cgcctgagcc   7440
ataactgcat tagccaggcg gtgaacggca gccagtttct gccgctgacc ggcctgcagg   7500
tgctggatct gagccataac aaactggatc tgtatcatga acatagcttt accgaactgc   7560
cgcgcctgga agcgctggat ctgagctata acagccagcc gtttggcatg cagggcgtgg   7620
gccataactt tagctttgtg gcgcatctgc gcaccctgcc ccatctgagc ctggcgcata   7680
acaacattca tagccaggtg agccagcagc tgtgcagcac cagcctgcgc gcgctggatt   7740
ttagcggcaa cgcgctgggc catatgtggg cggaagcgga tctgtatctg cattttttc   7800
agggcctgag cggcctgatt tggctggatc tgagccagaa ccgcctgcat accctgctgc   7860
cgcagaccct gcgcaacctg ccgaaaagcc tgcaggtgct gcagctgtgc gataactatc   7920
tggcgttttt taaatggtgg agcctgcatt ttctgccgaa actggaagtg ctggatctgg   7980
cgggcaacca gctgaaagcg ctgaccaacg gcagcctgcc ggcgggcacc cgcctgcgcc   8040
gcctggatgt gagctgcaac agcattagct tgtggcgcc gggcttttt agcaaagcga   8100
aagaactgcg cgaactgaac ctgagcgcga acgcgctgga caagcgtggt catagctggt   8160
ttggcccgct ggcgagcgcg ctgcagattc tggatgtgag cgcgaacccg ctgcattgg   8220
cgtgcggcgc ggcgtttatg gattttctgc tggaagtgca ggcggcggtg ccgggcctgc   8280
cgagccgcgt gaaatgcggc agcccgggcc agctgcaggg cctgagcatt tttgcgcagg   8340
atctgcgcct gtgcctggat gaagcgctga gctgggattg ctttgcgctg agcctgctga   8400
cggtggcgct gggcctgggc gtgccgatgc tgcatcatct gtgcggctgg gatctgtggt   8460
attgctttca tctgtgcctg gcgtggctgc cgtggcgcgg ccgccagagc ggccgcgatg   8520
aagatgcgct gccgtatgat gcgtttgtgg tgtttgataa acccagagc gcggtggcgg   8580
attgggtgta taacgaactg cgcggccagc tggaagaatg ccgcggccgc tgggcgctgc   8640
gcctgtgcct ggaagaacgc gattggctgc cgggcaaaaa cctgtttgaa aacctgtggg   8700
cgagcgtgta tggcagccgc aaaaccctgt tgtgctggc gcataccgat cgcgtgagcg   8760
gcctgctgcg cgcgagcttt ctgctggcgc agcagcgcct gctggaagat cgcaaagatg   8820
tggtggtgct ggtgattctg agcccggatg gccgccgcag ccgctatgtg cgcctgcgcc   8880
agcgcctgtg ccgccagagc gtgctgctgt ggccgcatca gccgagcgcc cagcgcagct   8940
tttgggcgca gctgggcatg cgcgctgaccc gcgataacca tcatttttat aaccgcaact   9000
tttgccaggg cccgaccgcg gaagggcgga tcaggcggat cacccaaatc ttgtgacaaa   9060
actcacacat gcccaccgtg cccagcacct gaactcctgg ggggaccgtc agtcttcctc   9120
ttccccccca aacccaagga cacccctcatg atctcccga ccccctgaggt cacatgcgtg   9180
gtggtggacg tgagccacga agaccctgag gtcaagttca actggtacgt ggacggcgtg   9240
gaggtgcata atgccaagac aaagccgcgg gaggagcagt acaacagcac gtaccgtgtg   9300
gtcagcgtcc tcaccgtcct gcaccaggac tggctgaatg gcaaggagta caagtgcaag   9360
gtctccaaca agccctccc agcccccatc gagaaaacca tctccaaagc caaagggcag   9420
ccccgagaac cacaggtgta caccctgccc ccatcccggg aggagatgac caagaaccag   9480
gtcagcctga cctgcctggt caaaggcttc tatcccagcg acatcgccgt ggagtgggag   9540
agcaatgggc agccggagaa caactacaag accacgcctc ccgtgctgga ctccgacggc   9600
tccttcttcc tctacagcaa gctcaccgtg gacaagagca ggtggcagca ggggaacgtc   9660
ttctcatgct ccgtgatgca tgaggctctg cacaaccact acacgcagaa gagcctctcc   9720
ctgtctccgg gtaaatag                                                 9738
```

| SEQ ID NO: 10 | moltype = DNA   length = 7364 |
|---|---|
| FEATURE | Location/Qualifiers |
| source | 1..7364 |
|  | mol_type = other DNA |
|  | organism = synthetic construct |

SEQUENCE: 10

```
ttctagaata atcaacctct ggattacaaa atttgtgaaa gattgactgg tattcttaac   60
tatgttgctc cttttacgct atgtggatac gctgctttaa tgcctttgta tcatgctatt   120
gcttcccgta tggctttcat tttctcctcc ttgtataaat cctggttgct gtctctttat   180
gaggagttgt ggcccgttgt caggcaacgt ggcgtggtgt gcactgtgtt tgctgacgca   240
acccccactg gttggggcat tgccaccacc tgtcagctcc tttccgggac tttcgctttc   300
ccctcccta ttgccacggc ggaactcatc gccgcctgcc ttgcccgctg ctggacaggg   360
gctcggctgt tgggcactga caattccgtg gtgttgtcgg ggaaatcatc gtcctttcct   420
tggctgctcg cctgtgttgc cacctggatt ctgcgcggga cgtccttctg ctacgtccct   480
tcggccctca atccagcgga ccttccttcc cgcggcctgc tgccggctct gcggcctctt   540
ccgcgtcttc gccttcgccc tcagacgagt cggatctccc tttgggccgc ctccccgcct   600
aagcttatcg ataccgtcga gatctaactt gtttattgca gcttataatg gttacaaata   660
aagcaatagc atcacaaatt tcacaaataa agcatttttt tcactgcatt ctagttgtgg   720
tttgtccaaa ctcatcaatg tatcttatca tgtctggatc tcgacctcga ctagagcatg   780
gctacgtaga taagtagcat ggcgggttaa tcattaacta caaggaaccc ctagtgatgg   840
agttggccac tccctctctg cgcgctcgct cgctcactga ggccgggcga ccaaaggtcg   900
cccgacgccc gggctttgcc cgggcggcct cagtgagcga gcgagcgcgc agctggcgt   960
aatagcgaag aggcccgcac cgatcgccct tcccaacagt tgcgcagcct gaatggcgaa   1020
tggaattcca gacgattgag cgtcaaaatg taggtatttc catgagcgtt tttcctgttg   1080
caatggctgg cggtaatatt gttctggata ttaccagcaa ggccgatagt ttgagttctt   1140
ctactcaggc aagtgatgtt attactaatc aaagaagtat tgcgacaacg ttaatttgc   1200
gtgatggaca gactcttta ctcggtggcc tcactgatta taaaaacact ctcaggatt   1260
ctggcgtacc gttcctgtct aaaatccctt taatcggcct cctgtttagc tcccgctctg   1320
attctaacga ggaaagcacg ttatacgtgc tcgtcaaagc aaccatagta cgcgcccgt   1380
```

```
agcggcgcat taagcgcggc gggtgtggtg gttacgcgca gcgtgaccgc tacacttgcc      1440
agcgccctag cgcccgctcc tttcgctttc ttcccttcct ttctcgccac gttcgccggc      1500
tttccccgtc aagctctaaa tcgggggctc cctttagggt tccgatttag tgctttacgg      1560
cacctcgacc ccaaaaaact tgattagggt gatggttcac gtagtgggcc atcgccctga      1620
tagacggttt ttcgcccttt gacgttggag tccacgttct ttaatagtgg actcttgttc      1680
caaactggaa caacactcaa ccctatctcg gtctattctt ttgatttata agggattttg      1740
ccgatttcgg cctattggtt aaaaaatgag ctgatttaac aaaaatttaa cgcgaatttt      1800
aacaaaatat taacgtttac aatttaaata tttgcttata caatcttcct gttttgggg      1860
cttttctgat tatcaaccgg ggtacatatg attgacatgc tagtttttacg attaccgttc      1920
atcgattctc ttgtttgctc cagactctca ggcaatgacc tgatagcctt tgtagagacc      1980
tctcaaaaat agctaccctc tccggcatga atttatcagc tagaacggtt gaatatcata      2040
ttgatggtga tttgactgtc tccggccttt ctcacccgtt tgaatcttta cctacacatt      2100
actcaggcat tgcatttaaa atatatgagg gttctaaaaa tttttatcct tgccgttgaa      2160
taaaggcttc tcccgcaaaa gtattacagg gtcataatgt ttttggtaca accgatttag      2220
ctttatgctc tgaggcttta ttgcttaatt ttgctaattc tttgccttgc ctgtatgatt      2280
tattggatgt tggaattcct gatgcggtat tttctcctta cgcatctgtg cggtatttca      2340
caccgcatat ggtgcactct cagtacaatc tgctctgatg ccgcatagtt aagccagccc      2400
cgacacccgc caacacccgc tgacgggctt gtctgctccc ggcatccgct      2460
tacagacaag ctgtgaccgt ctccgggagc tgcatgtgtc agaggttttc accgtcatca      2520
ccgaaacgcg cgagacgaaa gggcctcgtg tatacgccta ttttataggt taatgtcatg      2580
ataataatgg tttcttagac gtcaggtggc acttttcggg gaaatgtgcg cggaaccct      2640
atttgttat ttttctaaat acattcaaat atgtatccgc tcatgagaca ataaccctga      2700
taaatgcttc aataatattg aaaaaggaag agtatgagta ttcaacattt ccgtgtcgcc      2760
cttattccct tttttgcggc attttgcctt cctgtttttg ctcacccaga aacgctggtg      2820
aaagtaaaag atgctgaaga tcagttgggt gcacgagtgg gttacatcga actggatctc      2880
aacagcggta agatccttga gagttttcgc cccgaagaac gttttccaat gatgagcact      2940
tttaaagttc tgctatgtgg cgcggtatta tcccgtattg acgccgggca agagcaactc      3000
ggtcgccgca tacactattc tcagaatgac ttggttgagt actcaccagt cacagaaaag      3060
catcttacgg atggcatgac agtaagagaa ttatgcagtg ctgccataac catgagtgat      3120
aacactgcgg ccaacttact tctgacaacg atcggaggac cgaaggagct aaccgctttt      3180
ttgcacaaca tgggggatca tgtaactcgc cttgatcgtt gggaaccgga gctgaatgaa      3240
gccataccaa acgacgagcg tgacaccacg atgcctgtag caatggcaac aacgttgcgc      3300
aaactattaa ctggcgaact acttactcta gcttcccggc aacaattaat agactggatg      3360
gaggcggata aagttgcagg accacttctg cgctcggccc ttccggctgg ctggtttatt      3420
gctgataaat ctggagccgg tgagcgtggg tctcgcggta tcattgcagc actggggcca      3480
gatggtaagc cctcccgtat cgtagttatc tacacgacgg ggagtcaggc aactatggat      3540
gaacgaaata gacagatcgc tgagataggt gcctcactga ttaagcattg gtaactgtca      3600
gaccaagttt actcatatat actttagatt gatttaaaac ttcattttta atttaaaagg      3660
atctaggtga agatccttt tgataatctc atgaccaaaa tcccttaacg tgagttttcg      3720
ttccactgag cgtcagaccc cgtagaaaag atcaaaggat cttcttgaga tcctttttt      3780
ctgcgcgtaa tctgctgctt gcaaacaaaa aaaccaccgc taccagcggt ggtttgtttg      3840
ccggatcaag agctaccaac tctttttccg aaggtaactg gcttcagcag agcgcagata      3900
ccaaatactg tccttctagt gtagccgtag ttaggccacc acttcaagaa ctctgtagca      3960
ccgcctacat acctcgctct gctaatcctg ttaccagtgg ctgctgccag tggcgataag      4020
tcgtgtctta ccgggttgga ctcaagacga tagttaccgg ataaggcgca gcggtcgggc      4080
tgaacggggg gttcgtgcac acagcccagc ttggagcgaa cgacctacac cgaactgaga      4140
tacctacagc gtgagctatg agaaagcgcc acgcttcccg aaggagaaa ggcggacagg      4200
tatccggtaa gcggcagggt cggaacagga gagcgcacga gggagcttcc agggggaaac      4260
gcctggtatc tttatagtcc tgtcgggttt cgccacctct gacttgagcg tcgatttttg      4320
tgatgctcgt caggggggcg gagcctatgg aaaaacgcca gcaacgcggc ctttttacgg      4380
ttcctggcct tttgctggcc ttttgctcac atgttcttc ctgcgttatc ccctgattct      4440
gtggataacc gtattaccgc ctttgagtga gctgataccg ctcgccgcag ccgaacgacc      4500
gagcgcagcg agtcagtgag cgaggaagcg gaagagcgcc caatacgcaa accgcctctc      4560
cccgcgcgtt ggccgattca ttaatgcagc agctgcgcgc tcgctcgctc actgaggccg      4620
cccgggcaaa gcccgggcgt cgggcgacct ttggtcgccc ggcctcagtg agcgagcgag      4680
cgcgcagaga gggagtggcc aactccatca ctaggggttc cttgtagtta atgattaacc      4740
cgccatgcta cttatctacg tagccatgct ctaggacatt gattattgac tagtggagtt      4800
ccgcgttaca taacttacgg taaatggccc gcctggctga ccgcccaacg accccgcc      4860
attgacgtca ataatgacgt atgttcccat agtaacgcca ataggggactt tccattgacg      4920
tcaatgggtg gagtatttac ggtaaactgc ccacttggca gtacatcaag tgtatcatat      4980
gccaagtacg ccccctattg acgtcaatga cggtaaatgg cccgcctggc attatgccca      5040
gtacatgacc ttatgggact ttcctacttg gcagtacatc tacgtattag tcatcgctat      5100
taccatggtc gaggtgagcc ccacgttctg cttcactctc cccatctccc cccctcccc      5160
accccaatt ttgtatttat ttatttttta attatttgt gcagcgatgg ggggcggggg      5220
ggggggggc gcgcgccagg cggggcgggg cggggcgagg ggcggggcgg ggcgaggcgg      5280
agaggtgcgg cggcagccaa tcagagcggc gcgctccgaa agtttccttt tatggcgagg      5340
cggcggcggc ggcggcccta taaaagcga agcgcgcggc gggcgggagt cgctgcgcgc      5400
tgccttcgcc ccgtgccccg ctccgccgcc gcctcgcgcc gcccgccccg gctctgactg      5460
accgcgttac taaaacaggt aagtccggcc tccgcgccgg gttttggcgc ctcccgcggg      5520
cgcccccctc ctcacgcgcga gcgctgccac gtcagacgaa gggcgcagcg agcgtcctga      5580
tccttccgcc cggacgctca ggacagcggc ccgctgctca taagactcgg ccttagaacc      5640
ccagtatcag cagaaggaca ttttaggacg ggacttgggt gactctaggg cactggtttt      5700
ctttccagag agcggaacag gcgaggaaaa gtagtcccct ccggcgatt ctgcggaggg      5760
atcctggtgg tcggttgaac gccgatgatg cctctactaa ccatgttcat gttttctttt      5820
tttttctaca ggtcctgggt gacgaacagg gtaccgccac catgagggc atgaagctga      5880
tgggggcgct gctggcactg gcgggcctac tgcagggggc cgtgtccatg agcatgctgt      5940
tttataccct gattaccgcg tttctgattg gcattcaggc ggaaccgcat agcgaaagca      6000
acgtgccggc gggccatacc attccgcagg cgcattggac caaactgcag catagcctgg      6060
ataccgcgct gcgccgcgcg cgcagcgcgc cggcggcggc gattgcggcg cgcgtggcgg      6120
```

```
gccagacccg caacattacc gtggatccgc gcctgtttaa aaaacgccgc ctgcgcagcc  6180
cgcgcgtgct gtttagcacc cagccgccgc gcgaagcggc ggatacccag gatctggatt  6240
ttgaagtggg cggcgcggcg ccgtttaacc gcacccatcg cagcaaacgc agcagcagcc  6300
atccgatttt tcatcgcggc gaatttagcg tgtgcgatag cgtgagcgtg tgggtgggcg  6360
ataaaaccac cgcgaccgat attaaaggca aagaagtgat ggtgctgggc gaagtgaaca  6420
ttaacaacag cgtgtttaaa cagtattttt ttgaaaccaa atgccgcgat ccgaacccga  6480
tggatacgcg ctgccgcggc attgatagca acattggaaa cagctattgc accaccaccc  6540
ataccttgt gaaagcgctg accatggatg gcaaacaggc ggcgtggcgc tttattcgca  6600
ttgataccgc gtgcgtgtgc gtgctgagcc gcaaagcggt gcgcgcgcg ggcggatcag  6660
gcggatcacc caaatcttgt gacaaaactc acacatgccc accgtgccca gcacctgaac  6720
tcctgggggg accgtcagtc ttcctcttcc ccccaaaacc caaggacacc ctcatgatct  6780
cccgacccg tgaggtcaca tgcgtggtgg tggacgtgag ccacgaagac cctgaggtca  6840
agttcaactg gtacgtggac ggcgtggagg tgcataatgc caagacaaag ccgcgggagg  6900
agcagtacaa cagcacgtac cgtgtggtca gcgtcctcac cgtcctgcac caggactggc  6960
tgaatggcaa ggagtacaag tgcaaggtct ccaacaaagc cctcccagcc cccatcgaga  7020
aaaccatctc caaagccaaa gggcagcccc gagaaccaca ggtgtacacc ctgccccat  7080
cccgggagga tgaccaagaa ccaggtca gcctgacctg cctggtcaaa ggcttctatc  7140
ccagcgacat cgccgtggag tgggagagca atgggcagcc ggagaacaac tacaagacca  7200
cgcctcccgt gctggactcc gacggctcct tcttcctcta cagcaagctc accgtggaca  7260
agagcaggtg gcagcagggg aacgtcttct catgctccgt gatgcatgag gctctgcaca  7320
accactacac gcagaagagc ctctccctgt ctccgggtaa atag              7364

SEQ ID NO: 11           moltype = DNA  length = 6972
FEATURE                 Location/Qualifiers
source                  1..6972
                        mol_type = other DNA
                        organism = synthetic construct
SEQUENCE: 11
ttctagaata atcaacctct ggattacaaa atttgtgaaa gattgactgg tattcttaac    60
tatgttgctc cttttacgct atgtggatac gctgctttaa tgcctttgta tcatgctatt   120
gcttcccgta tggctttcat tttctcctcc ttgtataaat cctggttgct gtctctttat   180
gaggagttgt ggcccgttgt caggcaacgt ggcgtggtgt gcactgtgtt tgctgacgca   240
accccactg gttggggcat tgccaccacc tgtcagctcc tttccgggac tttcgctttc   300
cccctcccta ttgccacggc ggaactcatc gccgcctgcc ttgcccgctg ctggacaggg   360
gctcggctgt tgggcactga caattccgtg gtgtttgtcg gaaatcatcg tcctttcct   420
tggctgctcg cctgtgttgc cacctggatt ctgcgcggga cgtccttctg ctacgtccct   480
tcggccctca atccagcgga ccttccttcc cgcggcctgc tgccggctct gcggcctctt   540
ccgcgtcttc gccttcgccc tcagacgagt cggatctccc tttgggccgc ctccccgcct   600
aagcttatcg ataccgtcga gatctaactt gtttattgca gcttataatg gttacaaata   660
aagcaatagc atcacaaatt tcacaaataa agcattttt tcactgcatt ctagttgtgg   720
tttgtccaaa ctcatcaatg tatcttatca tgtctggatc tcgacctcga ctagagcatg   780
gctacgtaga taagtagcat ggcgggttaa tcattaacta caaggaaccc ctagtgatgg   840
agttggccac tccctctctg cgcgctcgct cgctcactga cgcgggggca ccaaaggtcg   900
cccgacgccc gggctttgcc cgggcggcct cagtgagcga gcgagcgcgc cagctggcgt   960
aatagcgaag aggcccgcac cgatcgccct tcccaacagt tgcgcagcct gaatggcgaa  1020
tggaattcca gacgattgag cgtcaaaatg taggtatttc catgagcgtt tttcctgttg  1080
caatgctgg cggtaaatatt gttctggata ttaccagcaa ggccgatagt ttgagttctt  1140
ctactcaggc aagtgatgtt attactaatc aaagaagtat tgcgacaacg gttaatttgc  1200
gtgatggaca gactcttta ctcggtggcc tcactgatta taaaaacact tctcaggatt  1260
ctggcgtacc gttcctgtct aaaatcccct taatcggcct cctgtttagc tcccgctctg  1320
attctaacga ggaaagcacg ttatacgtgc tcgtcaaagc aaccatagta cgcgccctgt  1380
agcggcgcat taagcgcggc gggtgtggtg gttacgcgca gcgtgaccgc tacacttgcc  1440
agcgccctag cgcccgctcc tttcgctttc ttcccttcct ttctcgccac gttcgccggc  1500
tttccccgtc aagctctaaa tcgggggctc cctttagggt tccgatttag tgctttacgg  1560
cacctcgacc ccaaaaaact tgattaggg gatggttcac gtagtgggcc atcgccctga  1620
tagacggttt ttcgcccttt gacgttggag tccacgttct ttaatagtgg actcttgttc  1680
caaactggaa caacactcaa ccctatctcg gtctattctt ttgatttata agggattttg  1740
ccgatttcgg cctattggtt aaaaaatgag ctgatttaac aaaaatttaa cgcgaatttt  1800
aacaaaatat taacgtttac aatttaaata tttgcttata caatcttcct gttttggggg  1860
cttttctgat tatcaaccgg ggtacatatg attgacatgc tagttttacg attaccgttc  1920
atcgattctc ttgtttgctc cagactctca ggcaatgacc tgatagcctt tgtagagacc  1980
tctcaaaaat agctaccctc tccggcatga atttatcagc tagaacggtt gaatatcata  2040
ttgatggtga tttgactgtc tccggccttt ctcacccgtt tgaatcttta cctacacatt  2100
actcaggcat tgcatttaaa atatatgagg gttctaaaaa ttttttatcct tgcgttgaaa  2160
taaaggcttc tcccgcaaaa gtattacagg gtcataatgt tttttggtaca accgatttag  2220
ctttatgctc tgaggcttta ttgcttaatt ttgctaattc tttgccttgc ctgtatgatt  2280
tattggatgt tggaattcct gatgcggtat tttctcctta cgcatctgtg cggtatttca  2340
caccgcatat ggtgcactct cagtacaatc tgctctgatg ccgcatagtt aagccagcc  2400
cgacacccgc caacaccgc tgacgcgcc ctgacgggct tgtctgctcc cggcatccgc  2460
tacagacaag ctgtgaccgt ctccgggagc tgcatgtgtc agaggttttc accgtcatca  2520
ccgaaacgcg cgagacgaaa gggcctcgtg atacgcctat ttttataggt taatgtcatg  2580
ataataatgg tttcttagac gtcaggtggc acttttcggg gaaatgtgcg cggaacccct  2640
atttgtttat ttttctaaat acattcaaat atgtatccgc tcatgagaca ataaccctga  2700
taaatgcttc aataatattg aaaaaggaag agtatgagta ttcaacattt ccgtgtcgcc  2760
cttattccct ttttttgcggc attttgcctt cctgtttttg ctcacccaga aacgctggtg  2820
aaagtaaaag atgctgaaga tcagttgggt gcacgagtgg gttacatcga actggatctc  2880
aacagcggta agatccttga gagttttcgc cccgaagaac gttttccaat gatgagcact  2940
tttaaagttc tgctatgtgg cgcggtatta tcccgtattg acgccgggca agagcaactc  3000
ggtcgccgca tacactattc tcagaatgac ttggttgagt actcaccagt cacagaaaag  3060
```

```
catcttacgg atggcatgac agtaagagaa ttatgcagtg ctgccataac catgagtgat  3120
aacactgcgg ccaacttact tctgacaacg atcggaggac cgaaggagct aaccgctttt  3180
ttgcacaaca tggggatca tgtaactcgc cttgatcgtt gggaaccgga gctgaatgaa   3240
gccataccaa acgacgagcg tgacaccacg atgcctgtag caatggcaac aacgttgcgc   3300
aaactattaa ctggcgaact acttactcta gcttcccggc aacaattaat agactggatg   3360
gaggcggata aagttgcagg accacttctg cgctcggccc ttccggctgg ctggtttatt   3420
gctgataaat ctggagccgg tgagcgtggg tctcgcggta tcattgcagc actggggcca   3480
gatggtaagc cctcccgtat cgtagttatc tacacgacgg ggagtcaggc aactatggat   3540
gaacgaaata gacagatcgc tgagataggt gcctcactga ttaagcattg gtaactgtca   3600
gaccaagttt actcatatat actttagatt gatttaaaac ttcattttta atttaaaagg   3660
atctaggtga agatcctttt tgataatctc atgaccaaaa tcccttaacg tgagttttcg   3720
ttccactgag cgtcagaccc cgtagaaaag atcaaaggat cttcttgaga tcctttttt   3780
ctgcgcgtaa tctgctgctt gcaaacaaaa aaaccaccgc taccagcggt ggtttgtttg   3840
ccggatcaag agctaccaac tcttttccg aaggtaactg gcttcagcag agcgcagata   3900
ccaaatactg tccttctagt gtagccgtag ttaggccacc acttcaagaa ctctgtagca   3960
ccgcctacat acctcgctct gctaatcctg ttaccagtgg ctgctgccag tggcgataag   4020
tcgtgtctta ccgggttgga ctcaagacga tagttaccgg ataaggcgca gcggtcgggc   4080
tgaacggggg gttcgtgcac acagcccagc ttggagcgaa cgacctacac cgaactgaga   4140
tacctacagc gtgagctatg agaaagcgcc acgcttcccg aagggagaaa ggcggacagg   4200
tatccggtaa gcggcagggt cggaacagga gagcgcacga gggagcttcc agggggaaac   4260
gcctggtatc tttatagtcc tgtcgggttt cgccacctct gacttgagcg tcgatttttg   4320
tgatgctcgt caggggggcg gagcctatgg aaaaacgcca gcaacgcggc cttttacgg   4380
ttcctggcct tttgctggcc ttttgctcac atgttctttc ctgcgttatc ccctgattct   4440
gtggataacc gtattaccgc cttgagtga gctgataccg ctcgccgcag ccgaacgacc   4500
gagcgcagcg agtcagtgag cgaggaagcg gaagagcgcc caatacgcaa accgcctctc   4560
cccgcgcgtt ggccgattca ttaatgcagc agctgcgcgc tcgctcgctc actgaggccg   4620
cccgggcaaa gcccgggcgt cgggcgacct ttggtcgccc ggcctcagtg agcgagcgag   4680
cgcgcagaga gggagtggcc aactccatca ctaggggttc cttgtagtta atgattaacc   4740
cgccatgcta cttatctacg tagccatgct ctaggacatt gattattgac tagtggagtt   4800
ccgcgttaca taacttacgg taaatgcccc gcctggctga ccgcccaacg accccccgcc   4860
attgacgtca ataatgacgt atgttcccat agtaacgcca atagggactt tccattacg    4920
tcaatgggtg gagtatttac ggtaaactgc ccacttggca gtacatcaag tgtatcatat   4980
gccaagtacg ccccctattg acgtcaatga cggtaaatgg cccgcctggc attatgccca   5040
gtacatgacc ttatgggact ttcctacttg gcagtacatc tacgtattag tcatcgctat   5100
taccatggtc gaggtgagcc ccacgttctg cttcactctc cccatctccc ccccctcccc   5160
acccccaatt ttgtatttat ttatttttta attattttgt gcagcgatgg gggcgggggg   5220
ggggggggc gcgcgccagg cggggcgggg cgggcgagg ggcggggcgg ggcgaggcgg    5280
agaggtgcgg cggcagccaa tcagagcggc gcgctccgaa agtttccttt tatggcgagg   5340
cggcggcggc ggcggcccta taaaaagcga agcgcgcggc gggcgggagt cgctgcgcgc   5400
tgccttcgcc ccgtgcccg ctccgccgcc gcctcgcgcc gcccgccccg gctctgactg    5460
accgcgttac taaaacaggt aagtccggcc tccgcgccgg gttttggcgc ctcccgcggg   5520
cgcccccctc ctcacggcga gcgctgccac gtcagacgaa gggcgcagcg agcgtcctga   5580
tccttccgcc cggacgctca ggacagcggc ccgctgctca taagactcgg ccttagaacc   5640
ccagtatcag cagaaggaca ttttaggacg ggacttgggt gactctaggg cactggtttt   5700
ctttccagag agcggaacag gcgaggaaaa gtagtccctt ctcggcgatt ctgcggaggg   5760
atctccgtgg ggcggtgaac gccgatgatg cctctactaa ccatgttcat gttttctttt   5820
tttttctaca ggtcctgggt gacgaacagg gtaccgccac catgagggc atgaagctgc   5880
tgggggcgct gctggcactg gcggccctac tgcagggggc cgtgtccatg gcgctgtgga   5940
tgcgcctgct gccgctgctg gcgctgctgg cgctgtgggg cccggatccg gcggcggcgt   6000
ttgtgaacca gcatctgtgc ggcagccatc tggtggaagc gctgtatctg gtgtgcggcg   6060
aacgcgcctt tttttatacc ccgaaaaccc gccgcgaaggc ggaagatctg caggtgggcc   6120
aggtggaact gggcggcggc ccgggcgcgg gcagcctgca gccgctggcg ctggaaggca   6180
gcctgcagaa acgcggcatt gtgaacagt gctgcaccag catttgcagc ctgtatcagc   6240
tggaaaacta ttgcaacggg cggatcaggc ggatcaccca aatcttgtga caaaactcac   6300
acatgcccac cgtgcccagc acctgaactc ctgggggggac cgtcagtctt cctcttccc   6360
ccaaaaccca aggacaccct catgatctcc cggacccctg aggtcacatg cgtggtggtg   6420
gacgtgagcc acgaagaccc tgaggtcaag ttcaactggt acgtggacgg cgtggaggtg   6480
cataatgcca agacaaagcc gcgggaggag cagtacaaca gcacgtaccg tgtggtcagc   6540
gtcctcaccg tcctgcacca ggactggctg aatggcaagg agtacaagtg caaggtctcc   6600
aacaaagccc tcccagcccc catcgagaaa accatctcca aagccaaagg gcagccccga   6660
gaaccacagg tgtacaccct gcccccatcc cgggaggaga tgaccaagaa ccaggtcagc   6720
ctgacctgcc tggtcaaagg cttctatccc agcgacatcg ccgtggagtg ggagagcaat   6780
gggcagccgg agaacaacta caagaccacg cctcccgtgc tggactccga cggctccttc   6840
ttcctctaca gcaagctcac cgtggacaag agcaggtggc agcaggggaa cgtcttctca   6900
tgctccgtga tgcatgaggc tctgcacaac cactacacgc agaagagcct ctccctgtct   6960
ccgggtaaat ag                                                       6972
```